(12) United States Patent
Donlin et al.

(10) Patent No.: US 10,980,754 B2
(45) Date of Patent: Apr. 20, 2021

(54) ANTI-FUNGAL COMPOUNDS

(71) Applicants: SAINT LOUIS UNIVERSITY, St. Louis, MO (US); Research Foundation of the City University of New York, New York, NY (US)

(72) Inventors: Maureen J. Donlin, Kirkwood, MO (US); John Edwin Tavis, Kirkwood, MO (US); Ryan Murelli, Belleville, NJ (US); Marvin J. Meyers, Wentzville, MO (US)

(73) Assignees: SAINT LOUIS UNIVERSITY, St. Louis, MO (US); RESEARCH FOUNDATION OF THE CITY UNIVERSITY OF NEW YORK, New York, NY (US)

( * ) Notice: Subject to any disclaimer, the term of this patent is extended or adjusted under 35 U.S.C. 154(b) by 202 days.

(21) Appl. No.: 16/094,682

(22) PCT Filed: Apr. 19, 2017

(86) PCT No.: PCT/US2017/028390
§ 371 (c)(1),
(2) Date: Oct. 18, 2018

(87) PCT Pub. No.: WO2017/184752
PCT Pub. Date: Oct. 26, 2017

(65) Prior Publication Data
US 2019/0099385 A1 Apr. 4, 2019

Related U.S. Application Data

(60) Provisional application No. 62/447,158, filed on Jan. 17, 2017, provisional application No. 62/324,675, filed on Apr. 19, 2016.

(51) Int. Cl.
*A61K 31/122* (2006.01)
*A61K 31/4375* (2006.01)
(Continued)

(52) U.S. Cl.
CPC .......... *A61K 31/122* (2013.01); *A61K 31/341* (2013.01); *A61K 31/343* (2013.01); *A61K 31/365* (2013.01); *A61K 31/381* (2013.01); *A61K 31/4196* (2013.01); *A61K 31/4375* (2013.01); *A61K 31/4409* (2013.01); *A61K 31/4412* (2013.01); *A61K 31/4418* (2013.01); *A61K 31/496* (2013.01); *A61K 31/506* (2013.01); *A61K 31/513* (2013.01);
(Continued)

(58) Field of Classification Search
None
See application file for complete search history.

(56) References Cited

U.S. PATENT DOCUMENTS 3,374,271 A 3/1968 Steven
10,329,542 B2 6/2019 Tavis et al.
(Continued)

FOREIGN PATENT DOCUMENTS

WO WO 2012/172318 12/2012
WO WO 2014/047662 3/2014

OTHER PUBLICATIONS

Chang et al., "Discovery of structurally simplified analogs of colchicine as an immunosuppressant" Bioorganic and MedicinalChemistry Letters vol. 24 pp. 3121-3125 (Year: 2014).*
(Continued)

*Primary Examiner* — Eric Olson
(74) *Attorney, Agent, or Firm* — Parker Highlander PLLC

(57) ABSTRACT

The present disclosure provides compounds of the formula (I), (II), (III), wherein the variables are as defined herein for use in the treatment of fungal infections. In some embodiments, the fungal infection is an infection of *Cryptococcus neojormans* fungus. Also provided herein are compositions comprising a compound of formula I, II, or III and a second anti-fungal agent.

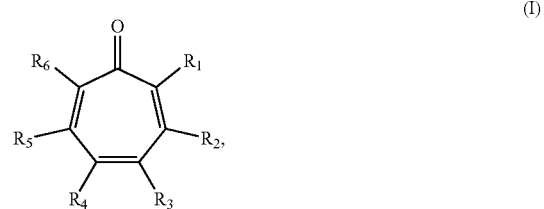

(I)

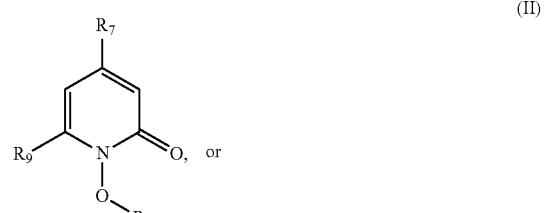

(II)

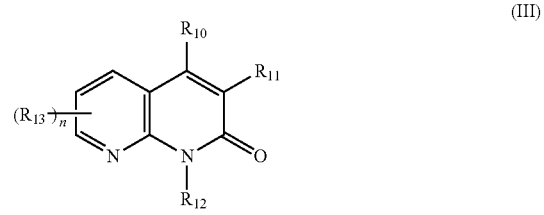

(III)

19 Claims, 14 Drawing Sheets

(51) Int. Cl.

| | | |
|---|---|---|
| C07C 63/38 | (2006.01) | |
| A61K 31/341 | (2006.01) | |
| A61K 31/365 | (2006.01) | |
| A61K 31/381 | (2006.01) | |
| A61K 31/4418 | (2006.01) | |
| A61K 31/506 | (2006.01) | |
| A61P 31/10 | (2006.01) | |
| A61K 31/7048 | (2006.01) | |
| A61K 31/513 | (2006.01) | |
| A61K 31/4196 | (2006.01) | |
| A61K 31/496 | (2006.01) | |
| C07C 49/835 | (2006.01) | |
| C07C 69/757 | (2006.01) | |
| C07C 49/84 | (2006.01) | |
| C07C 49/743 | (2006.01) | |
| C07C 49/717 | (2006.01) | |
| C07C 62/38 | (2006.01) | |
| C07C 49/747 | (2006.01) | |
| A61K 31/4409 | (2006.01) | |
| C07C 49/723 | (2006.01) | |
| C07C 327/22 | (2006.01) | |
| C07C 69/76 | (2006.01) | |
| C07C 69/92 | (2006.01) | |
| C07C 49/687 | (2006.01) | |
| C07C 49/753 | (2006.01) | |
| C07C 323/22 | (2006.01) | |
| C07C 69/78 | (2006.01) | |
| A61K 31/343 | (2006.01) | |
| A61K 31/4412 | (2006.01) | |
| C07C 327/26 | (2006.01) | |
| C07D 213/89 | (2006.01) | |
| C07D 471/04 | (2006.01) | |

(52) U.S. Cl.
CPC .......... *A61K 31/7048* (2013.01); *A61P 31/10* (2018.01); *C07C 49/687* (2013.01); *C07C 49/717* (2013.01); *C07C 49/723* (2013.01); *C07C 49/743* (2013.01); *C07C 49/747* (2013.01); *C07C 49/753* (2013.01); *C07C 49/835* (2013.01); *C07C 49/84* (2013.01); *C07C 62/38* (2013.01); *C07C 69/757* (2013.01); *C07C 69/76* (2013.01); *C07C 69/78* (2013.01); *C07C 69/92* (2013.01); *C07C 323/22* (2013.01); *C07C 327/22* (2013.01); *C07C 327/26* (2013.01); *C07D 213/89* (2013.01); *C07D 471/04* (2013.01); *C07C 2601/02* (2017.05); *C07C 2601/12* (2017.05); *C07C 2601/14* (2017.05); *C07C 2601/18* (2017.05); *C07C 2602/32* (2017.05); *C07C 2603/50* (2017.05)

(56) References Cited

U.S. PATENT DOCUMENTS

| | | | |
|---|---|---|---|
| 2015/0322413 | A1 | 11/2015 | Tavis et al. |
| 2016/0296521 | A1 | 10/2016 | Tavis et al. |
| 2018/0169083 | A1 | 6/2018 | Tavis et al. |
| 2018/0297924 | A1 | 10/2018 | Tavis et al. |
| 2019/0070165 | A1 | 3/2019 | Tavis et al. |

OTHER PUBLICATIONS

Neuville et al., "Primary Cutaneous Cryptococcosis: A Distinct Clinical Entity" Clinical Infectious Diseases vol. 36 pp. 337-347 (Year: 2003).*

Banerjee, et al., "Inhibition of nucleotide biosynthesis potentiates the antifungal activity of amphotericin B." *PLoS One* 9.1 (2014): e87246.

Berenbaum, M. C., "A method for testing for synergy with any number of agents," *Journal of Infections Diseases* 137.2 (1978): 122-130.

Ghannoum, et al., "Susceptibility testing of Cryptococcus neoformans: a microdilution technique." *Journal of Clinical Microbiology* 30.11 (1992): 2881-2886.

Guo, et al., "Characterization of the intracellular deproteinized relaxed circular DNA of hepatitis B virus: an intermediate of covalently closed circular DNA formation." *Journal of Virology* 81.22 (2007): 12472-12484.

International Preliminary Report on Patentability issued in International Application No. PCT/US2017/028390, dated Nov. 1, 2018.

International Search Report and Written Opinion issued in International Application No. PCT/US17/28390, dated Sep. 13, 2017.

Ireland, et al., "Synthetic α-hydroxytropolones inhibit replication of wild-type and acyclovir-resistant herpes simplex viruses." *Antimicrobial Agents and Chemotherapy* 60.4 (2016): 2140-2149.

Ishiyama, et al., "Antimalarial tropones and their Plasmodium falciparum glyoxalase I (pfGLOI) inhibitory activity." *The Journal of Antibiotics* 67.7 (2014): 545.

Jacobsen, et al., "Characterization and evaluation of pyrone and tropolone chelators for use in metalloprotein inhibitors." *Inorganica Chimica Acta* 360.1 (2007): 264-272.

Jacobsen, et al., "To bind zinc or not to bind zinc: an examination of innovative approaches to improved metalloproteinase inhibition." *Biochimica et Biophysica Acta (BBA)—Molecular Cell Research* 1803.1 (2010): 72-94.

Janbon, et al., "Analysis of the genome and transcriptome of *Cryptococcus neoformans* var. *grubii* reveals complex RNA expression and microevolution leading to virulence attenuation" *PLoS Genetics* 10.4 (2014): e1004261.

Klepser, et al., "Antifungal pharmacodynamic characteristics of fluconazole and amphotericin B against Cryptococcus neoformans." *The Journal of Antimicrobial Chemotherapy* 41.3 (1998): 397-401.

Komaki, et al. "Antifungal mechanism of hinokitiol against Candida albicans." *Biological and Pharmaceutical Bulletin* 31.4 (2008): 735-737.

Lim, et al., "Fungal diversity from Western redcedar fences and their resistanceto to β-thujaplicin." *Antoine Van Leeuwenhoek* 87.2 (2005): 109-117.

Lim, et al., "Screening fungi tolerant to Western red cedar (*Thuja plicata* Donn) extractives. Part 2. Development of a feeder strip assay." *Holzforschung* 61.2 (2007): 195-200.

Lu, et al., "Hydroxylated tropolones inhibit hepatitis B virus replication by blocking viral ribonuclease H activity." *Antimicrobial Agents and Chemotherapy* 59.2 (2015): 1070-1079.

Meck, et al., "The biology and synthesis of α-hydroxytropolones." *MedChemComm* 5.7 (2014): 842-852.

Mesa-Arango, et al., "The production of reactive oxygen species is a universal action mechanism of amphotericin B against pathoenic yeasts and contributes to the fungicidal effect of this drug." *Antimicrobial Agents and Chemotheraphy* 58.11 (2014): 6627-6638.

Nakano, et al., "Discovery and characterization of natural tropolones as inhibitors of the antibacterial target CapF from *Staphylococcus aureus.*" *Scientific Reports* 5 (2015): 15337.

Odds, Frank C., "Synergy, antagonism, and what the chequerboard puts between them." *Journal of Antimicrobial Chemotherapy* 52.1 (2003): 1-1.

Schulz, et al., "Biological activity of volatiles from marine and terrestrial bacteria." *Marine Drugs* 8.12 (2010): 2976-2987.

Tavis, et al., "The hepatitis B virus ribonuclease H is sensitive to inhibitors of the human immunodeficiency virus ribonuclease H and integrase enzymes." *PLoS Pathogens* 9.1 (2013): e1003125.

White, et al., "Comparison of three different in vitro methods of detecting synergy: time-kill, checkerboard, and E test." *Antimicrobial Agents and Chemotherapy* 40.8 (1996): 1914-1918.

* cited by examiner

148
 #149
 #150
 #151
 #152
 #153
 #154
 #155

ANTI-FUNGAL COMPOUNDS

The present application is a national phase application under 35 U.S.C. § 371 of International Application No. PCT/US2017/028390, filed Apr. 19, 2017, which claims the benefit of priority to U.S. Provisional Application Ser. No. 62/324,675, filed on Apr. 19, 2016 and U.S. Provisional Application Ser. No. 62/447,158, filed on Jan. 17, 2017, the entire contents of each of which are incorporated herein by reference.

The invention was made with government support under Grant Nos. R01 AI104494 and SC1 GM111158 awarded by the National Institutes of Health. The government has certain rights in the invention.

BACKGROUND

I. Field

The disclosure relates to the fields of pathology, fungi, and pharmaceuticals. More specifically, the disclosure relates to the identification of compounds showing antifungal activity against fungus including *C. neoformans*.

II. Related Art

Fungal infections, such as infections of *Cryptococcus neoformans*, are a growing problem amongst people who are immunocompromised. The *C. neoformans* is believed to cause up to 1 million infections each year particular in patients who are HIV positive and results in about 600,000 deaths annually. Fungal infections are also a major issue with patients who have undergone a major organ transplant. Estimates show that about 3% of transplant patients will experience an invasive fungal infection with an estimated mortality rate of 25% to 40% in the first year. The leading treatment for *C. neoformans* fungal infection is amphotericin B and flucytosine. This treatment course is long, has substantial toxicity, and even in the most favorable conditions retains 15-30% mortality. Given these significant handicaps to the current treatment options, there remains a need to develop new therapeutic options for these diseases.

SUMMARY

Thus, in accordance with the present disclosure, there is provided methods of inhibiting the growth of a fungus. In some embodiments, the present disclosure provides methods of treating a fungal infection in a patient comprising administering to the patient a therapeutically effective amount of a compound of the formula:

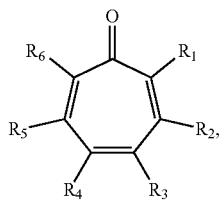

(I)

wherein:
$R_1$ and $R_6$ are each independently hydrogen, halo, or a group of the formula: $-X-Y_1$, wherein:
  X is C(O), O, S, or $NR_1'$, wherein:
  $R_1'$ is hydrogen, alkyl$_{(C \leq 8)}$, substituted alkyl$_{(C \leq 8)}$, aryl$_{(C \leq 8)}$, or substituted aryl$_{(C \leq 8)}$; and
  $Y_1$ is hydrogen, hydroxy, or alkyl$_{(C \leq 12)}$, aryl$_{(C \leq 12)}$, acyl$_{(C \leq 12)}$, alkoxy$_{(C \leq 12)}$, alkylsulfonyl$_{(C \leq 12)}$, arylsulfonyl$_{(C \leq 12)}$, or a substituted version of any of these groups;
$R_2$ and $R_5$ are each independently hydrogen, hydroxy, halo, alkyl$_{(C \leq 12)}$, substituted alkyl$_{(C \leq 12)}$, cycloalkyl$_{(C \leq 12)}$, substituted cycloalkyl$_{(C \leq 12)}$, alkenyl$_{(C \leq 12)}$, substituted alkenyl$_{(C \leq 12)}$, aryl$_{(C \leq 12)}$, substituted aryl$_{(C \leq 12)}$, aralkyl$_{(C \leq 12)}$, substituted aralkyl$_{(C \leq 12)}$, heteroaryl$_{(C \leq 12)}$, substituted heteroaryl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, or a group of the formula: $-C(O)Y_2R_2'$, wherein:
  $Y_2$ is alkenediyl$_{(C \leq 8)}$ or substituted alkenediyl$_{(C \leq 8)}$; and
  $R_2'$ is aryl$_{(C \leq 12)}$, heteroaryl$_{(C \leq 12)}$, arenediyl$_{(C \leq 12)}$-O-aryl$_{(C \leq 12)}$, or a substituted version of any of these groups; and
$R_3$ and $R_4$ are each independently hydrogen, hydroxy, halo, nitroso, alkyl$_{(C \leq 12)}$, substituted alkyl$_{(C \leq 12)}$, cycloalkyl$_{(C \leq 12)}$, substituted cycloalkyl$_{(C \leq 12)}$, alkenyl$_{(C \leq 12)}$, substituted alkenyl$_{(C \leq 12)}$, aryl$_{(C \leq 18)}$, substituted aryl$_{(C \leq 18)}$, heteroaryl$_{(C \leq 18)}$, substituted heteroaryl$_{(C \leq 18)}$, acyl$_{(C \leq 18)}$, substituted acyl$_{(C \leq 18)}$, amido$_{(C \leq 18)}$, substituted amido$_{(C \leq 18)}$, or $-C(O)R_a$ or $-S(O)_2R_a$ wherein:
  $R_a$ is alkyl$_{(C \leq 18)}$, cycloalkyl$_{(C \leq 18)}$, aryl$_{(C \leq 18)}$, heteroaryl$_{(C \leq 18)}$, alkoxy$_{(C \leq 18)}$, aryloxy$_{(C \leq 18)}$, -alkanediyl$_{(C \leq 6)}$-cycloalkyl$_{(C \leq 12)}$; or a substituted version of any of these groups; or
$R_2$ and $R_3$ are taken together and are a compound of the formula:

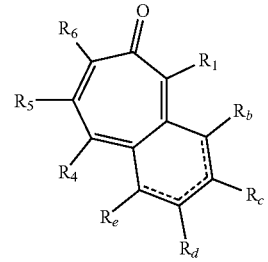

(IA)

wherein:
$R_b$, $R_c$, $R_d$, and $R_e$ are each independently hydrogen, hydroxy, or alkyl$_{(C \leq 8)}$, cycloalkyl$_{(C \leq 8)}$, alkenyl$_{(C \leq 8)}$, or a substituted version of any of these groups; or -alkanediyl$_{(C \leq 6)}$-alkylamino$_{(C \leq 8)}$, -alkane-diyl$_{(C \leq 6)}$-dialkylamino$_{(C \leq 8)}$, or a substituted version of either of these groups; or
$R_1$ and $R_2$ are taken together and are a compound of the formula:

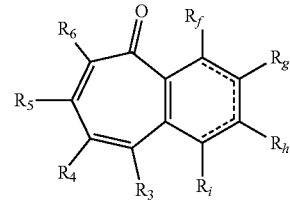

(IB)

wherein:

$R_f$, $R_g$, $R_h$, and $R_i$ are each independently hydrogen, hydroxy, or alkyl$_{(C \leq 8)}$, cycloalkyl$_{(C \leq 8)}$, alkenyl$_{(C \leq 8)}$, or a substituted version of any of these groups; or -alkanediyl$_{(C \leq 6)}$-alkylamino$_{(C \leq 8)}$, -alkane-diyl$_{(C \leq 6)}$-dialkylamino$_{(C \leq 8)}$, or a substituted version of either of these groups; or $R_3$ and $R_4$ are taken together and are a compound of the formula:

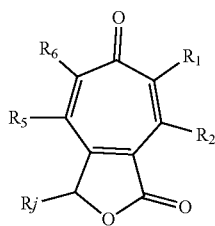

(IC)

wherein:

$R_j$ is hydrogen, hydroxy, halo, or alkyl$_{(C \leq 8)}$, cycloalkyl$_{(C \leq 8)}$, alkenyl$_{(C \leq 8)}$, or a substituted version of any of these groups; or -alkanediyl$_{(C \leq 6)}$-alkylamino$_{(C \leq 8)}$, -alkanediyl$_{(C \leq 6)}$-dialkylamino$_{(C \leq 8)}$, or a substituted version of either of these groups; or a compound of the formula:

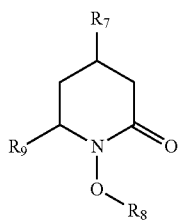

(II)

wherein:

$R_7$ is alkyl$_{(C \leq 12)}$, aryl$_{(C \leq 12)}$, aralkyl$_{(C \leq 12)}$, heteroaryl$_{(C \leq 12)}$, or a substituted version of any of these groups;

$R_8$ is hydrogen, alkyl$_{(C \leq 8)}$, or substituted alkyl$_{(C \leq 8)}$; and $R_9$ is hydrogen, alkyl$_{(C \leq 12)}$, or substituted alkyl$_{(C \leq 12)}$;

a compound of the formula:

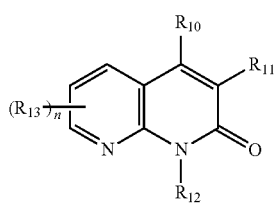

(III)

wherein:

$R_{10}$ is amino, hydroxy, or aryl$_{(C \leq 18)}$, aralkyl$_{(C \leq 18)}$, aryloxy$_{(C \leq 18)}$, cycloalkylamino$_{(C \leq 18)}$, aralkoxy$_{(C \leq 18)}$, arylamino$_{(C \leq 18)}$, aralkamino$_{(C \leq 18)}$, diarylamino$_{(C \leq 18)}$, diaralkamino$_{(C \leq 18)}$, or a substituted version of any of these groups;

$R_{11}$ is hydrogen, acyl$_{(C \leq 12)}$, or substituted acyl$_{(C \leq 12)}$, or —C(O)R$_a$; wherein:

$R_a$ is amino, hydroxy, alkoxy$_{(C \leq 8)}$, substituted alkoxy$_{(C \leq 8)}$, alkylamino$_{(C \leq 8)}$, substituted alkylamino$_{(C \leq 8)}$, dialkylamino$_{(C \leq 8)}$, or substituted dialkylamino$_{(C \leq 8)}$;

$R_{12}$ is hydrogen, alkoxy$_{(C \leq 8)}$, or substituted alkoxy$_{(C \leq 8)}$;

$R_{13}$ is amino, cyano, halo, hydroxy, nitro, alkyl$_{(C \leq 8)}$, substituted alkyl$_{(C \leq 8)}$, acyl$_{(C \leq 8)}$, substituted acyl$_{(C \leq 8)}$, alkoxy$_{(C \leq 8)}$, substituted alkoxy$_{(C \leq 8)}$, acyloxy$_{(C \leq 8)}$, substituted acyloxy$_{(C \leq 8)}$, alkylamino$_{(C \leq 8)}$, substituted alkylamino$_{(C \leq 8)}$, dialkylamino$_{(C \leq 8)}$, substituted dialkylamino$_{(C \leq 8)}$, amido$_{(C \leq 8)}$, or substituted amido$_{(C \leq 8)}$; and n is 1, 2, or 3;

or a pharmaceutically acceptable salt or tautomer thereof; provided that the compound is not thujaplicin when the fungal infection is a *Candida albicans* infection.

In some embodiments, the compound is further defined as:

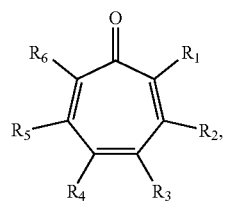

(I)

wherein:

$R_1$ and $R_6$ are each independently hydrogen, halo, or a group of the formula:

—X—Y$_1$, wherein:

X is O, S, or NR$_1$', wherein:

$R_1$' is hydrogen, alkyl$_{(C \leq 8)}$, substituted alkyl$_{(C \leq 8)}$, aryl$_{(C \leq 8)}$, or substituted aryl$_{(C \leq 8)}$; and $Y_1$ is hydrogen or alkyl$_{(C \leq 12)}$, aryl$_{(C \leq 12)}$, acyl$_{(C \leq 12)}$, alkylsulfonyl$_{(C \leq 12)}$, arylsulfonyl$_{(C \leq 12)}$, or a substituted version of any of these groups;

$R_2$ and $R_5$ are each independently hydrogen, hydroxy, halo, alkyl$_{(C \leq 12)}$, substituted alkyl$_{(C \leq 12)}$, cycloalkyl$_{(C \leq 12)}$, substituted cycloalkyl$_{(C \leq 12)}$, aryl$_{(C \leq 12)}$, substituted aryl$_{(C \leq 12)}$, aralkyl$_{(C \leq 12)}$, substituted aralkyl$_{(C \leq 12)}$, heteroaryl$_{(C \leq 12)}$, substituted heteroaryl$_{(C \leq 12)}$, alkoxy$_{(C \leq 12)}$, substituted alkoxy$_{(C \leq 12)}$, acyl$_{(C \leq 12)}$, or substituted acyl$_{(C \leq 12)}$; and $R_3$ and $R_4$ are each independently hydrogen, hydroxy, halo, nitroso, alkyl$_{(C \leq 12)}$, substituted alkyl$_{(C \leq 12)}$, cycloalkyl$_{(C \leq 12)}$, substituted cycloalkyl$_{(C \leq 12)}$, alkenyl$_{(C \leq 12)}$, substituted alkenyl$_{(C \leq 12)}$, aryl$_{(C \leq 18)}$, substituted aryl$_{(C \leq 18)}$, heteroaryl$_{(C \leq 18)}$, substituted heteroaryl$_{(C \leq 18)}$, acyl$_{(C \leq 18)}$, substituted acyl$_{(C \leq 18)}$, amido$_{(C \leq 18)}$, substituted amido$_{(C \leq 18)}$, or —C(O)R$_a$, wherein:

$R_a$ is alkyl$_{(C \leq 18)}$, cycloalkyl$_{(C \leq 18)}$, aryl$_{(C \leq 18)}$, heteroaryl$_{(C \leq 18)}$, alkoxy$_{(C \leq 18)}$, aryloxy$_{(C \leq 18)}$, -alkanediyl$_{(C \leq 6)}$-cycloalkyl$_{(C \leq 12)}$; or a substituted version of any of these groups; or $R_2$ and $R_3$ are taken together and are a compound of the formula:

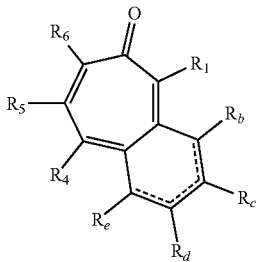

(IA)

wherein:

$R_b$, $R_c$, $R_d$, and $R_e$ are each independently hydrogen, hydroxy, or alkyl$_{(C\leq8)}$, cycloalkyl$_{(C\leq8)}$, alkenyl$_{(C\leq8)}$, or a substituted version of any of these groups; or -alkanediyl$_{(C\leq6)}$-alkylamino$_{(C\leq8)}$, -alkanediyl$_{(C\leq6)}$-dialkylamino$_{(C\leq8)}$, or a substituted version of either of these groups; or $R_1$ and $R_2$ are taken together and are a compound of the formula:

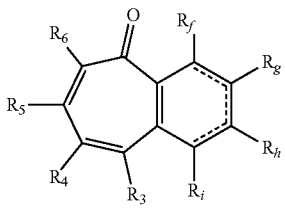

(IB)

wherein:

$R_f$, $R_g$, $R_h$, and $R_i$ are each independently hydrogen, hydroxy, or alkyl$_{(C\leq8)}$, cycloalkyl$_{(C\leq8)}$, alkenyl$_{(C\leq8)}$, or a substituted version of any of these groups; or -alkanediyl$_{(C\leq6)}$-alkylamino$_{(C\leq8)}$, -alkane-diyl$_{(C\leq6)}$-dialkylamino$_{(C\leq8)}$, or a substituted version of either of these groups; or $R_3$ and $R_4$ are taken together and are a compound of the formula:

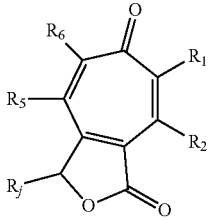

(IC)

wherein:

$R_j$ is hydrogen, hydroxy, halo, or alkyl$_{(C\leq8)}$, cycloalkyl$_{(C\leq8)}$, alkenyl$_{(C\leq8)}$, or a substituted version of any of these groups; or -alkanediyl$_{(C\leq6)}$-alkylamino$_{(C\leq8)}$, -alkane-diyl$_{(C\leq6)}$-dialkylamino$_{(C\leq8)}$, or a substituted version of either of these groups; or a compound of the formula:

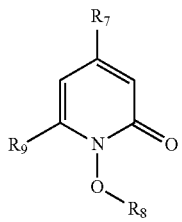

(II)

wherein:

$R_7$ is alkyl$_{(C\leq12)}$, aryl$_{(C\leq12)}$, aralkyl$_{(C\leq12)}$, heteroaryl$_{(C\leq12)}$, or a substituted version of any of these groups;

$R_8$ is hydrogen, alkyl$_{(C\leq8)}$, or substituted alkyl$_{(C\leq8)}$; and $R_9$ is hydrogen, alkyl$_{(C\leq12)}$, or substituted alkyl$_{(C\leq12)}$;

a compound of the formula:

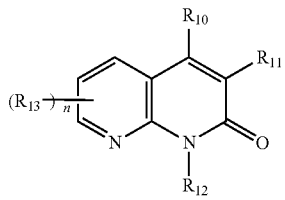

(III)

wherein:

$R_{10}$ is amino, hydroxy, or aryl$_{(C\leq18)}$, aralkyl$_{(C\leq18)}$, aryloxy$_{(C\leq18)}$, cycloalkylamino$_{(C\leq18)}$, aralkoxy$_{(C\leq18)}$, arylamino$_{(C\leq18)}$, aralkamino$_{(C\leq18)}$, diarylamino$_{(C\leq18)}$, diaralkamino$_{(C\leq18)}$, or a substituted version of any of these groups;

$R_{11}$ is hydrogen, acyl$_{(C\leq12)}$, or substituted acyl$_{(C\leq12)}$, or —C(O)R$_a$; wherein:

$R_a$ is amino, hydroxy, alkoxy$_{(C\leq8)}$, substituted alkoxy$_{(C\leq8)}$, alkylamino$_{(C\leq8)}$, substituted alkylamino$_{(C\leq8)}$, dialkylamino$_{(C\leq8)}$, or substituted dialkylamino$_{(C\leq8)}$;

$R_{12}$ is hydrogen, alkoxy$_{(C\leq8)}$, or substituted alkoxy$_{(C\leq8)}$;

$R_{13}$ is amino, cyano, halo, hydroxy, nitro, alkyl$_{(C\leq8)}$, substituted alkyl$_{(C\leq8)}$, acyl$_{(C\leq8)}$, substituted acyl$_{(C\leq8)}$, alkoxy$_{(C\leq8)}$, substituted alkoxy$_{(C\leq8)}$, acyloxy$_{(C\leq8)}$, substituted acyloxy$_{(C\leq8)}$, alkylamino$_{(C\leq8)}$, substituted alkylamino$_{(C\leq8)}$, dialkylamino$_{(C\leq8)}$, substituted dialkylamino$_{(C\leq8)}$, amido$_{(C\leq8)}$, or substituted amido$_{(C\leq8)}$; and n is 1, 2, or 3;

or a pharmaceutically acceptable salt or tautomer thereof.

In some embodiments, the fungal infection is an infection of a Basidiomycota fungus. In some embodiments, the fungal infection is an infection of a *Cryptococcus* fungus such as an infection of *Cryptococcus neoformans*. In other embodiments, the fungal infection is an infection of an Ascomycota fungus such as an infection of an *Aspergillus, Candida, Coccidioides, Histoplasma,* or *Blastomyces* fungus. In other embodiments, the fungal infection is an infection of *Mucoromycotina* fungus.

In some embodiments, the compound is further defined as:

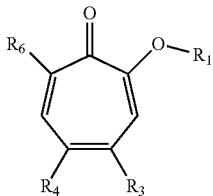

(IV)

wherein:
R$_1$ is hydrogen, alkyl$_{(C\leq 8)}$, substituted alkyl$_{(C\leq 8)}$, acyl$_{(C\leq 8)}$, or substituted acyl$_{(C\leq 8)}$;
R$_6$ is hydrogen, hydroxy, alkoxy$_{(C\leq 8)}$, substituted alkoxy$_{(C\leq 8)}$, acyloxy$_{(C\leq 8)}$, or substituted acyloxy$_{(C\leq 8)}$; and
R$_3$ and R$_4$ are each independently selected from hydrogen, hydroxy, nitroso, or alkyl$_{(C\leq 12)}$, substituted alkyl$_{(C\leq 12)}$, cycloalkyl$_{(C\leq 12)}$, substituted cycloalkyl$_{(C\leq 12)}$, alkenyl$_{(C\leq 12)}$, substituted alkenyl$_{(C\leq 12)}$, aryl$_{(C\leq 18)}$, substituted aryl$_{(C\leq 18)}$, heteroaryl$_{(C\leq 8)}$, substituted heteroaryl$_{(C\leq 8)}$, acyl$_{(C\leq 12)}$, substituted acyl$_{(C\leq 12)}$, or —C(O)R$_a$, wherein:
R$_a$ is alkyl$_{(C\leq 18)}$, cycloalkyl$_{(C\leq 18)}$, aryl$_{(C\leq 18)}$, heteroaryl$_{(C\leq 18)}$, alkoxy$_{(C\leq 18)}$, aryloxy$_{(C\leq 18)}$, -alkanediyl$_{(C\leq 6)}$-cycloalkyl$_{(C\leq 12)}$; or a substituted version of any of these groups;
or a pharmaceutically acceptable salt or tautomer thereof. In some embodiments, the compound is further defined as:

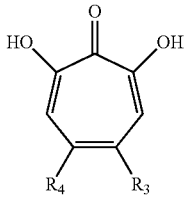

(V)

wherein:
R$_3$ and R$_4$ are each independently hydrogen, hydroxy, alkyl$_{(C\leq 12)}$, substituted alkyl$_{(C\leq 12)}$, cycloalkyl$_{(C\leq 12)}$, substituted cycloalkyl$_{(C\leq 12)}$, alkenyl$_{(C\leq 12)}$, substituted alkenyl$_{(C\leq 12)}$, aryl$_{(C\leq 18)}$, substituted aryl$_{(C\leq 18)}$, heteroaryl$_{(C\leq 8)}$, substituted heteroaryl$_{(C\leq 8)}$, acyl$_{(C\leq 12)}$, substituted acyl$_{(C\leq 12)}$, or —C(O)R$_a$, wherein:
R$_a$ is alkyl$_{(C\leq 18)}$, cycloalkyl$_{(C\leq 18)}$, aryl$_{(C\leq 18)}$, heteroaryl$_{(C\leq 18)}$, alkoxy$_{(C\leq 18)}$, aryloxy$_{(C\leq 18)}$, -alkanediyl$_{(C\leq 6)}$-cycloalkyl$_{(C\leq 12)}$; or a substituted version of any of these groups;
or a pharmaceutically acceptable salt or tautomer thereof.

In other embodiments, the compound is further defined as:

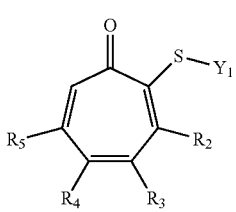

(V)

wherein:
Y$_1$ is hydrogen or alkyl$_{(C\leq 12)}$, aryl$_{(C\leq 12)}$, acyl$_{(C\leq 12)}$, alkylsulfonyl$_{(C\leq 12)}$, arylsulfonyl$_{(C\leq 12)}$, or a substituted version of any of these groups;
R$_2$ and R$_5$ are each independently hydrogen, hydroxy, halo, alkyl$_{(C\leq 12)}$, substituted alkyl$_{(C\leq 12)}$, cycloalkyl$_{(C\leq 12)}$, substituted cycloalkyl$_{(C\leq 12)}$, aryl$_{(C\leq 12)}$, substituted aryl$_{(C\leq 12)}$, aralkyl$_{(C\leq 12)}$, substituted aralkyl$_{(C\leq 12)}$, heteroaryl$_{(C\leq 12)}$, substituted heteroaryl$_{(C\leq 12)}$, alkoxy$_{(C\leq 12)}$, substituted alkoxy$_{(C\leq 12)}$, acyl$_{(C\leq 12)}$, or substituted acyl$_{(C\leq 12)}$; and
R$_3$ and R$_4$ are each independently hydrogen, hydroxy, halo, nitroso, alkyl$_{(C\leq 12)}$, substituted alkyl$_{(C\leq 12)}$, cycloalkyl$_{(C\leq 12)}$, substituted cycloalkyl$_{(C\leq 12)}$, alkenyl$_{(C\leq 12)}$, substituted alkenyl$_{(C\leq 12)}$, aryl$_{(C\leq 18)}$, substituted aryl$_{(C\leq 18)}$, heteroaryl$_{(C\leq 18)}$, substituted heteroaryl$_{(C\leq 18)}$, acyl$_{(C\leq 18)}$, substituted acyl$_{(C\leq 18)}$, amido$_{(C\leq 18)}$, substituted amido$_{(C\leq 18)}$, or —C(O)R$_a$, wherein:
R$_a$ is alkyl$_{(C\leq 18)}$, cycloalkyl$_{(C\leq 18)}$, aryl$_{(C\leq 18)}$, heteroaryl$_{(C\leq 18)}$, alkoxy$_{(C\leq 18)}$, aryloxy$_{(C\leq 18)}$, -alkanediyl$_{(C\leq 6)}$-cycloalkyl$_{(C\leq 12)}$; or a substituted version of any of these groups;
or a pharmaceutically acceptable salt or tautomer thereof. In some embodiments, the compound is further defined as:

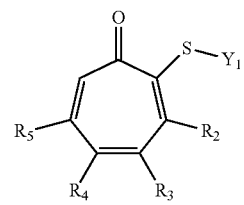

(VI)

wherein:
Y$_1$ is hydrogen or alkyl$_{(C\leq 12)}$, aryl$_{(C\leq 12)}$, acyl$_{(C\leq 12)}$, alkylsulfonyl$_{(C\leq 12)}$, arylsulfonyl$_{(C\leq 12)}$, or a substituted version of any of these groups;
R$_2$ and R$_5$ are each independently hydrogen, hydroxy, halo, alkyl$_{(C\leq 12)}$, substituted alkyl$_{(C\leq 12)}$, cycloalkyl$_{(C\leq 12)}$, substituted cycloalkyl$_{(C\leq 12)}$, alkoxy$_{(C\leq 12)}$, substituted alkoxy$_{(C\leq 12)}$, acyl$_{(C\leq 12)}$, or substituted acyl$_{(C\leq 12)}$; and
R$_3$ and R$_4$ are each independently hydrogen, hydroxy, halo, nitroso, alkyl$_{(C\leq 12)}$, substituted alkyl$_{(C\leq 12)}$, cycloalkyl$_{(C\leq 12)}$, substituted cycloalkyl$_{(C\leq 12)}$, alkenyl$_{(C\leq 12)}$, substituted alkenyl$_{(C\leq 12)}$, aryl$_{(C\leq 18)}$, substituted aryl$_{(C\leq 18)}$, heteroaryl$_{(C\leq 18)}$, substituted heteroaryl$_{(C\leq 18)}$, acyl$_{(C\leq 18)}$, substituted acyl$_{(C\leq 18)}$, amido$_{(C\leq 18)}$, substituted amido$_{(C\leq 18)}$, or —C(O)R$_a$, wherein:
R$_a$ is alkyl$_{(C\leq 18)}$, cycloalkyl$_{(C\leq 18)}$, aryl$_{(C\leq 18)}$, heteroaryl$_{(C\leq 18)}$, alkoxy$_{(C\leq 18)}$, aryloxy$_{(C\leq 18)}$, -alkanediyl$_{(C\leq 6)}$-cycloalkyl$_{(C\leq 12)}$; or a substituted version of any of these groups;
or a pharmaceutically acceptable salt or tautomer thereof. In some embodiments, the compound is further defined as:

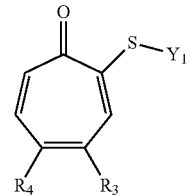

(VII)

wherein:
  $Y_1$ is hydrogen or alkyl$_{(C≤12)}$, aryl$_{(C≤12)}$, acyl$_{(C≤12)}$, or a substituted version of any of these groups; and
  $R_3$ and $R_4$ are each independently hydrogen, hydroxy, halo, nitroso, alkyl$_{(C≤12)}$, substituted alkyl$_{(C≤12)}$, cycloalkyl$_{(C≤12)}$, substituted cycloalkyl$_{(C≤12)}$, alkenyl$_{(C≤12)}$, or substituted alkenyl$_{(C≤12)}$;
    or a pharmaceutically acceptable salt or tautomer thereof.

In some embodiments, $Y_1$ is acyl$_{(C≤12)}$ or substituted acyl$_{(C≤12)}$ such as 4-methylbenzoyl. In other embodiments, $Y_1$ is hydrogen.

In other embodiments, the compound is further defined as:

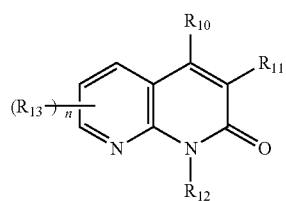
(III)

wherein:
  $R_{10}$ is amino, hydroxy, aryl$_{(C≤18)}$, aralkyl$_{(C≤18)}$, aryloxy$_{(C≤18)}$, aralkoxy$_{(C≤18)}$, cycloalkylamino$_{(C≤12)}$, arylamino$_{(C≤18)}$, aralkamino$_{(C≤18)}$, diarylamino$_{(C≤18)}$, or diaralkamino$_{(C≤18)}$;
  $R_{11}$ is hydrogen, acyl$_{(C≤12)}$, or substituted acyl$_{(C≤12)}$, or —C(O)$R_a$; wherein:
    $R_a$ is amino, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤8)}$, or substituted dialkylamino$_{(C≤8)}$; and
  $R_{12}$ is hydrogen, alkoxy$_{(C≤8)}$, or substituted alkoxy$_{(C≤8)}$;
or a pharmaceutically acceptable salt or tautomer thereof.

In some embodiments, the compound is further defined as:

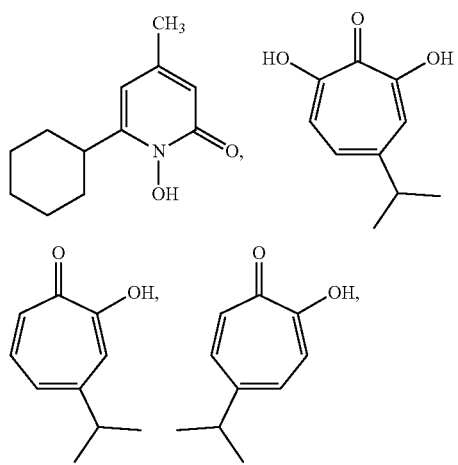

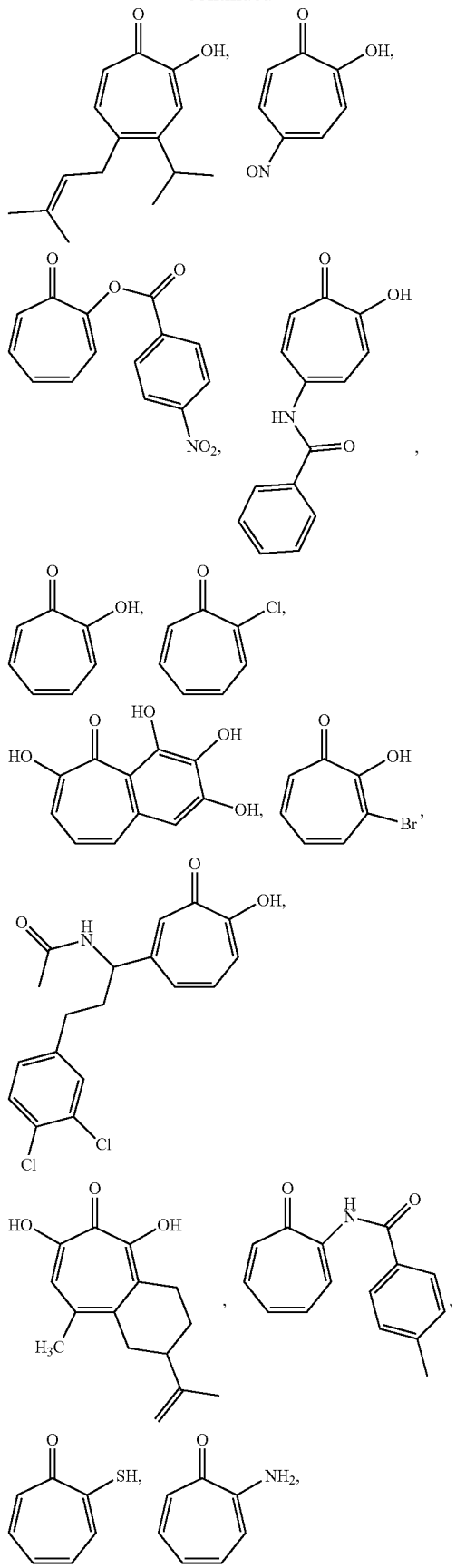

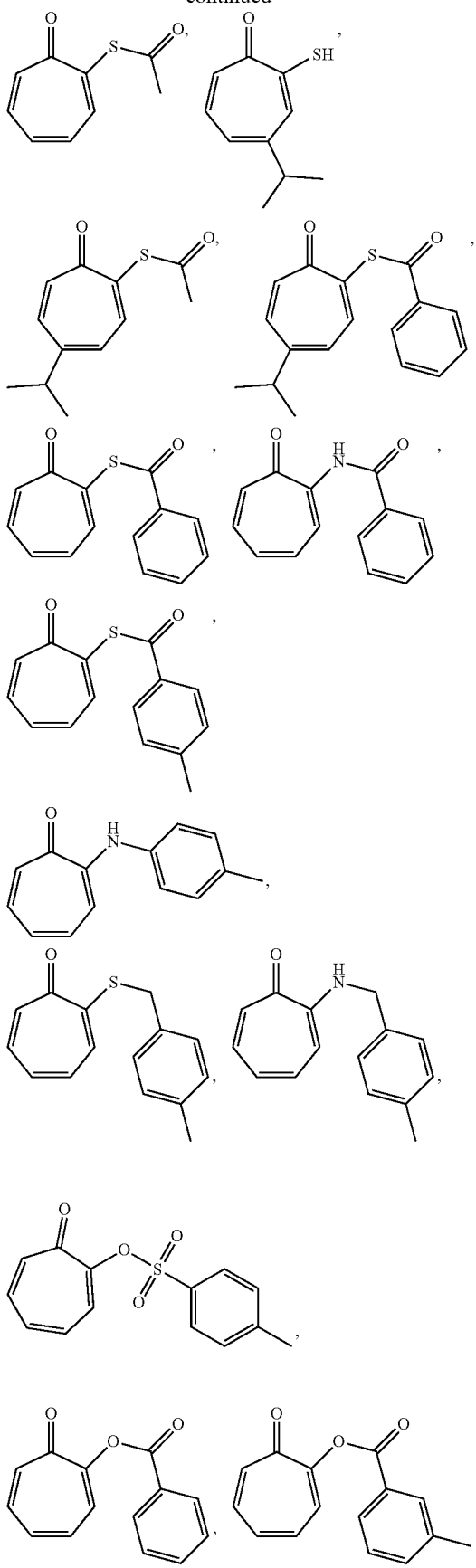
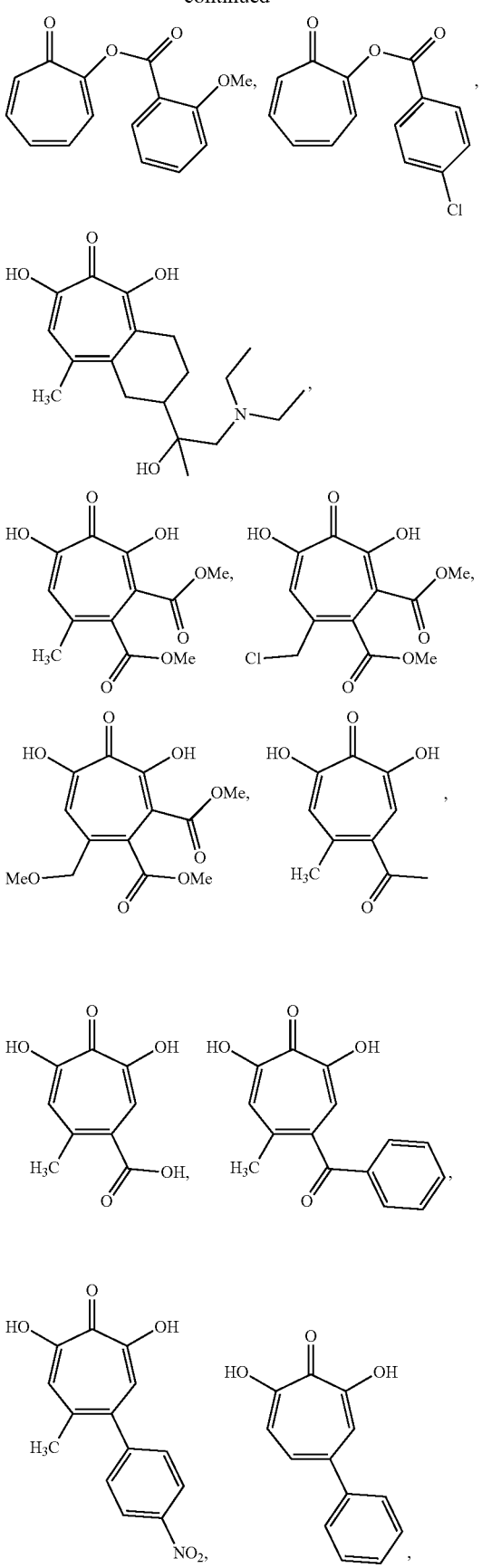

-continued
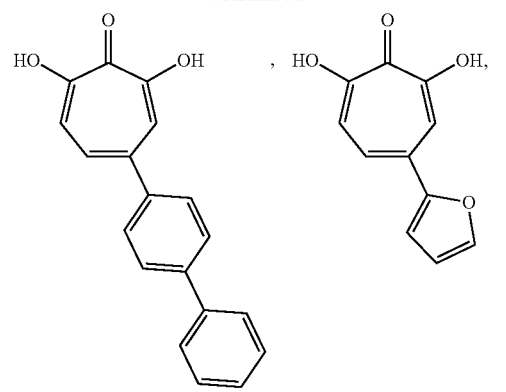
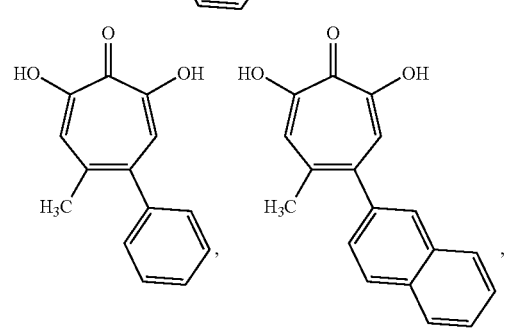
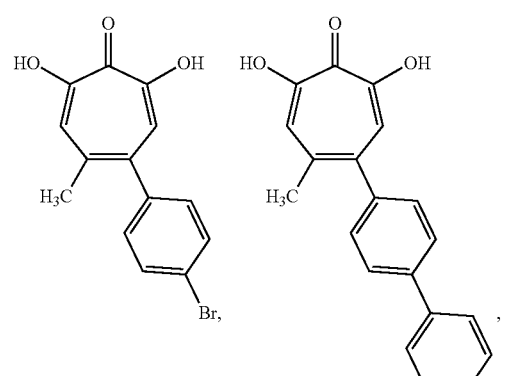
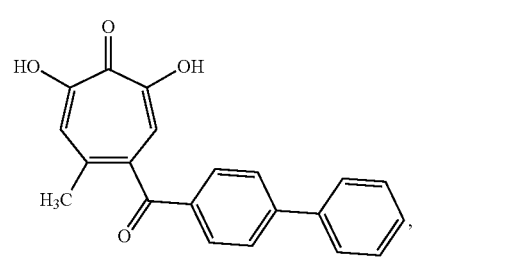
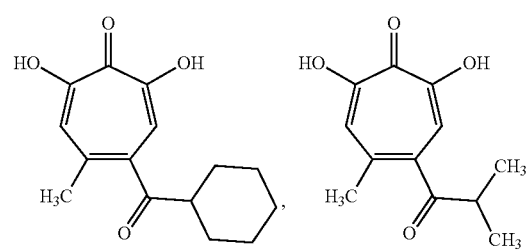
-continued
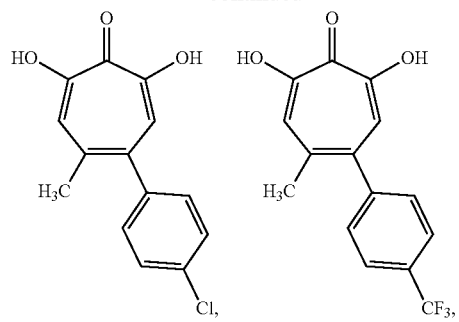
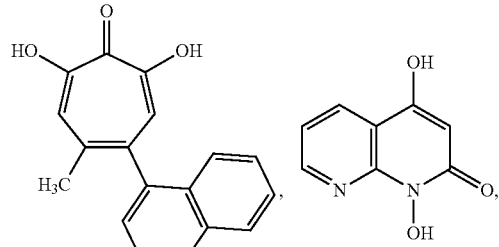
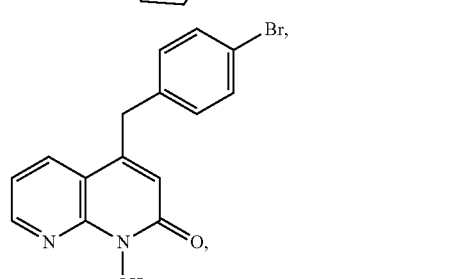
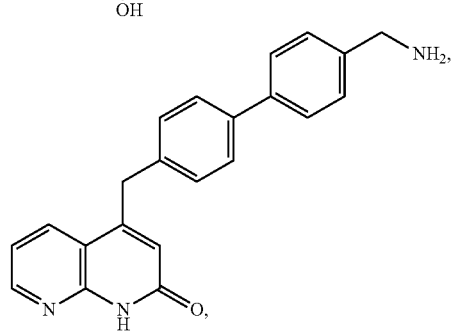
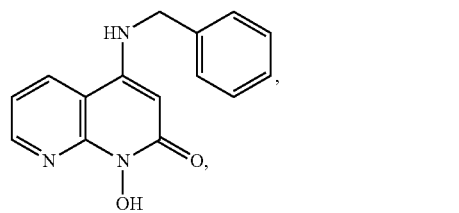
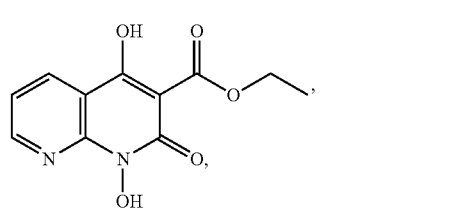

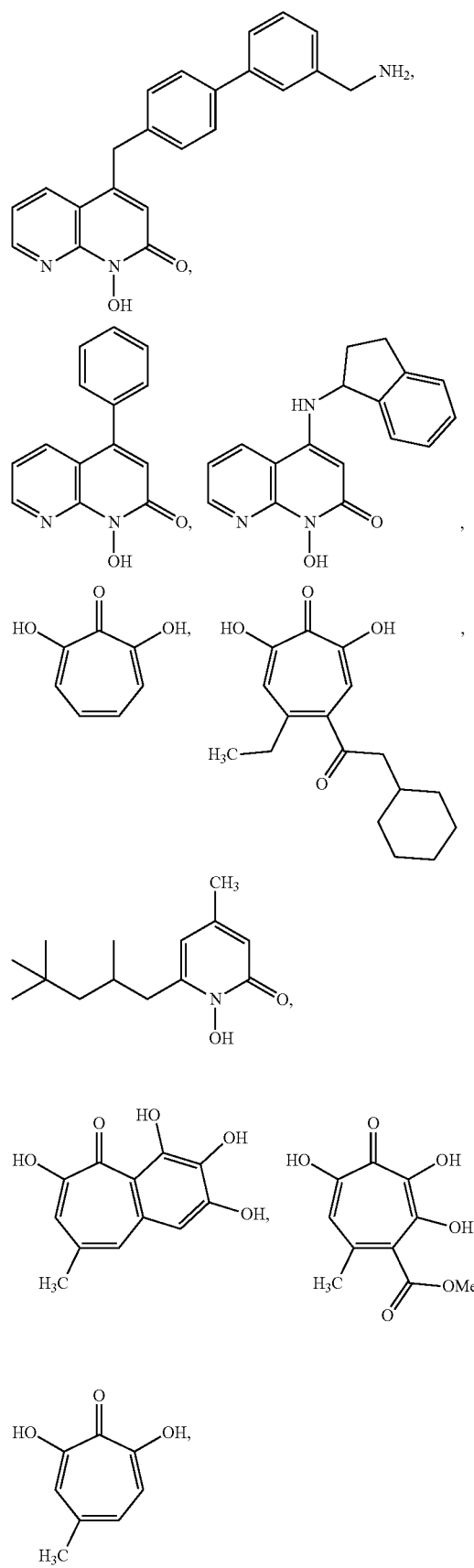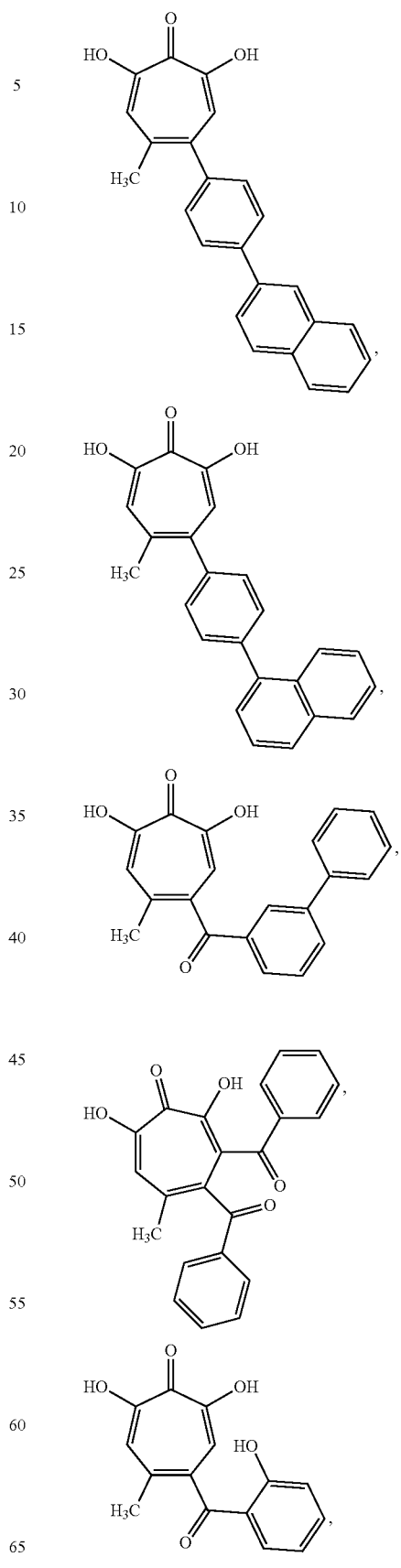

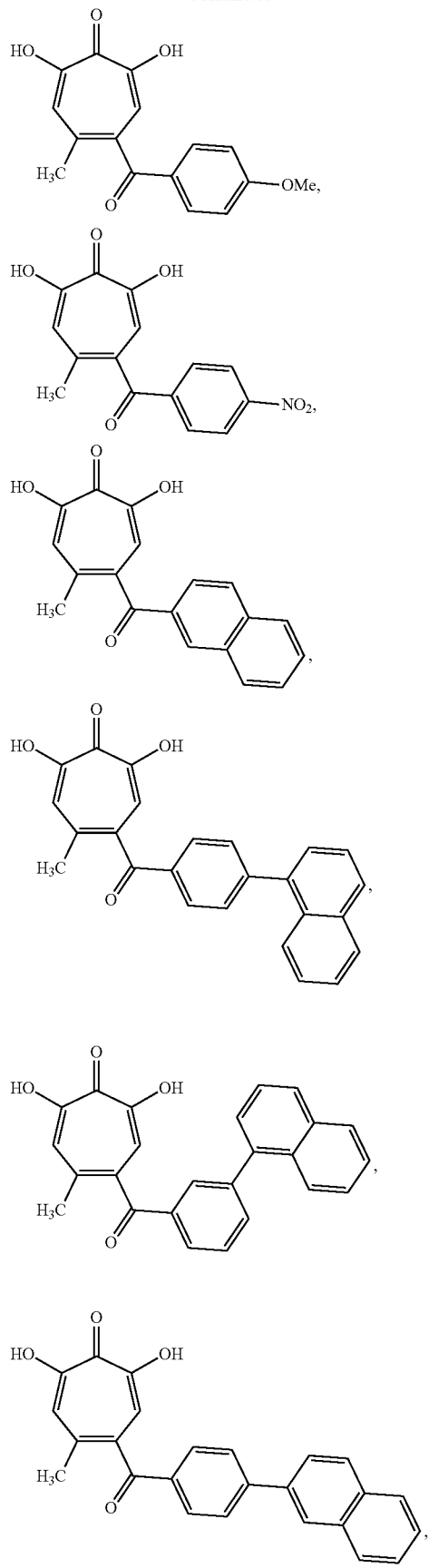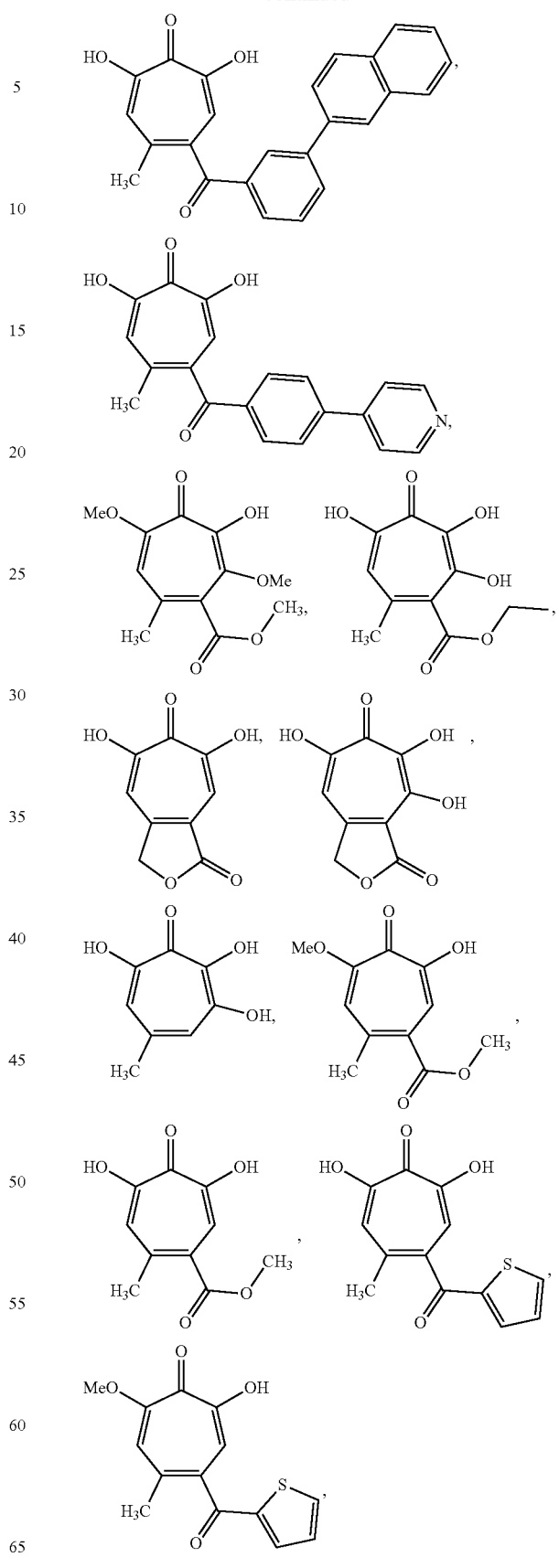

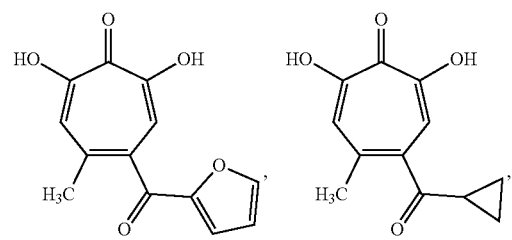
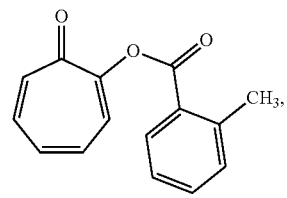
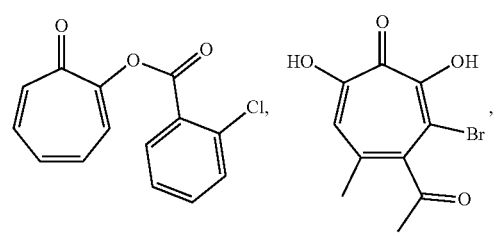
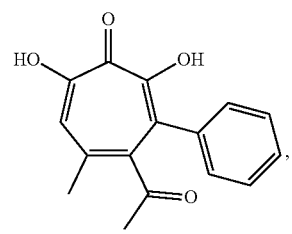
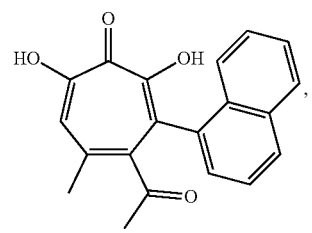
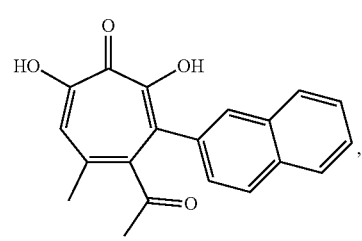
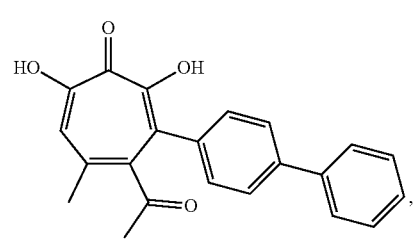
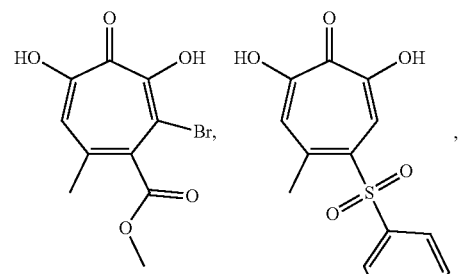
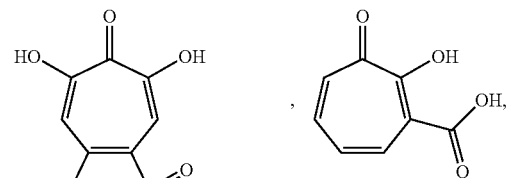
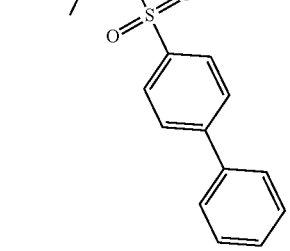
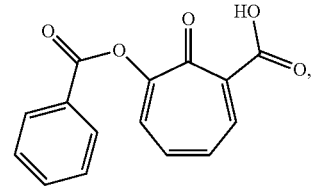
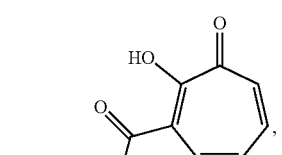
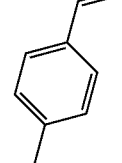
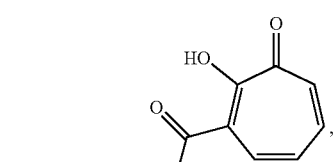
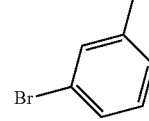

-continued
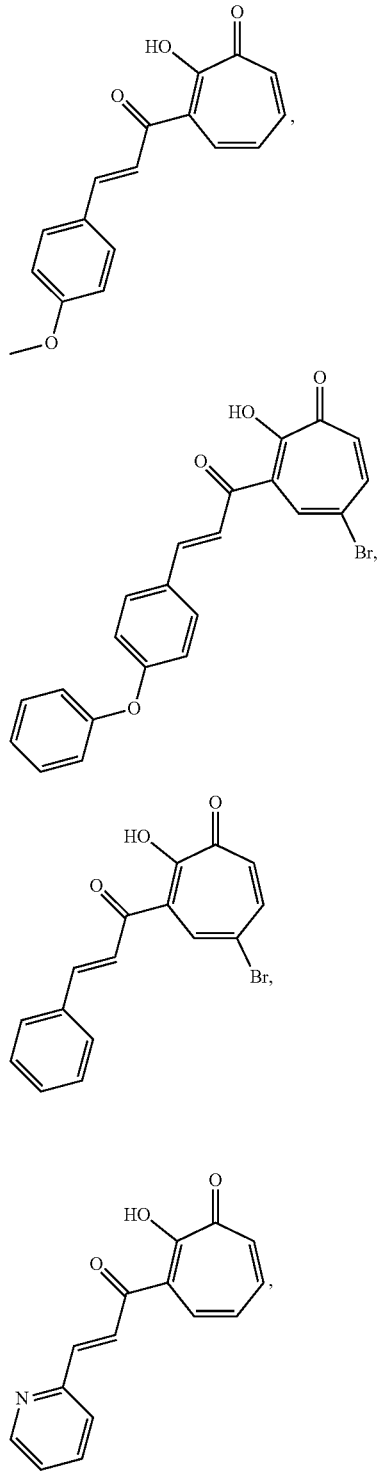
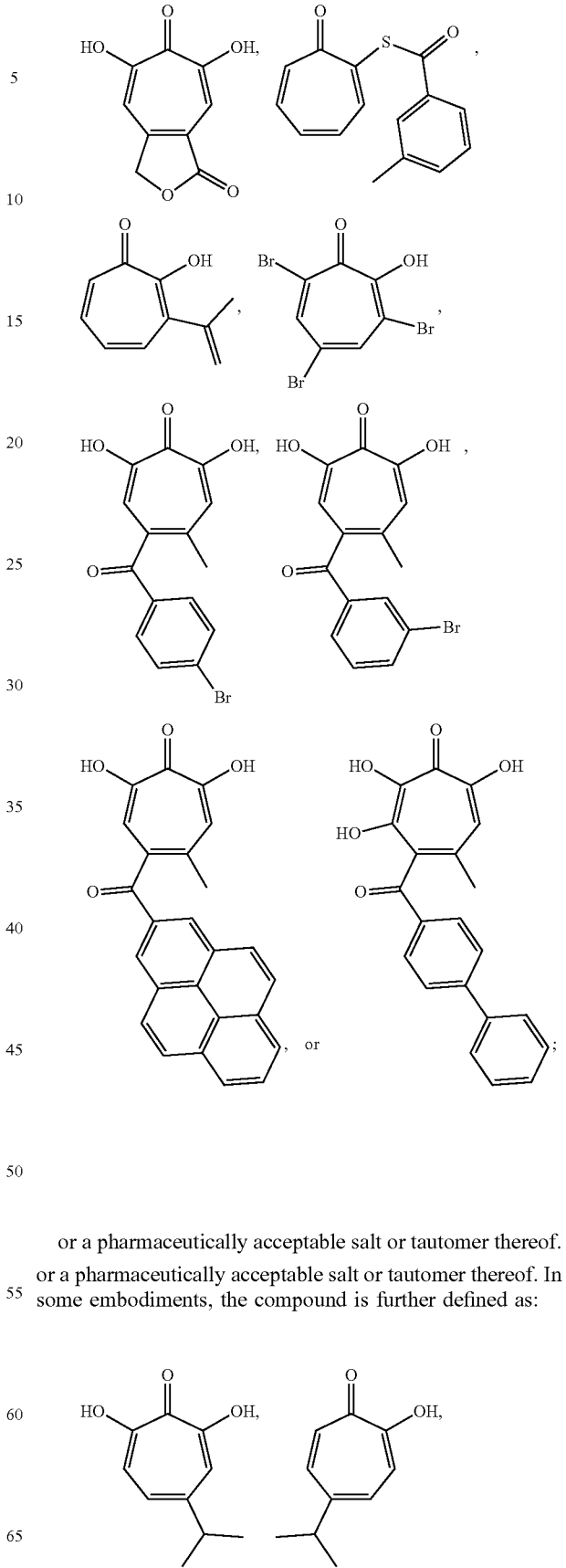
or a pharmaceutically acceptable salt or tautomer thereof. In some embodiments, the compound is further defined as:
or a pharmaceutically acceptable salt or tautomer thereof.

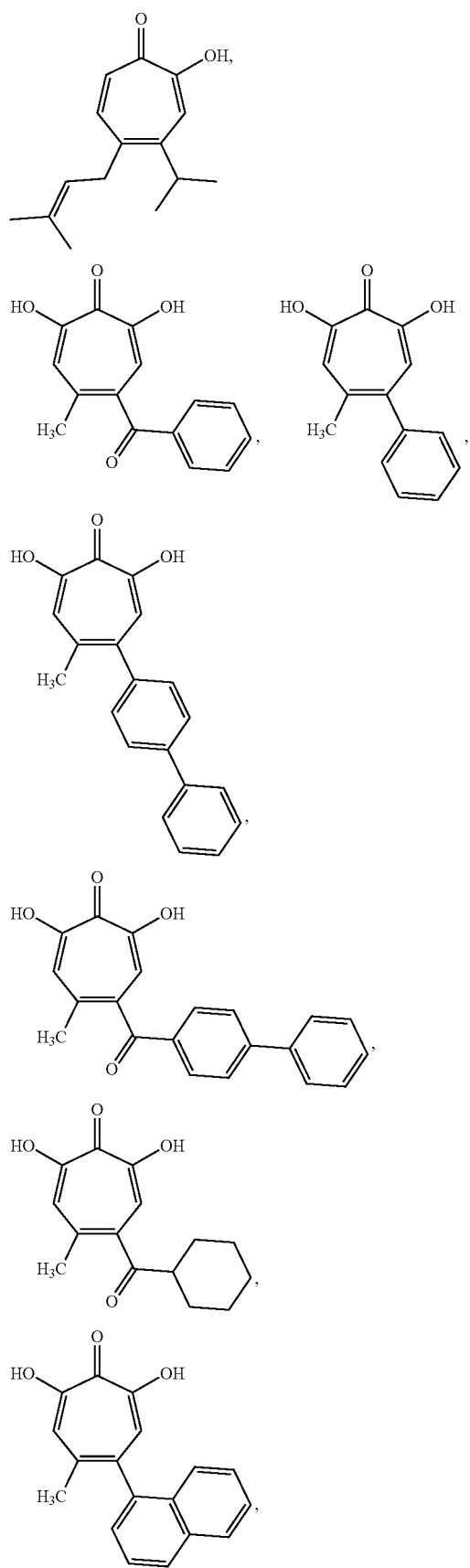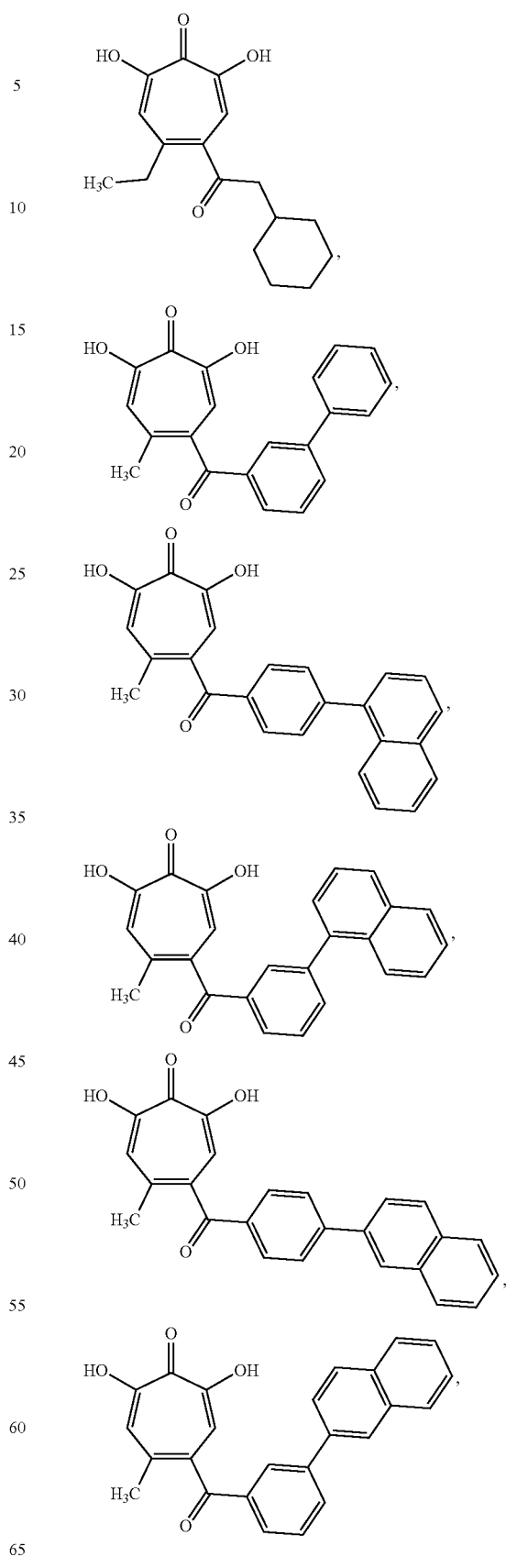

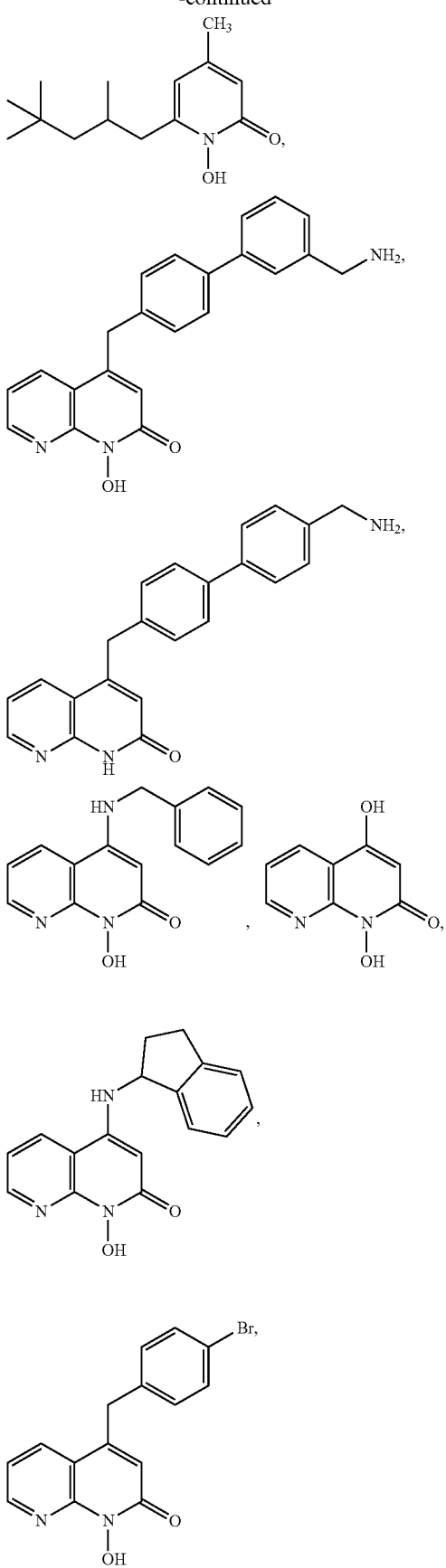

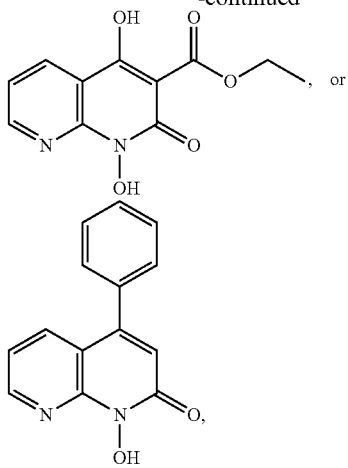

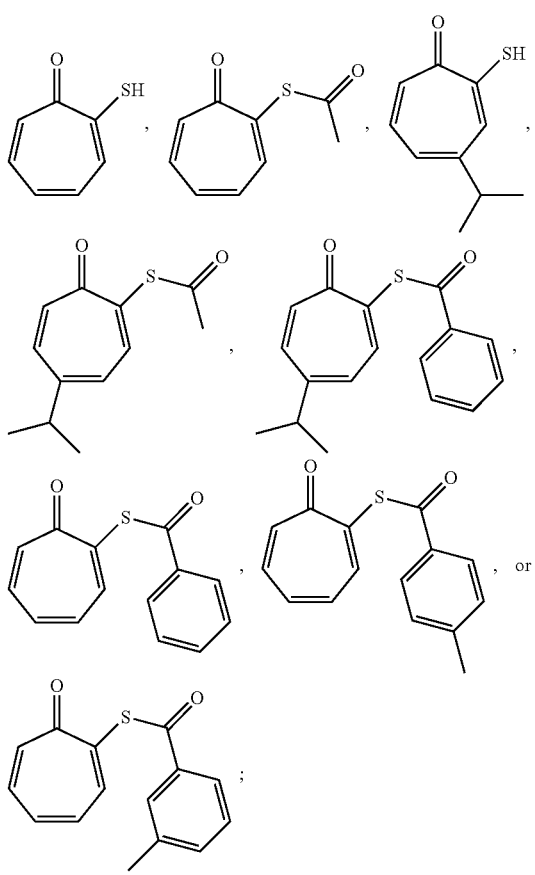

or a pharmaceutically acceptable salt or tautomer thereof. In some embodiments, the compound is further defined as:

or a pharmaceutically acceptable salt or tautomer thereof.

In some embodiments, the compound is formulated as a pharmaceutical composition comprising the compound and an excipient. In some embodiments, the pharmaceutical composition is formulated for in vivo administration. In some embodiments, the pharmaceutical composition is formulated for oral administration, intraarterial administration, intravenous administration, parenteral administration, or for administration to the lungs. In some embodiments, the pharmaceutical composition is formulated as a unit dose. In some embodiments, the patient is a mammal such as a human.

In some embodiments, the patient has a weakened immune system. In other embodiments, the patient has undergone an organ transplant. In some embodiments, the patient has human immunodeficiency virus. In some embodiments, the patient is taking a medicine which results in reduced immune activity such as a corticosteroid or a treatment for rheumatoid arthritis.

In some embodiments, the methods further comprise administering a second anti-fungal therapy. In some embodiments, the second anti-fungal therapy is a therapy targeting the ergosterol biosynthetic pathway. In some embodiments, the second anti-fungal therapy is Amphotericin B, fluconazole, itraconazole, posaconazole, or voriconazole. In some embodiments, the second anti-fungal therapy is voriconazole. In other embodiments, the second anti-fungal therapy is echinocandins or flucytosine.

In some embodiments, the fungal infection is in the central nervous system. In other embodiments, the fungal infection is in the lungs. In some embodiments, the fungal infection results in a disease. In some embodiments, the fungal infection results in cryptococcosis such as cryptococcal meningitis. In some embodiments, the compound is administered once. In other embodiments, the compound is administered two or more times. In some embodiments, the compound is administered over a time period from 1 day to 2 years. In some embodiments, the time period is from about 1 week to about 8 weeks. In other embodiments, the time period is from about 6 months to about 12 months.

In yet another aspect, the present disclosure provides methods of treating a condition associated with a *Cryptococcus neoformans* infection in a patient in need thereof comprising administering to the patient a therapeutically effective amount of a compound of the formula:

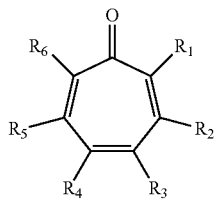

(I)

wherein:
$R_1$ and $R_6$ are each independently hydrogen, halo, or a group of the formula: —X—$Y_1$, wherein:
X is C(O), O, S, or N$R_1'$, wherein:
$R_1'$ is hydrogen, alkyl$_{(C \leq 8)}$, substituted alkyl$_{(C \leq 8)}$, aryl$_{(C \leq 8)}$, or substituted aryl$_{(C \leq 8)}$; and
$Y_1$ is hydrogen, hydroxy, or alkyl$_{(C \leq 12)}$, aryl$_{(C \leq 12)}$, acyl$_{(C \leq 12)}$, alkoxy$_{(C \leq 12)}$, alkylsulfonyl$_{(C \leq 12)}$, arylsulfonyl$_{(C \leq 12)}$, or a substituted version of any of these groups;
$R_2$ and $R_5$ are each independently hydrogen, hydroxy, halo, alkyl$_{(C \leq 12)}$, substituted alkyl$_{(C \leq 12)}$, cycloalkyl$_{(C \leq 12)}$, substituted cycloalkyl$_{(C \leq 12)}$, alkenyl$_{(C \leq 12)}$, substituted alkenyl$_{(C \leq 12)}$, aryl$_{(C \leq 12)}$, substituted aryl$_{(C \leq 12)}$, aralkyl$_{(C \leq 12)}$, substituted aralkyl$_{(C \leq 12)}$, heteroaryl$_{(C \leq 12)}$, substituted heteroaryl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, or a group of the formula: —C(O)$Y_2R_2'$, wherein:

$Y_2$ is alkenediyl$_{(C \leq 8)}$ or substituted alkenediyl$_{(C \leq 8)}$; and
$R_2'$ is aryl$_{(C \leq 12)}$, heteroaryl$_{(C \leq 12)}$, arenediyl$_{(C \leq 12)}$-O-aryl$_{(C \leq 12)}$, or a substituted version of any of these groups; and
$R_3$ and $R_4$ are each independently hydrogen, hydroxy, halo, nitroso, alkyl$_{(C \leq 12)}$, substituted alkyl$_{(C \leq 12)}$, cycloalkyl$_{(C \leq 12)}$, substituted cycloalkyl$_{(C \leq 12)}$, alkenyl$_{(C \leq 12)}$, substituted alkenyl$_{(C \leq 12)}$, aryl$_{(C \leq 18)}$, substituted aryl$_{(C \leq 18)}$, heteroaryl$_{(C \leq 18)}$, substituted heteroaryl$_{(C \leq 18)}$, acyl$_{(C \leq 18)}$, substituted acyl$_{(C \leq 18)}$, amido$_{(C \leq 18)}$, substituted amido$_{(C \leq 18)}$, or —C(O)$R_a$ or —S(O)$_2R_a$ wherein:
$R_a$ is alkyl$_{(C \leq 18)}$, cycloalkyl$_{(C \leq 18)}$, aryl$_{(C \leq 18)}$, heteroaryl$_{(C \leq 18)}$, alkoxy$_{(C \leq 18)}$, aryloxy$_{(C \leq 18)}$, -alkanediyl$_{(C \leq 6)}$-cycloalkyl$_{(C \leq 12)}$; or a substituted version of any of these groups; or
$R_2$ and $R_3$ are taken together and are a compound of the formula:

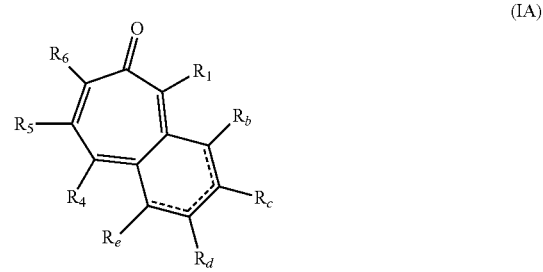

(IA)

wherein:
$R_b$, $R_c$, $R_d$, and $R_e$ are each independently hydrogen, hydroxy, or alkyl$_{(C \leq 8)}$, cycloalkyl$_{(C \leq 8)}$, alkenyl$_{(C \leq 8)}$, or a substituted version of any of these groups; or -alkanediyl$_{(C \leq 6)}$-alkylamino$_{(C \leq 8)}$, -alkanediyl$_{(C \leq 6)}$-dialkylamino$_{(C \leq 8)}$, or a substituted version of either of these groups; or
$R_1$ and $R_2$ are taken together and are a compound of the formula:

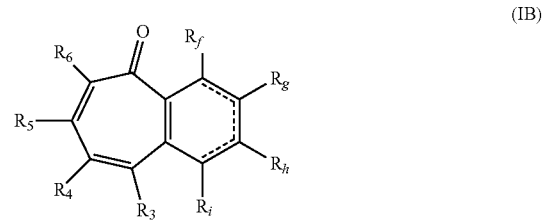

(IB)

wherein:
$R_f$, $R_g$, $R_h$, and $R_i$ are each independently hydrogen, hydroxy, or alkyl$_{(C \leq 8)}$, cycloalkyl$_{(C \leq 8)}$, alkenyl$_{(C \leq 8)}$, or a substituted version of any of these groups; or -alkanediyl$_{(C \leq 6)}$-alkylamino$_{(C \leq 8)}$, -alkanediyl$_{(C \leq 6)}$-dialkylamino$_{(C \leq 8)}$, or a substituted version of either of these groups; or
$R_3$ and $R_4$ are taken together and are a compound of the formula:

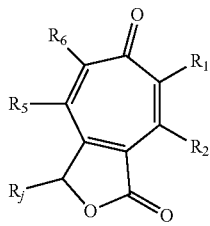

(IC)

wherein:
$R_j$ is hydrogen, hydroxy, halo, or alkyl$_{(C≤8)}$, cycloalkyl$_{(C≤8)}$, alkenyl$_{(C≤8)}$, or a substituted version of any of these groups; or -alkanediyl$_{(C≤6)}$-alkylamino$_{(C≤8)}$, -alkanediyl$_{(C≤6)}$-dialkylamino$_{(C≤8)}$, or a substituted version of either of these groups; or
a compound of the formula:

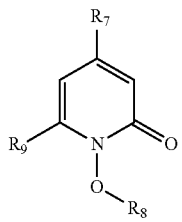

(II)

wherein:
$R_7$ is alkyl$_{(C≤12)}$, aryl$_{(C≤12)}$, aralkyl$_{(C≤12)}$, heteroaryl$_{(C≤12)}$, or a substituted version of any of these groups;
$R_8$ is hydrogen, alkyl$_{(C≤8)}$, or substituted alkyl$_{(C≤8)}$; and
$R_9$ is hydrogen, alkyl$_{(C≤12)}$, or substituted alkyl$_{(C≤12)}$;
a compound of the formula:

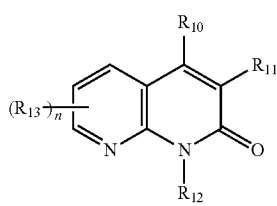

(III)

wherein:
$R_{10}$ is amino, hydroxy, or aryl$_{(C≤18)}$, aralkyl$_{(C≤18)}$, aryloxy$_{(C≤18)}$, cycloalkylamino$_{(C≤18)}$, aralkoxy$_{(C≤18)}$, arylamino$_{(C≤18)}$, aralkamino$_{(C≤18)}$, diarylamino$_{(C≤18)}$, diaralkamino$_{(C≤18)}$, or a substituted version of any of these groups;
$R_{11}$ is hydrogen, acyl$_{(C≤12)}$, or substituted acyl$_{(C≤12)}$, or —C(O)R$_a$; wherein:
  $R_a$ is amino, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤8)}$, or substituted dialkylamino$_{(C≤8)}$;
$R_{12}$ is hydrogen, alkoxy$_{(C≤8)}$, or substituted alkoxy$_{(C≤8)}$;
$R_{13}$ is amino, cyano, halo, hydroxy, nitro, alkyl$_{(C≤8)}$, substituted alkyl$_{(C≤8)}$, acyl$_{(C≤8)}$, substituted acyl$_{(C≤8)}$, alkoxy$_{(C≤8)}$, substituted alkoxy$_{(C≤8)}$, acyloxy$_{(C≤8)}$, substituted acyloxy$_{(C≤8)}$, alkylamino$_{(C≤8)}$, substituted alkylamino$_{(C≤8)}$, dialkylamino$_{(C≤8)}$, substituted dialkylamino$_{(C≤8)}$, amido$_{(C≤8)}$, or substituted amido$_{(C≤8)}$; and
n is 1, 2, or 3;
or a pharmaceutically acceptable salt or tautomer thereof.

In some embodiments, the compound is further defined as:

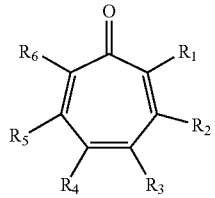

(I)

wherein:
$R_1$ and $R_6$ are each independently hydrogen, hydroxy, alkoxy$_{(C≤8)}$, substituted alkoxy$_{(C≤8)}$, acyloxy$_{(C≤8)}$, substituted acyloxy$_{(C≤8)}$, alkylamino$_{(C≤8)}$, substituted alkylamino$_{(C≤8)}$, dialkylamino$_{(C≤8)}$, substituted dialkylamino$_{(C≤8)}$, arylamino$_{(C≤8)}$, substituted arylamino$_{(C≤8)}$, diarylamino$_{(C≤8)}$, substituted diarylamino$_{(C≤8)}$, arylsulfonyloxy$_{(C≤8)}$, or substituted arylsulfonyloxy$_{(C≤8)}$;
$R_2$ and $R_5$ are each independently hydrogen, hydroxy, alkyl$_{(C≤12)}$, substituted alkyl$_{(C≤12)}$, cycloalkyl$_{(C≤12)}$, substituted cycloalkyl$_{(C≤12)}$, aryl$_{(C≤12)}$, substituted aryl$_{(C≤12)}$, aralkyl$_{(C≤12)}$, substituted aralkyl$_{(C≤12)}$, heteroaryl$_{(C≤12)}$, substituted heteroaryl$_{(C≤12)}$, alkoxy$_{(C≤12)}$, substituted alkoxy$_{(C≤12)}$, acyl$_{(C≤12)}$, or substituted acyl$_{(C≤12)}$; and
$R_3$ and $R_4$ are each independently hydrogen, hydroxy, nitroso, alkyl$_{(C≤12)}$, substituted alkyl$_{(C≤12)}$, cycloalkyl$_{(C≤12)}$, substituted cycloalkyl$_{(C≤12)}$, alkenyl$_{(C≤12)}$, substituted alkenyl$_{(C≤12)}$, aryl$_{(C≤18)}$, substituted aryl$_{(C≤18)}$, heteroaryl$_{(C≤8)}$, substituted heteroaryl$_{(C≤8)}$, acyl$_{(C≤12)}$, substituted acyl$_{(C≤12)}$, amido$_{(C≤12)}$, substituted amido$_{(C≤12)}$, or —C(O)R$_a$, wherein:
  $R_a$ is alkyl$_{(C≤18)}$, cycloalkyl$_{(C≤18)}$, aryl$_{(C≤18)}$, heteroaryl$_{(C≤18)}$, alkoxy$_{(C≤18)}$, aryloxy$_{(C≤18)}$, -alkanediyl$_{(C≤6)}$-cycloalkyl$_{(C≤12)}$; or a substituted version of any of these groups; or
$R_2$ and $R_3$ are taken together and are a compound of the formula:

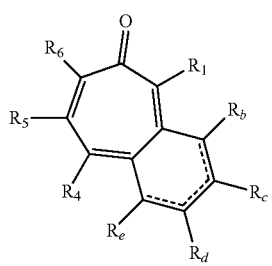

(IA)

wherein:
$R_b$, $R_c$, $R_d$, and $R_e$ are each independently hydrogen, hydroxy, or alkyl$_{(C≤8)}$, cycloalkyl$_{(C≤8)}$, alkenyl$_{(C≤8)}$, or a substituted version of any of these groups; or -alkanediyl$_{(C≤6)}$-alkylamino$_{(C≤8)}$, -alkane-diyl$_{(C≤6)}$-dialkylamino$_{(C≤8)}$, or a substituted version of either of these groups;

a compound of the formula:

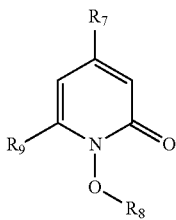

(II)

wherein:

R$_7$ is alkyl$_{(C≤12)}$, aryl$_{(C≤12)}$, aralkyl$_{(C≤12)}$, heteroaryl$_{(C≤12)}$, or a substituted version of any of these groups;

R$_8$ is hydrogen, alkyl$_{(C≤8)}$, or substituted alkyl$_{(C≤8)}$; and

R$_9$ is hydrogen, alkyl$_{(C≤12)}$, or substituted alkyl$_{(C≤12)}$;

a compound of the formula:

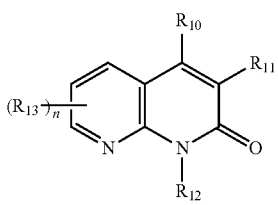

(III)

wherein:

R$_{10}$ is amino, hydroxy, or aryl$_{(C≤18)}$, aralkyl$_{(C≤18)}$, aryloxy$_{(C≤18)}$, cycloalkylamino$_{(C≤18)}$, aralkoxy$_{(C≤18)}$, arylamino$_{(C≤18)}$, aralkamino$_{(C≤18)}$, diarylamino$_{(C≤18)}$, diaralkamino$_{(C≤18)}$, or a substituted version of any of these groups;

R$_{11}$ is hydrogen, acyl$_{(C≤12)}$, or substituted acyl$_{(C≤12)}$, or —C(O)R$_a$; wherein:

R$_a$ is amino, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤8)}$, or substituted dialkylamino$_{(C≤8)}$;

R$_{12}$ is hydrogen, alkoxy$_{(C≤8)}$, or substituted alkoxy$_{(C≤8)}$;

R$_{13}$ is amino, cyano, halo, hydroxy, nitro, alkyl$_{(C≤8)}$, substituted alkyl$_{(C≤8)}$, acyl$_{(C≤8)}$, substituted acyl$_{(C≤8)}$, alkoxy$_{(C≤8)}$, substituted alkoxy$_{(C≤8)}$, acyloxy$_{(C≤8)}$, substituted acyloxy$_{(C≤8)}$, alkylamino$_{(C≤8)}$, substituted alkylamino$_{(C≤8)}$, dialkylamino$_{(C≤8)}$, substituted dialkylamino$_{(C≤8)}$, amido$_{(C≤8)}$, or substituted amido$_{(C≤8)}$; and n is 1, 2, or 3;

or a pharmaceutically acceptable salt or tautomer thereof.

In yet another aspect, the present disclosure provides pharmaceutical compositions comprising:

(A) a compound of the formula:

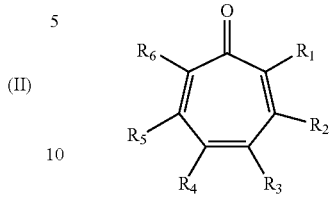

(I)

wherein:

R$_1$ and R$_6$ are each independently hydrogen, halo, or a group of the formula:

—X—Y$_1$, wherein:

X is C(O), O, S, or NR$_1$', wherein:

R$_1$' is hydrogen, alkyl$_{(C≤8)}$, substituted alkyl$_{(C≤8)}$, aryl$_{(C≤8)}$, or substituted aryl$_{(C≤8)}$; and Y$_1$ is hydrogen, hydroxy, or alkyl$_{(C≤12)}$, aryl$_{(C≤12)}$, acyl$_{(C≤12)}$, alkoxy$_{(C≤12)}$, alkylsulfonyl$_{(C≤12)}$, arylsulfonyl$_{(C≤12)}$, or a substituted version of any of these groups;

R$_2$ and R$_5$ are each independently hydrogen, hydroxy, halo, alkyl$_{(C≤12)}$, substituted alkyl$_{(C≤12)}$, cycloalkyl$_{(C≤12)}$, substituted cycloalkyl$_{(C≤12)}$, alkenyl$_{(C≤12)}$, substituted alkenyl$_{(C≤12)}$, aryl$_{(C≤12)}$, substituted aryl$_{(C≤12)}$, aralkyl$_{(C≤12)}$, substituted aralkyl$_{(C≤12)}$, heteroaryl$_{(C≤12)}$, substituted heteroaryl$_{(C≤12)}$, alkoxy$_{(C≤12)}$, substituted alkoxy$_{(C≤12)}$, acyl$_{(C≤12)}$, substituted acyl$_{(C≤12)}$, or a group of the formula: —C(O)Y$_2$R$_2$', wherein:

Y$_2$ is alkenediyl$_{(C≤8)}$ or substituted alkenediyl$_{(C≤8)}$; and

R$_2$' is aryl$_{(C≤12)}$, heteroaryl$_{(C≤12)}$, arenediyl$_{(C≤12)}$-O-aryl$_{(C≤12)}$, or a substituted version of any of these groups; and R$_3$ and R$_4$ are each independently hydrogen, hydroxy, halo, nitroso, alkyl$_{(C≤12)}$, substituted alkyl$_{(C≤12)}$, cycloalkyl$_{(C≤12)}$, substituted cycloalkyl$_{(C≤12)}$, alkenyl$_{(C≤12)}$, substituted alkenyl$_{(C≤12)}$, aryl$_{(C≤18)}$, substituted aryl$_{(C≤18)}$, heteroaryl$_{(C≤18)}$, substituted heteroaryl$_{(C≤18)}$, acyl$_{(C≤18)}$, substituted acyl$_{(C≤18)}$, amido$_{(C≤18)}$, substituted amido$_{(C≤18)}$, or —C(O)R$_a$ or —S(O)$_2$R$_a$ wherein:

R$_a$ is alkyl$_{(C≤18)}$, cycloalkyl$_{(C≤18)}$, aryl$_{(C≤18)}$, heteroaryl$_{(C≤18)}$, alkoxy$_{(C≤18)}$, aryloxy$_{(C≤18)}$, -alkanediyl$_{(C≤6)}$-cycloalkyl$_{(C≤12)}$; or a substituted version of any of these groups; or R$_2$ and R$_3$ are taken together and are a compound of the formula:

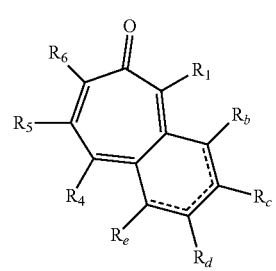

(IA)

wherein:
$R_b$, $R_c$, $R_d$, and $R_e$ are each independently hydrogen, hydroxy, or alkyl$_{(C\leq 8)}$, cycloalkyl$_{(C\leq 8)}$, alkenyl$_{(C\leq 8)}$, or a substituted version of any of these groups; or -alkanediyl$_{(C\leq 6)}$-alkylamino$_{(C\leq 8)}$, -alkane-diyl$_{(C\leq 6)}$-dialkylamino$_{(C\leq 8)}$, or a substituted version of either of these groups; or
$R_1$ and $R_2$ are taken together and are a compound of the formula:

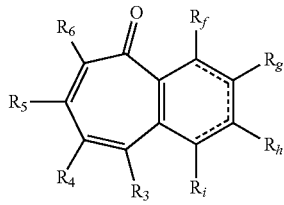

(IB)

wherein:
$R_f$, $R_g$, $R_h$, and $R_i$ are each independently hydrogen, hydroxy, or alkyl$_{(C\leq 8)}$, cycloalkyl$_{(C\leq 8)}$, alkenyl$_{(C\leq 8)}$, or a substituted version of any of these groups; or -alkanediyl$_{(C\leq 6)}$-alkylamino$_{(C\leq 8)}$, -alkanediyl$_{(C\leq 6)}$-dialkylamino$_{(C\leq 8)}$, or a substituted version of either of these groups; or
$R_3$ and $R_4$ are taken together and are a compound of the formula:

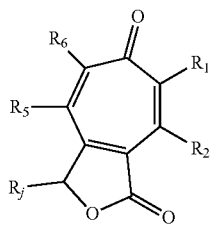

(IC)

wherein:
$R_j$ is hydrogen, hydroxy, halo, or alkyl$_{(C\leq 8)}$, cycloalkyl$_{(C\leq 8)}$, alkenyl$_{(C\leq 8)}$, or a substituted version of any of these groups; or -alkanediyl$_{(C\leq 6)}$-alkylamino$_{(C\leq 8)}$, -alkanediyl$_{(C\leq 6)}$-dialkylamino$_{(C\leq 8)}$, or a substituted version of either of these groups; or
a compound of the formula:

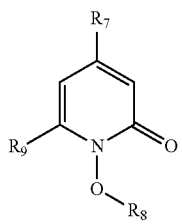

(II)

wherein:
$R_7$ is alkyl$_{(C\leq 12)}$, aryl$_{(C\leq 12)}$, aralkyl$_{(C\leq 12)}$, heteroaryl$_{(C\leq 12)}$, or a substituted version of any of these groups;

$R_8$ is hydrogen, alkyl$_{(C\leq 8)}$, or substituted alkyl$_{(C\leq 8)}$; and
$R_9$ is hydrogen, alkyl$_{(C\leq 12)}$, or substituted alkyl$_{(C\leq 12)}$;
a compound of the formula:

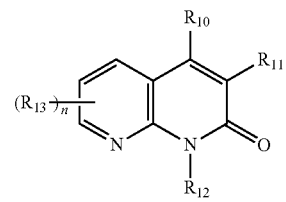

(III)

wherein:
$R_{10}$ is amino, hydroxy, or aryl$_{(C\leq 18)}$, aralkyl$_{(C\leq 18)}$, aryloxy$_{(C\leq 18)}$, cycloalkylamino$_{(C\leq 18)}$, aralkoxy$_{(C\leq 18)}$, arylamino$_{(C\leq 18)}$, aralkamino$_{(C\leq 18)}$, diarylamino$_{(C\leq 18)}$, diaralkamino$_{(C\leq 18)}$, or a substituted version of any of these groups;
$R_{11}$ is hydrogen, acyl$_{(C\leq 12)}$, or substituted acyl$_{(C\leq 12)}$, or —C(O)R$_a$; wherein:
$R_a$ is amino, hydroxy, alkoxy$_{(C\leq 8)}$, substituted alkoxy$_{(C\leq 8)}$, alkylamino$_{(C\leq 8)}$, substituted alkylamino$_{(C\leq 8)}$, dialkylamino$_{(C\leq 8)}$, or substituted dialkylamino$_{(C\leq 8)}$;
$R_{12}$ is hydrogen, alkoxy$_{(C\leq 8)}$, or substituted alkoxy$_{(C\leq 8)}$;
$R_{13}$ is amino, cyano, halo, hydroxy, nitro, alkyl$_{(C\leq 8)}$, substituted alkyl$_{(C\leq 8)}$, acyl$_{(C\leq 8)}$, substituted acyl$_{(C\leq 8)}$, alkoxy$_{(C\leq 8)}$, substituted alkoxy$_{(C\leq 8)}$, acyloxy$_{(C\leq 8)}$, substituted acyloxy$_{(C\leq 8)}$, alkylamino$_{(C\leq 8)}$, substituted alkylamino$_{(C\leq 8)}$, dialkylamino$_{(C\leq 8)}$, substituted dialkylamino$_{(C\leq 8)}$, amido$_{(C\leq 8)}$, or substituted amido$_{(C\leq 8)}$; and
n is 1, 2, or 3;
or a pharmaceutically acceptable salt or tautomer thereof; and
(B) a second anti-fungal compound.
In some embodiments, the compound is further defined as:

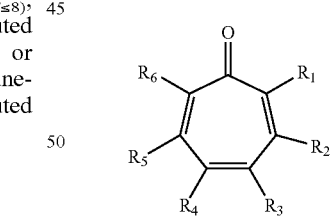

(I)

wherein:
$R_1$ and $R_6$ are each independently hydrogen, halo, or a group of the formula: —X—Y$_1$, wherein:
X is O, S, or NR$_1$', wherein:
$R_1$' is hydrogen, alkyl$_{(C\leq 8)}$, substituted alkyl$_{(C\leq 8)}$, aryl$_{(C\leq 8)}$, or substituted aryl$_{(C\leq 8)}$; and
$Y_1$ is hydrogen or alkyl$_{(C\leq 12)}$, aryl$_{(C\leq 12)}$, acyl$_{(C\leq 12)}$, alkylsulfonyl$_{(C\leq 12)}$, arylsulfonyl$_{(C\leq 12)}$, or a substituted version of any of these groups;
$R_2$ and $R_5$ are each independently hydrogen, hydroxy, halo, alkyl$_{(C\leq 12)}$, substituted alkyl$_{(C\leq 12)}$, cycloalkyl$_{(C\leq 12)}$, substituted cycloalkyl$_{(C\leq 12)}$, aryl$_{(C\leq 12)}$, substituted aryl$_{(C\leq 12)}$, aralkyl$_{(C\leq 12)}$, substituted aralkyl$_{(C≤12)}$, heteroaryl$_{(C≤12)}$, substituted heteroaryl$_{(C≤12)}$, alkoxy$_{(C≤12)}$, substituted alkoxy$_{(C≤12)}$, acyl$_{(C≤12)}$, or substituted acyl$_{(C≤12)}$; and $R_3$ and $R_4$ are each independently hydrogen, hydroxy, halo, nitroso, alkyl$_{(C≤12)}$, substituted alkyl$_{(C≤12)}$, cycloalkyl$_{(C≤12)}$, substituted cycloalkyl$_{(C≤12)}$, alkenyl$_{(C≤12)}$, substituted alkenyl$_{(C≤12)}$, aryl$_{(C≤18)}$, substituted aryl$_{(C≤18)}$, heteroaryl$_{(C≤18)}$, substituted heteroaryl$_{(C≤18)}$, acyl$_{(C≤18)}$, substituted acyl$_{(C≤18)}$, amido$_{(C≤18)}$, substituted amido$_{(C≤18)}$, or —C(O)R$_a$, wherein:

$R_a$ is alkyl$_{(C≤18)}$, cycloalkyl$_{(C≤18)}$, aryl$_{(C≤18)}$, heteroaryl$_{(C≤18)}$, alkoxy$_{(C≤8)}$, aryloxy$_{(C≤18)}$, -alkanediyl$_{(C≤6)}$-cycloalkyl$_{(C≤12)}$; or a substituted version of any of these groups; or $R_2$ and $R_3$ are taken together and are a compound of the formula:

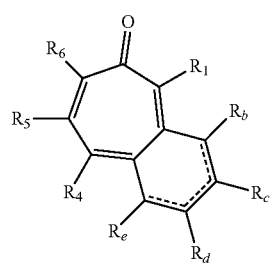

(IA)

wherein:
$R_b$, $R_c$, $R_d$, and $R_e$ are each independently hydrogen, hydroxy, or alkyl$_{(C≤8)}$, cycloalkyl$_{(C≤8)}$, alkenyl$_{(C≤8)}$, or a substituted version of any of these groups; or -alkanediyl$_{(C≤6)}$-alkylamino$_{(C≤8)}$, -alkanediyl$_{(C≤6)}$-dialkylamino$_{(C≤8)}$, or a substituted version of either of these groups; or $R_1$ and $R_2$ are taken together and are a compound of the formula:

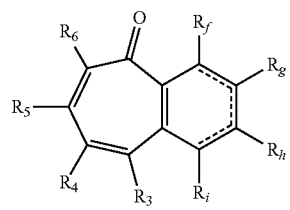

(IB)

wherein:
$R_f$, $R_g$, $R_h$, and $R_i$ are each independently hydrogen, hydroxy, or alkyl$_{(C≤8)}$, cycloalkyl$_{(C≤8)}$, alkenyl$_{(C≤8)}$, or a substituted version of any of these groups; or -alkanediyl$_{(C≤6)}$-alkylamino$_{(C≤8)}$, -alkane-diyl$_{(C≤6)}$-dialkylamino$_{(C≤8)}$, or a substituted version of either of these groups; or $R_3$ and $R_4$ are taken together and are a compound of the formula:

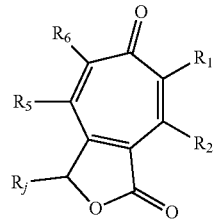

(IC)

wherein:
$R_j$ is hydrogen, hydroxy, halo, or alkyl$_{(C≤8)}$, cycloalkyl$_{(C≤8)}$, alkenyl$_{(C≤8)}$, or a substituted version of any of these groups; or -alkanediyl$_{(C≤6)}$-alkylamino$_{(C≤8)}$, -alkane-diyl$_{(C≤6)}$-dialkylamino$_{(C≤8)}$, or a substituted version of either of these groups; or a compound of the formula:

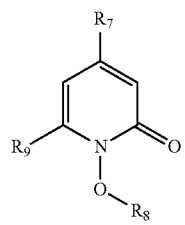

(II)

wherein:
$R_7$ is alkyl$_{(C≤12)}$, aryl$_{(C≤12)}$, aralkyl$_{(C≤12)}$, heteroaryl$_{(C≤12)}$, or a substituted version of any of these groups;

$R_8$ is hydrogen, alkyl$_{(C≤8)}$, or substituted alkyl$_{(C≤8)}$; and $R_9$ is hydrogen, alkyl$_{(C≤12)}$, or substituted alkyl$_{(C≤12)}$;

a compound of the formula:

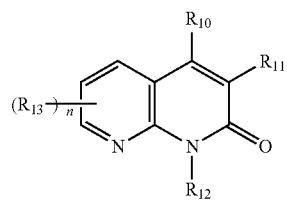

(III)

wherein:
$R_{10}$ is amino, hydroxy, or aryl$_{(C≤18)}$, aralkyl$_{(C≤18)}$, aryloxy$_{(C≤18)}$, cycloalkylamino$_{(C≤18)}$, aralkoxy$_{(C≤18)}$, arylamino$_{(C≤18)}$, aralkamino$_{(C≤18)}$, diarylamino$_{(C≤18)}$, diaralkamino$_{(C≤18)}$, or a substituted version of any of these groups;

$R_{11}$ is hydrogen, acyl$_{(C≤12)}$, or substituted acyl$_{(C≤12)}$, or —C(O)R$_a$; wherein:

$R_a$ is amino, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤8)}$, or substituted dialkylamino$_{(C≤8)}$;

$R_{12}$ is hydrogen, alkoxy$_{(C≤8)}$, or substituted alkoxy$_{(C≤8)}$;

$R_{13}$ is amino, cyano, halo, hydroxy, nitro, alkyl$_{(C≤8)}$, substituted alkyl$_{(C≤8)}$, acyl$_{(C≤8)}$, substituted acyl$_{(C\leq8)}$, alkoxy$_{(C\leq8)}$, substituted alkoxy$_{(C\leq8)}$, acyloxy$_{(C\leq8)}$, substituted acyloxy$_{(C\leq8)}$, alkylamino$_{(C\leq8)}$, substituted alkylamino$_{(C\leq8)}$, dialkylamino$_{(C\leq8)}$, substituted dialkylamino$_{(C\leq8)}$, amido$_{(C\leq8)}$, or substituted amido$_{(C\leq8)}$; and n is 1, 2, or 3;

or a pharmaceutically acceptable salt or tautomer thereof.

In some embodiments, the second anti-fungal compound is Amphotericin B, an azole anti-fungal compound, flucytosine, or echinocandins. In some embodiments, the azole anti-fungal compound is fluconazole, itraconazole, posaconazole, or voriconazole. In some embodiments, the pharmaceutical compositions are formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularly, intravitreally, liposomally, locally, mucosally, parenterally, rectally, subconjunctivally, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion. In some embodiments, the pharmaceutical compositions are formulated for oral administration or intravenous administration. In some embodiments, the pharmaceutical compositions are formulated as a unit dose.

In still yet another aspect, the present disclosure provides methods of inhibiting the growth of a fungus comprising contacting the fungus with an effective amount of a compound of the formula:

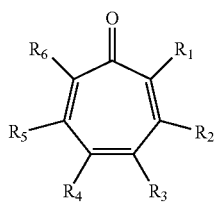

(I)

wherein:

$R_1$ and $R_6$ are each independently hydrogen, halo, or a group of the formula: —X—Y$_1$, wherein:

X is C(O), O, S, or NR$_1$', wherein:

R$_1$' is hydrogen, alkyl$_{(C\leq8)}$, substituted alkyl$_{(C\leq8)}$, aryl$_{(C\leq8)}$, or substituted aryl$_{(C\leq8)}$; and Y$_1$ is hydrogen, hydroxy, or alkyl$_{(C\leq12)}$, aryl$_{(C\leq12)}$, acyl$_{(C\leq12)}$, alkoxy$_{(C\leq12)}$, alkylsulfonyl$_{(C\leq12)}$, arylsulfonyl$_{(C\leq12)}$, or a substituted version of any of these groups;

R$_2$ and R$_5$ are each independently hydrogen, hydroxy, halo, alkyl$_{(C\leq12)}$, substituted alkyl$_{(C\leq12)}$, cycloalkyl$_{(C\leq12)}$, substituted cycloalkyl$_{(C\leq12)}$, alkenyl$_{(C\leq12)}$, substituted alkenyl$_{(C\leq12)}$, aryl$_{(C\leq12)}$, substituted aryl$_{(C\leq12)}$, aralkyl$_{(C\leq12)}$, substituted aralkyl$_{(C\leq12)}$, heteroaryl$_{(C\leq12)}$, substituted heteroaryl$_{(C\leq12)}$, alkoxy$_{(C\leq12)}$, substituted alkoxy$_{(C\leq12)}$, acyl$_{(C\leq12)}$, substituted acyl$_{(C\leq12)}$, or a group of the formula: —C(O)Y$_2$R$_2$', wherein:

Y$_2$ is alkenediyl$_{(C\leq8)}$ or substituted alkenediyl$_{(C\leq8)}$; and

R$_2$' is aryl$_{(C\leq12)}$, heteroaryl$_{(C\leq12)}$, arenediyl$_{(C\leq12)}$-O-aryl$_{(C\leq12)}$, or a substituted version of any of these groups; and R$_3$ and R$_4$ are each independently hydrogen, hydroxy, halo, nitroso, alkyl$_{(C\leq12)}$, substituted alkyl$_{(C\leq12)}$, cycloalkyl$_{(C\leq12)}$, substituted cycloalkyl$_{(C\leq12)}$, alkenyl$_{(C\leq12)}$, substituted alkenyl$_{(C\leq12)}$, aryl$_{(C\leq18)}$, substituted aryl$_{(C\leq18)}$, heteroaryl$_{(C\leq18)}$, substituted heteroaryl$_{(C\leq18)}$, acyl$_{(C\leq18)}$, substituted acyl$_{(C\leq18)}$, amido$_{(C\leq18)}$, substituted amido$_{(C\leq18)}$, or —C(O)R$_a$ or —S(O)$_2$R$_a$ wherein:

R$_a$ is alkyl$_{(C\leq18)}$, cycloalkyl$_{(C\leq18)}$, aryl$_{(C\leq18)}$, heteroaryl$_{(C\leq18)}$, alkoxy$_{(C\leq18)}$, aryloxy$_{(C\leq18)}$, -alkanediyl$_{(C\leq6)}$-cycloalkyl$_{(C\leq12)}$; or a substituted version of any of these groups; or R$_2$ and R$_3$ are taken together and are a compound of the formula:

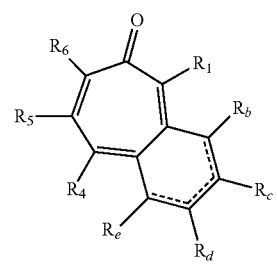

(IA)

wherein:

R$_b$, R$_c$, R$_d$, and R$_e$ are each independently hydrogen, hydroxy, or alkyl$_{(C\leq8)}$, cycloalkyl$_{(C\leq8)}$, alkenyl$_{(C\leq8)}$, or a substituted version of any of these groups; or -alkanediyl$_{(C\leq6)}$-alkylamino$_{(C\leq8)}$, -alkanediyl$_{(C\leq6)}$-dialkylamino$_{(C\leq8)}$, or a substituted version of either of these groups; or R$_1$ and R$_2$ are taken together and are a compound of the formula:

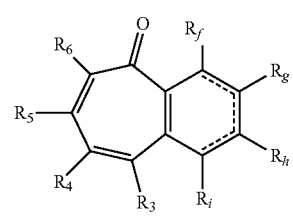

(IB)

wherein:

R$_f$, R$_g$, R$_h$, and R$_i$ are each independently hydrogen, hydroxy, or alkyl$_{(C\leq8)}$, cycloalkyl$_{(C\leq8)}$, alkenyl$_{(C\leq8)}$, or a substituted version of any of these groups; or -alkanediyl$_{(C\leq6)}$-alkylamino$_{(C\leq8)}$, -alkane-diyl$_{(C\leq6)}$-dialkylamino$_{(C\leq8)}$, or a substituted version of either of these groups; or R$_3$ and R$_4$ are taken together and are a compound of the formula:

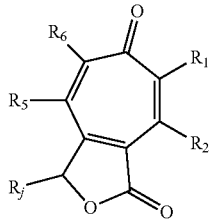

(IC)

wherein:
R_j is hydrogen, hydroxy, halo, or alkyl$_{(C≤8)}$, cycloalkyl$_{(C≤8)}$, alkenyl$_{(C≤8)}$, or a substituted version of any of these groups; or -alkanediyl$_{(C≤6)}$-alkylamino$_{(C≤8)}$, -alkane-diyl$_{(C≤6)}$-dialkylamino$_{(C≤8)}$, or a substituted version of either of these groups;
or
a compound of the formula:

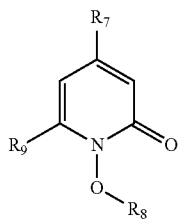

(II)

wherein:
R_7 is alkyl$_{(C≤12)}$, aryl$_{(C≤12)}$, aralkyl$_{(C≤12)}$, heteroaryl$_{(C≤12)}$, or a substituted version of any of these groups;
R_8 is hydrogen, alkyl$_{(C≤8)}$, or substituted alkyl$_{(C≤8)}$; and
R_9 is hydrogen, alkyl$_{(C≤12)}$, or substituted alkyl$_{(C≤12)}$;
a compound of the formula:

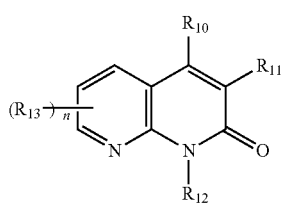

(III)

wherein:
R_10 is amino, hydroxy, or aryl$_{(C≤18)}$, aralkyl$_{(C≤18)}$, aryloxy$_{(C≤18)}$, cycloalkylamino$_{(C≤18)}$, aralkoxy$_{(C≤18)}$, arylamino$_{(C≤18)}$, aralkamino$_{(C≤18)}$, diarylamino$_{(C≤18)}$, diaralkamino$_{(C≤18)}$, or a substituted version of any of these groups;
R_11 is hydrogen, acyl$_{(C≤12)}$, or substituted acyl$_{(C≤12)}$, or —C(O)R_a; wherein:
R_a is amino, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤8)}$, or substituted dialkylamino$_{(C≤8)}$;
R_12 is hydrogen, alkoxy$_{(C≤8)}$, or substituted alkoxy$_{(C≤8)}$;
R_13 is amino, cyano, halo, hydroxy, nitro, alkyl$_{(C≤8)}$, substituted alkyl$_{(C≤8)}$, acyl$_{(C≤8)}$, substituted acyl$_{(C≤8)}$, alkoxy$_{(C≤8)}$, substituted alkoxy$_{(C≤8)}$, acyloxy$_{(C≤8)}$, substituted acyloxy$_{(C≤8)}$, alkylamino$_{(C≤8)}$, substituted alkylamino$_{(C≤8)}$, dialkylamino$_{(C≤8)}$, substituted dialkylamino$_{(C≤8)}$, amido$_{(C≤8)}$, or substituted amido$_{(C≤8)}$; and
n is 1, 2, or 3;
or a pharmaceutically acceptable salt or tautomer thereof;
In some embodiments, the compound is further defined as:

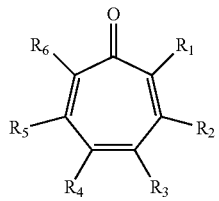

(I)

wherein:
R_1 and R_6 are each independently hydrogen, hydroxy, alkoxy$_{(C≤8)}$, substituted alkoxy$_{(C≤8)}$, acyloxy$_{(C≤8)}$, substituted acyloxy$_{(C≤8)}$, alkylamino$_{(C≤8)}$, substituted alkylamino$_{(C≤8)}$, dialkylamino$_{(C≤8)}$, substituted dialkylamino$_{(C≤8)}$, arylamino$_{(C≤8)}$, substituted arylamino$_{(C≤8)}$, diarylamino$_{(C≤8)}$, substituted diarylamino$_{(C≤8)}$, arylsulfonyloxy$_{(C≤8)}$, or substituted arylsulfonyloxy$_{(C≤8)}$;
R_2 and R_5 are each independently hydrogen, hydroxy, alkyl$_{(C≤12)}$, substituted alkyl$_{(C≤12)}$, cycloalkyl$_{(C≤12)}$, substituted cycloalkyl$_{(C≤12)}$, aryl$_{(C≤12)}$, substituted aryl$_{(C≤12)}$, aralkyl$_{(C≤12)}$, substituted aralkyl$_{(C≤12)}$, heteroaryl$_{(C≤12)}$, substituted heteroaryl$_{(C≤12)}$, alkoxy$_{(C≤12)}$, substituted alkoxy$_{(C≤12)}$, acyl$_{(C≤12)}$, or substituted acyl$_{(C≤12)}$; and
R_3 and R_4 are each independently hydrogen, hydroxy, nitroso, alkyl$_{(C≤12)}$, substituted alkyl$_{(C≤12)}$, cycloalkyl$_{(C≤12)}$, substituted cycloalkyl$_{(C≤12)}$, alkenyl$_{(C≤12)}$, substituted alkenyl$_{(C≤12)}$, aryl$_{(C≤18)}$, substituted aryl$_{(C≤18)}$, heteroaryl$_{(C≤8)}$, substituted heteroaryl$_{(C≤8)}$, acyl$_{(C≤12)}$, substituted acyl$_{(C≤12)}$, amido$_{(C≤12)}$, substituted amido$_{(C≤12)}$, or —C(O)R_a,
wherein:
R_a is alkyl$_{(C≤18)}$, cycloalkyl$_{(C≤18)}$, aryl$_{(C≤18)}$, heteroaryl$_{(C≤18)}$, alkoxy$_{(C≤18)}$, aryloxy$_{(C≤18)}$, -alkanediyl$_{(C≤6)}$-cycloalkyl$_{(C≤12)}$; or a substituted version of any of these groups; or
R_2 and R_3 are taken together and are a compound of the formula:

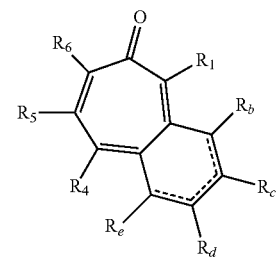

(IA)

wherein:
R_b, R_c, R_d, and R_e are each independently hydrogen, hydroxy, or alkyl$_{(C≤8)}$, cycloalkyl$_{(C≤8)}$, alkenyl$_{(C≤8)}$, or a substituted version of any of these groups; or -alkanediyl$_{(C≤6)}$-alkylamino$_{(C≤8)}$, -alkane-diyl$_{(C≤6)}$-dialkylamino$_{(C≤8)}$, or a substituted version of either of these groups;

a compound of the formula:

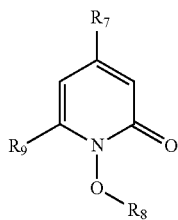

(II)

wherein:
R$_7$ is alkyl$_{(C≤12)}$, aryl$_{(C≤12)}$, aralkyl$_{(C≤12)}$, heteroaryl$_{(C≤12)}$, or a substituted version of any of these groups;
R$_8$ is hydrogen, alkyl$_{(C≤8)}$, or substituted alkyl$_{(C≤8)}$; and
R$_9$ is hydrogen, alkyl$_{(C≤12)}$, or substituted alkyl$_{(C≤12)}$;
a compound of the formula:

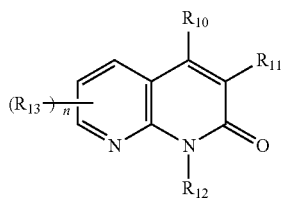

(III)

wherein:
R$_{10}$ is amino, hydroxy, or aryl$_{(C≤18)}$, aralkyl$_{(C≤18)}$, aryloxy$_{(C≤18)}$, cycloalkylamino$_{(C≤18)}$, aralkoxy$_{(C≤18)}$, arylamino$_{(C≤18)}$, aralkamino$_{(C≤18)}$, diarylamino$_{(C≤18)}$, diaralkamino$_{(C≤18)}$, or a substituted version of any of these groups;
R$_{11}$ is hydrogen, acyl$_{(C≤12)}$, or substituted acyl$_{(C≤12)}$, or —C(O)R$_a$; wherein:
  R$_a$ is amino, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤8)}$, or substituted dialkylamino$_{(C≤8)}$;
R$_{12}$ is hydrogen, alkoxy$_{(C≤8)}$, or substituted alkoxy$_{(C≤8)}$;
R$_{13}$ is amino, cyano, halo, hydroxy, nitro, alkyl$_{(C≤8)}$, substituted alkyl$_{(C≤8)}$, acyl$_{(C≤8)}$, substituted acyl$_{(C≤8)}$, alkoxy$_{(C≤8)}$, substituted alkoxy$_{(C≤8)}$, acyloxy$_{(C≤8)}$, substituted acyloxy$_{(C≤8)}$, alkylamino$_{(C≤8)}$, substituted alkylamino$_{(C≤8)}$, dialkylamino$_{(C≤8)}$, substituted dialkylamino$_{(C≤8)}$, amido$_{(C≤8)}$, or substituted amido$_{(C≤8)}$; and
n is 1, 2, or 3;
or a pharmaceutically acceptable salt or tautomer thereof.

In some embodiments, the compound is cytostatic. In some embodiments, the compound inhibits growth by more than 50% at a concentration of less than 50 µM.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects, or +/−5% of the stated value.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 5B) YNB-02 at 35° C.

FIGS. 8C-8F show the agar plates treated with 2×, 4×, and 8×MIC of FLC (FIG. 8C), AmB (FIG. 8D), Compound #54 (FIG. 8E), and Compound #284 (FIG. 8F).

DETAILED DESCRIPTION

Figure 1:
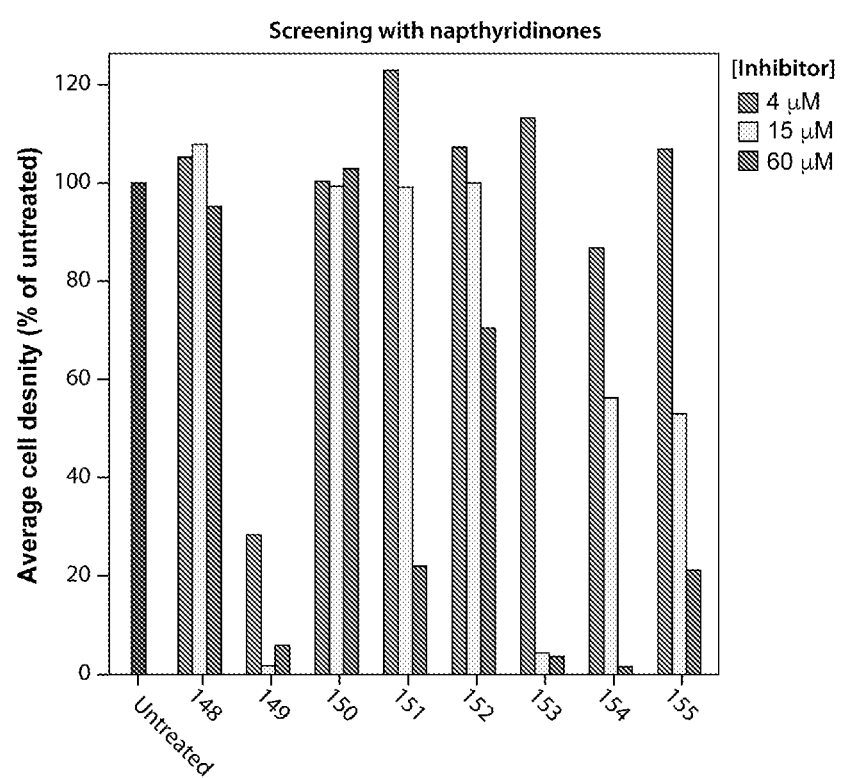
FIG. 1. Results from screening 8 napthyridinone derivatives. Wild-type KN99α at a starting density of 0.0005 was treated with the compounds at 4 µM, 15 µM, and 60 µM in nutrient-limiting media (YNB, pH 7)+1% DMSO at 35° C. for 48 hours. Bars represent the average cell density of at least three replicates as percent of untreated cells. 5 of the 8 compounds inhibited growth at least 75% relative to untreated controls.
Figure 2:
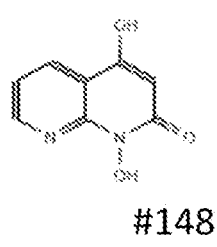
FIG. 2. Structures of compounds #148-155.
Figure 2:
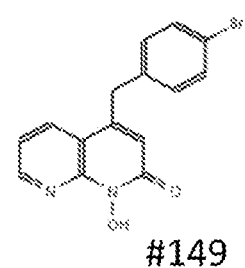
Figure 2:
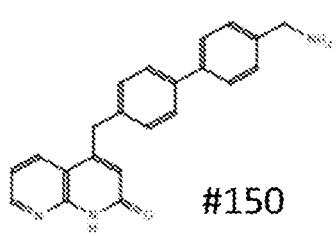
Figure 2:
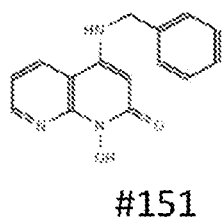
Figure 2:
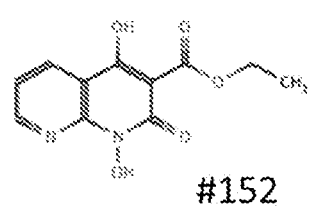
Figure 2:
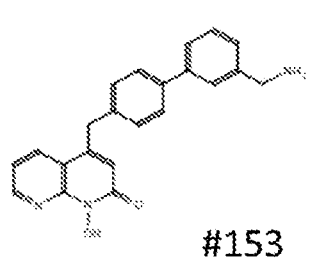
Figure 2:
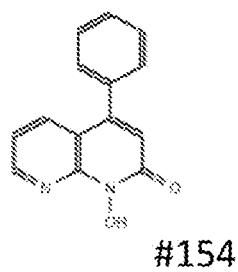
Figure 2:
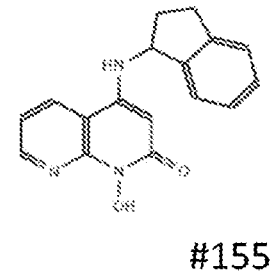

The present disclosure provides compounds which may be used to treat a pathogenic fungal infection such as an infection of C. neoformans. The compounds provided herein may also be used in combination with other known antifungal therapies for the treatment of a fungal infection. The compounds described herein may be used in the treatment of a fungal infection in an immunocompromised patient.

A. Fungal Infections

Fungi are plentiful, with about 1.5 million different species on earth. Only about 300 of these are known to cause disease. Fungal diseases are called mycoses and those affecting humans can be divided into four groups based on the level of penetration into the body tissues. Superficial mycoses are caused by fungi that grow on the surface of the skin or hair. Cutaneous mycoses or dermatomycoses include such infections as athlete's foot and ringworm, where growth occurs only in the superficial layers of skin, nails, or hair. Subcutaneous mycoses penetrate below the skin to involve the subcutaneous, connective, and bone tissue. Systemic or deep mycoses are able to infect internal organs and become widely disseminated throughout the body. This type is often fatal.

Some of the more common diseases include Aspergillosis, Blastomycosis, Candidiasis, Coccidioidomycosis, *C. neoformans* infection, *C. gattii* infection, fungal eye infection, Histoplasmosis, Mucormycosis, *Pneumocystis* pneumonia, Ringworm and Sportotrichosis. Candidemia infections occur can be predicted at around 300,000 worldwide per year—with a mortality of 30-55%. Invasive aspergillosis can occur in different patients groups—so around 10% of new leukaemic cases will go on to develop invasive aspergillosis—so 30,000 per year. Of stem cell transplants—54,000 are carried out in USA, UK, Europe and Japan annually, of which 5,400 will need treatment for *aspergillus* infection. In chronic obstructive pulmonary disease—1.2% of these will need antifungals for aspergillosis—216,000 per year. Over 50% of invasive aspergillosis patients will die from their infection—even with treatment. In AIDS patients 1 million contract cryptococcal meningitis resulting in 600,000 deaths—70% of which are in sub-saharan Africa. Less fatal infections but which affect large numbers of people worldwide include cutaneous fungal infections, nail infections and athletes foot—affects some 1.5 billion people—or 25% of the world's population. Tinea capitis—or hair infection—which is common in young children is predicted to affect some 200 million worldwide.

Fungi that may be treated in accordance with the present disclosure include, e.g., *Candida* spp. including *C. albicans, C. tropicalis, C. kerr, C. krusei* and *C. galbrata; Aspergillus* spp. including *A. fumigatus* and *A. flavus; Cryptococcus neofornans; Blastomyces* spp. including *Blastomyces dermatitidis; Pneumocystis carinii; Coccidioides immitis; Basidiobolus ranarum; Conidiobolus* spp.; *Histoplasma capsulatum; Rhizopus* spp. including *R. oryzae* and *R. microsporus; Cunninghamella* spp.; *Zygomycetes* such as *Rhizomucor* spp. (*R. oryzae, R. microspores*); *Paracoccidioides brasiliensis; Pseudallescheria boydii; Rhinosporidium seeberi;* and *Sporothrix schenckii.*

B. Chemical Entity

The compounds of the present disclosure are represented by the formula below:

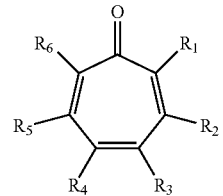

(I)

wherein:
$R_1$ and $R_6$ are each independently hydrogen, halo, or a group of the formula:

—X—$Y_1$, wherein:

X is C(O), O, S, or $NR_1'$, wherein:
$R_1'$ is hydrogen, alkyl$_{(C\leq 8)}$, substituted alkyl$_{(C\leq 8)}$, aryl$_{(C\leq 8)}$, or substituted aryl$_{(C\leq 8)}$; and $Y_1$ is hydrogen, hydroxy, or alkyl$_{(C\leq 12)}$, aryl$_{(C\leq 12)}$, acyl$_{(C\leq 12)}$, alkoxy$_{(C\leq 12)}$, alkylsulfonyl$_{(C\leq 12)}$, arylsulfonyl$_{(C\leq 12)}$, or a substituted version of any of these groups;

$R_2$ and $R_5$ are each independently hydrogen, hydroxy, halo, alkyl$_{(C\leq 12)}$, substituted alkyl$_{(C\leq 12)}$, cycloalkyl$_{(C\leq 12)}$, substituted cycloalkyl$_{(C\leq 12)}$, alkenyl$_{(C\leq 12)}$, substituted alkenyl$_{(C\leq 12)}$, aryl$_{(C\leq 12)}$, substituted aryl$_{(C\leq 12)}$, aralkyl$_{(C\leq 12)}$, substituted aralkyl$_{(C\leq 12)}$, heteroaryl$_{(C\leq 12)}$, substituted heteroaryl$_{(C\leq 12)}$, alkoxy$_{(C\leq 12)}$, substituted alkoxy$_{(C\leq 12)}$, acyl$_{(C\leq 12)}$, substituted acyl$_{(C\leq 12)}$, or a group of the formula: —C(O)$Y_2R_2'$, wherein:

$Y_2$ is alkenediyl$_{(C\leq 8)}$ or substituted alkenediyl$_{(C\leq 8)}$; and $R_2'$ is aryl$_{(C\leq 12)}$, heteroaryl$_{(C\leq 12)}$, arenediyl$_{(C\leq 12)}$-O-aryl$_{(C\leq 12)}$, or a substituted version of any of these groups; and $R_3$ and $R_4$ are each independently hydrogen, hydroxy, halo, nitroso, alkyl$_{(C\leq 12)}$, substituted alkyl$_{(C\leq 12)}$, cycloalkyl$_{(C\leq 12)}$, substituted cycloalkyl$_{(C\leq 12)}$, alkenyl$_{(C\leq 12)}$, substituted alkenyl$_{(C\leq 12)}$, aryl$_{(C\leq 18)}$, substituted aryl$_{(C\leq 18)}$, heteroaryl$_{(C\leq 18)}$, substituted heteroaryl$_{(C\leq 18)}$, acyl$_{(C\leq 8)}$, substituted acyl$_{(C\leq 18)}$, amido$_{(C\leq 18)}$, substituted amido$_{(C\leq 18)}$, or —C(O)$R_a$ or —S(O)$_2R_a$ wherein:

$R_a$ is alkyl$_{(C\leq 18)}$, cycloalkyl$_{(C\leq 18)}$, aryl$_{(C\leq 18)}$, heteroaryl$_{(C\leq 18)}$, alkoxy$_{(C\leq 18)}$, aryloxy$_{(C\leq 18)}$, -alkanediyl$_{(C\leq 6)}$-cycloalkyl$_{(C\leq 12)}$; or a substituted version of any of these groups; or $R_2$ and $R_3$ are taken together and are a compound of the formula:

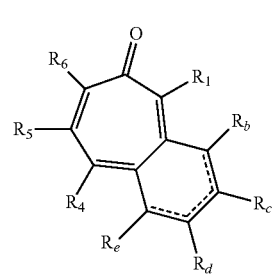

(IA)

wherein:

$R_b$, $R_c$, $R_d$, and $R_e$ are each independently hydrogen, hydroxy, or alkyl$_{(C \leq 8)}$, cycloalkyl$_{(C \leq 8)}$, alkenyl$_{(C \leq 8)}$, or a substituted version of any of these groups; or -alkanediyl$_{(C \leq 6)}$-alkylamino$_{(C \leq 8)}$, -alkane-diyl$_{(C \leq 6)}$-dialkylamino$_{(C \leq 8)}$, or a substituted version of either of these groups; or $R_1$ and $R_2$ are taken together and are a compound of the formula:

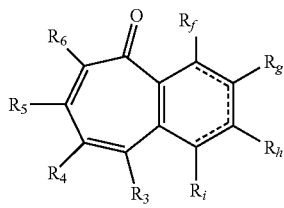

(IB)

wherein:

$R_f$, $R_g$, $R_h$, and $R_i$ are each independently hydrogen, hydroxy, or alkyl$_{(C \leq 8)}$, cycloalkyl$_{(C \leq 8)}$, alkenyl$_{(C \leq 8)}$, or a substituted version of any of these groups; or -alkanediyl$_{(C \leq 6)}$-alkylamino$_{(C \leq 8)}$, -alkanediyl$_{(C \leq 6)}$-dialkylamino$_{(C \leq 8)}$, or a substituted version of either of these groups; or $R_3$ and $R_4$ are taken together and are a compound of the formula:

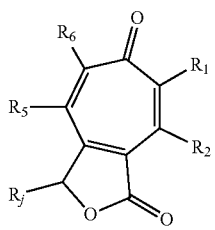

(IC)

wherein:

$R_j$ is hydrogen, hydroxy, halo, or alkyl$_{(C \leq 8)}$, cycloalkyl$_{(C \leq 8)}$, alkenyl$_{(C \leq 8)}$, or a substituted version of any of these groups; or -alkanediyl$_{(C \leq 6)}$-alkylamino$_{(C \leq 8)}$, -alkanediyl$_{(C \leq 6)}$-dialkylamino$_{(C \leq 8)}$, or a substituted version of either of these groups; or a compound of the formula:

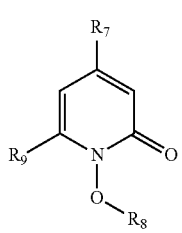

(II)

wherein:

$R_7$ is alkyl$_{(C \leq 12)}$, aryl$_{(C \leq 12)}$, aralkyl$_{(C \leq 12)}$, heteroaryl$_{(C \leq 12)}$, or a substituted version of any of these groups;

$R_8$ is hydrogen, alkyl$_{(C \leq 8)}$, or substituted alkyl$_{(C \leq 8)}$; and $R_9$ is hydrogen, alkyl$_{(C \leq 12)}$, or substituted alkyl$_{(C \leq 12)}$;

a compound of the formula:

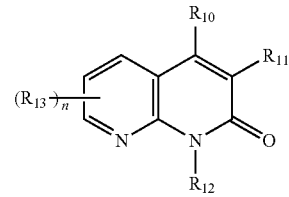

(III)

wherein:

$R_{10}$ is amino, hydroxy, or aryl$_{(C \leq 18)}$, aralkyl$_{(C \leq 18)}$, aryloxy$_{(C \leq 18)}$, cycloalkylamino$_{(C \leq 18)}$, aralkoxy$_{(C \leq 18)}$, arylamino$_{(C \leq 18)}$, aralkamino$_{(C \leq 18)}$, diarylamino$_{(C \leq 18)}$, diaralkamino$_{(C \leq 18)}$, or a substituted version of any of these groups;

$R_{11}$ is hydrogen, acyl$_{(C \leq 12)}$, or substituted acyl$_{(C \leq 12)}$, or —C(O)R$_a$; wherein:

$R_a$ is amino, hydroxy, alkoxy$_{(C \leq 8)}$, substituted alkoxy$_{(C \leq 8)}$, alkylamino$_{(C \leq 8)}$, substituted alkylamino$_{(C \leq 8)}$, dialkylamino$_{(C \leq 8)}$, or substituted dialkylamino$_{(C \leq 8)}$;

$R_{12}$ is hydrogen, alkoxy$_{(C \leq 8)}$, or substituted alkoxy$_{(C \leq 8)}$;

$R_{13}$ is amino, cyano, halo, hydroxy, nitro, alkyl$_{(C \leq 8)}$, substituted alkyl$_{(C \leq 8)}$, acyl$_{(C \leq 8)}$, substituted acyl$_{(C \leq 8)}$, alkoxy$_{(C \leq 8)}$, substituted alkoxy$_{(C \leq 8)}$, acyloxy$_{(C \leq 8)}$, substituted acyloxy$_{(C \leq 8)}$, alkylamino$_{(C \leq 8)}$, substituted alkylamino$_{(C \leq 8)}$, dialkylamino$_{(C \leq 8)}$, substituted dialkylamino$_{(C \leq 8)}$, amido$_{(C \leq 8)}$, or substituted amido$_{(C \leq 8)}$; and n is 1, 2, or 3;

or a pharmaceutically acceptable salt or tautomer thereof. In some embodiments, the compound is further defined by the formula:

or a pharmaceutically acceptable salt or tautomer thereof. Some non-limiting examples of the compounds described herein include those shown below in Table 1.

TABLE 1

Exemplary Compounds of the Present Disclosure

| Structure | Compound ID |
|---|---|
| (cyclohexyl-substituted N-hydroxy-4-methylpyridin-2(1H)-one) | 41 |
| (2,7-dihydroxy-5-isopropylcyclohepta-2,4,6-trien-1-one) | 46 |

TABLE 1-continued
Exemplary Compounds of the Present Disclosure
| Structure | Compound ID |
|---|---|
| 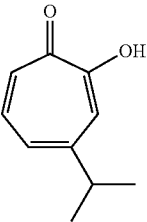 | 47 |
| 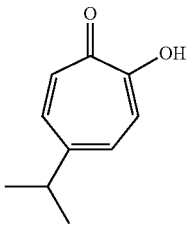 | 48 |
| 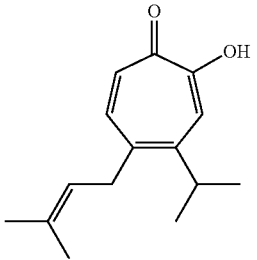 [SMILES: CC(C)=CCc1ccc(=O)c(O)cc1C(C)C] | 49 |
| 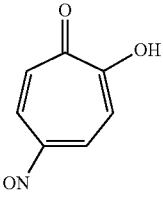 | 50 |
| 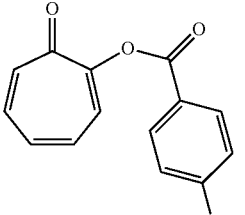 | 51 |
| 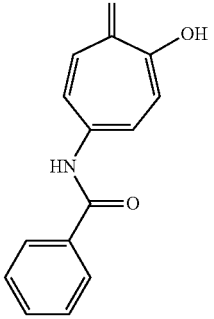 | 52 |
| 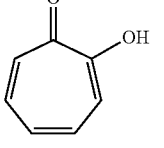 | 53 |
| 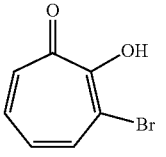 | 54 |
| 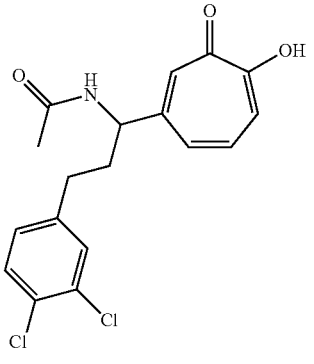 [SMILES: CC(=O)NC(CCc1ccc(Cl)c(Cl)c1)c1cccc(O)c(=O)c1] | 55 |
| 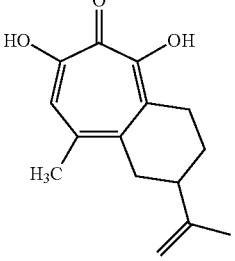 | 56 |
| 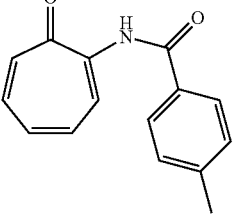 | 60 |

TABLE 1-continued
Exemplary Compounds of the Present Disclosure
| Structure | Compound ID |
|---|---|
| 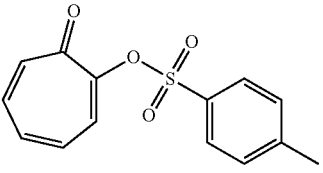 [SMILES: Cc1ccc(S(=O)(=O)Oc2cccccc2=O)cc1] | 61 |
| 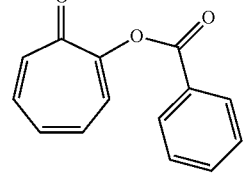 | 62 |
| 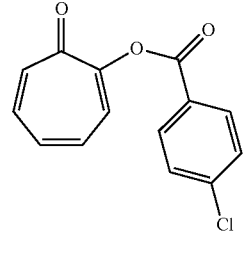 [SMILES: O=C(Oc1cccccc1=O)c1ccc(Cl)cc1] | 63 |
| 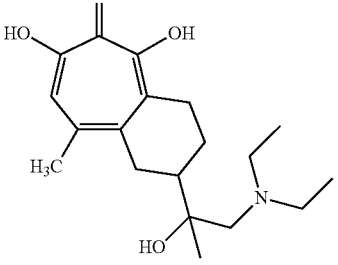 | 94 |
| 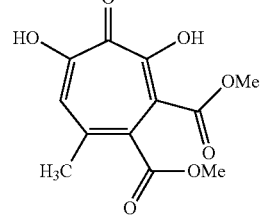 | 106 |
| 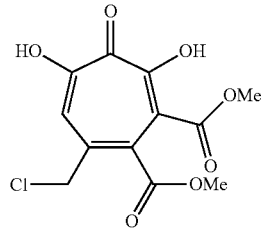 [SMILES: COC(=O)c1c(CCl)cc(O)c(=O)c(O)c1C(=O)OC] | 107 |
| 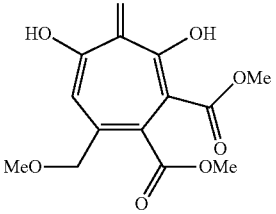 | 108 |
| 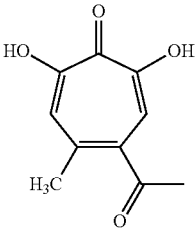 | 110 |
| 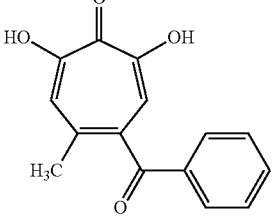 | 111 |
| 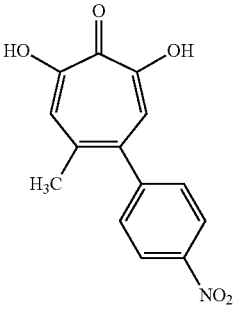 [SMILES: Cc1cc(O)c(=O)c(O)cc1-c1ccc([N+](=O)[O-])cc1] | 112 |
| 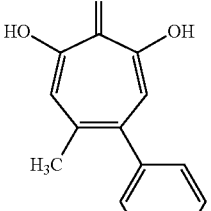 | 113 |

TABLE 1-continued

Exemplary Compounds of the Present Disclosure

| Structure | Compound ID |
|---|---|
| [structure: 2,7-dihydroxy-4-methyl-5-(4-bromophenyl)tropone] | 114 |
| [structure: 2,7-dihydroxy-4-methyl-5-(biphenyl-4-yl)tropone] | 115 |
| [structure: 2,7-dihydroxy-4-methyl-5-(biphenyl-4-ylcarbonyl)tropone] | 118 |
| [structure: 2,7-dihydroxy-4-methyl-5-(cyclohexylcarbonyl)tropone] | 120 |
| [structure: 2,7-dihydroxy-4-methyl-5-(isobutyryl)tropone] | 143 |
| [structure: 2,7-dihydroxy-4-methyl-5-(4-chlorophenyl)tropone] | 144 |
| [structure: 2,7-dihydroxy-4-methyl-5-(4-trifluoromethylphenyl)tropone] | 145 |
| [structure: 2,7-dihydroxy-4-methyl-5-(naphthalen-1-yl)tropone] | 146 |
| [structure: 4-hydroxy-1-hydroxy-1,8-naphthyridin-2(1H)-one] | 148 |
| [structure: 4-(4-bromobenzyl)-1-hydroxy-1,8-naphthyridin-2(1H)-one] | 149 |

TABLE 1-continued
Exemplary Compounds of the Present Disclosure
| Structure | Compound ID |
|---|---|
| 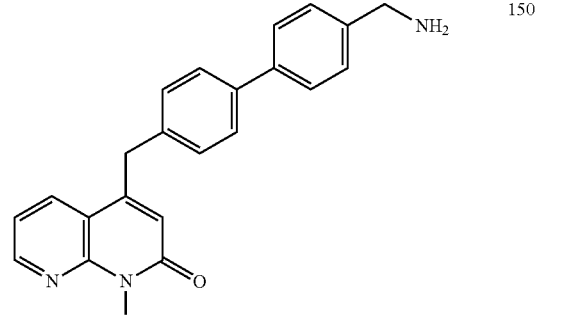 | 150 |
| 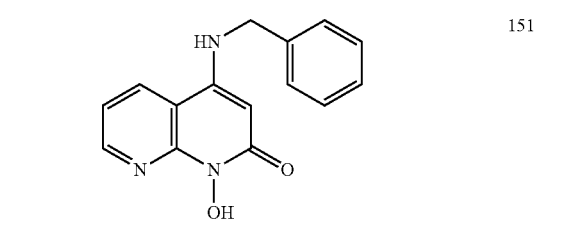 | 151 |
| 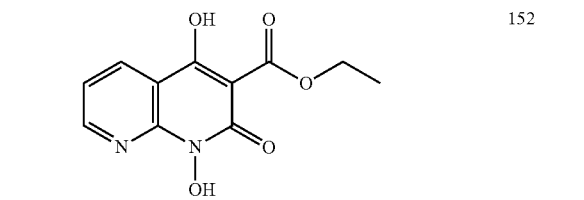 | 152 |
| 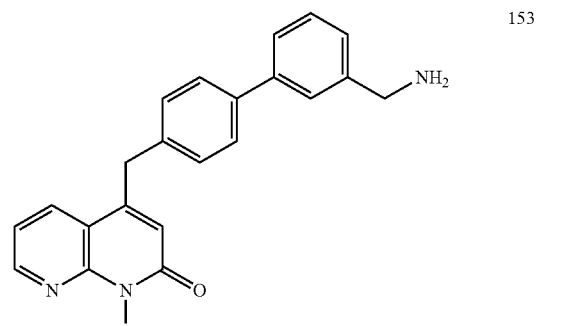 | 153 |
| 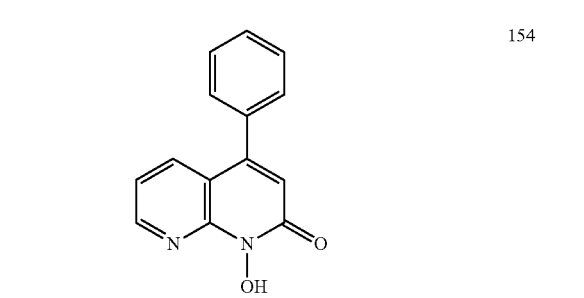 | 154 |
| 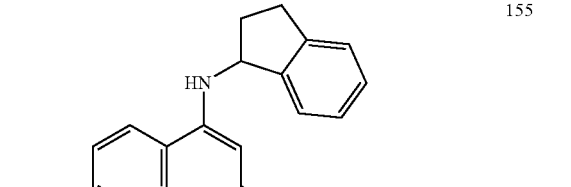 | 155 |
| 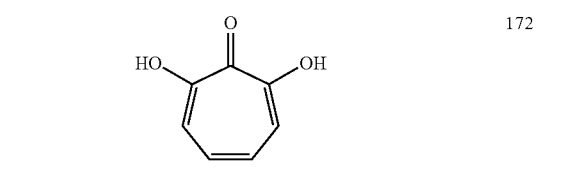 | 172 |
| 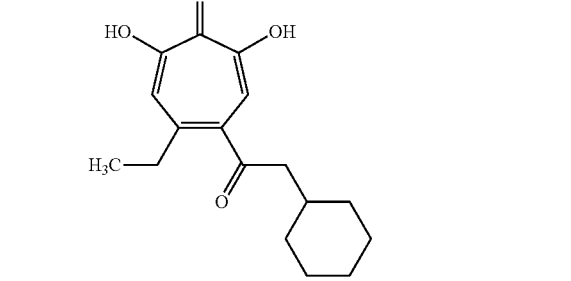 | 173 |
| 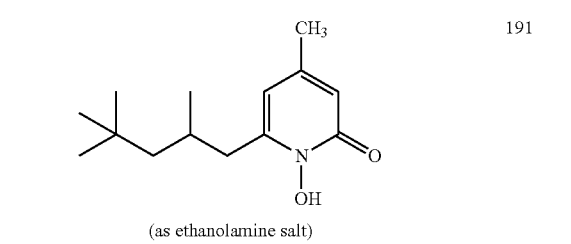 (as ethanolamine salt) | 191 |
| 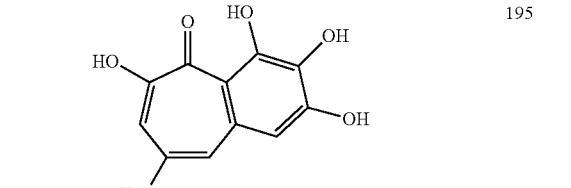 | 195 |
| 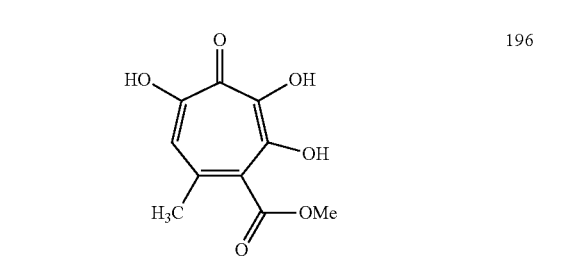 | 196 |

TABLE 1-continued

Exemplary Compounds of the Present Disclosure

| Structure | Compound ID |
|---|---|
| (2,7-dihydroxy-5-methyltropone) | 210 |
| (2,7-dihydroxy-5-methyl-4-(4-(naphthalen-2-yl)phenyl)tropone) | 233 |
| (2,7-dihydroxy-5-methyl-4-(4-(naphthalen-1-yl)phenyl)tropone) | 234 |
| (4-([1,1'-biphenyl]-3-carbonyl)-2,7-dihydroxy-5-methyltropone) | 255 |
| (2,7-dihydroxy-5-methyl-4-(4-(naphthalen-1-yl)benzoyl)tropone) | 256 |
| (2,7-dihydroxy-5-methyl-4-(3-(naphthalen-1-yl)benzoyl)tropone) | 257 |
| (2,7-dihydroxy-5-methyl-4-(4-(naphthalen-2-yl)benzoyl)tropone) | 258 |
| (2,7-dihydroxy-5-methyl-4-(3-(naphthalen-2-yl)benzoyl)tropone) | 259 |
| (2,7-dihydroxy-5-methyl-4-(4-(pyridin-4-yl)benzoyl)tropone) | 260 |
| (methyl 3,6-dihydroxy-2-methoxy-4-methyl-7-oxocyclohepta-1,3,5-triene-1-carboxylate) | 269 |
| (ethyl 2,3,6-trihydroxy-4-methyl-7-oxocyclohepta-1,3,5-triene-1-carboxylate) | 270 |

TABLE 1-continued

Exemplary Compounds of the Present Disclosure

| Structure | Compound ID |
|---|---|
| (structure) | 271 |
| (structure) | 272 |
| (structure) | 273 |
| (structure) | 281 |
| (structure) | 282 |

The compound of the disclosure contains one or more asymmetrically-substituted carbon or nitrogen atoms, and may be isolated in optically active or racemic form. Thus, all chiral, diastereomeric, racemic form, epimeric form, and all geometric isomeric forms of the chemical formula are intended, unless the specific stereochemistry or isomeric form is specifically indicated. The compound may occur as a racemate and racemic mixtures, single enantiomers, diastereomeric mixtures and individual diastereomers. In some embodiments, a single enantiomer or diastereomer is obtained. The chiral centers of the compound of the present disclosure can have the S or the R configuration.

Chemical formulas used to represent the compound of the disclosure will typically only show one of possibly several different tautomers. For example, many types of ketone groups are known to exist in equilibrium with corresponding enol groups. Regardless of which tautomer is depicted for a given compound, and regardless of which one is most prevalent, all tautomers of a given chemical formula are intended.

The compound of the disclosure may also have the advantage of being more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compound of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present disclosure may be replaced by a silicon atom(s). Furthermore, it is contemplated that one or more oxygen atom(s) of a compound of the present disclosure may be replaced by a sulfur or selenium atom(s).

The compound of the present disclosure may also exist in prodrug form. Since prodrugs are known to enhance numerous desirable qualities of pharmaceuticals (e.g., solubility, bioavailability, manufacturing, etc.), the compound employed in some methods of the disclosure may, if desired, be delivered in prodrug form. Thus, the disclosure contemplates prodrugs of the compound of the present disclosure as well as methods of delivering prodrugs. Prodrugs of the compound employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy group is bonded to any group that, when the prodrug is administered to a subject, cleaves to form a hydroxy group.

It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

2. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; "nitroso" means —NO; imino means=NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means=S; "sulfonyl" means —S(O)$_2$—; and "sulfinyl" means —S(O)—.

In the context of chemical formulas, the symbol "—" means a single bond, "=" means a double bond, and "≡" means triple bond. The symbol "-----" represents an optional bond, which if present is either single or double. The symbol "====" represents a single bond or a double bond. Thus, the formula

covers, for example,

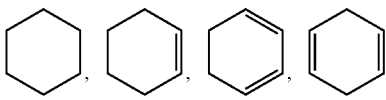

and

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⌇⌇⌇", when drawn perpendicularly across a bond

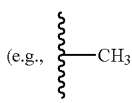

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⦀⦀⦀" means a single bond where the group attached to the thick end of the wedge is "into the page". The symbol "⌇⌇⌇" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

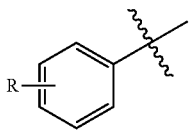

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

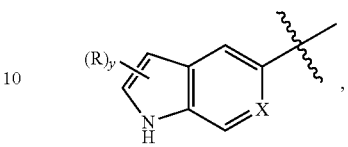

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C≤10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom(s) in a moiety replacing a hydrogen atom is not counted. Thus methoxyhexyl, which has a total of seven carbon atoms, is an example of a substituted alkyl$_{(C1-6)}$.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$-(methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. The cycloalkyl group may contain one or more alkyl, cycloalkyl, or aryl groups attached or fused to the cycloalkyl group so long as the cycloalkyl group is the point of attachment and these groups are within the carbon atom limit. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

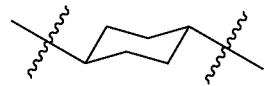 [SMILES: *C1CCC(*)CC1]

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

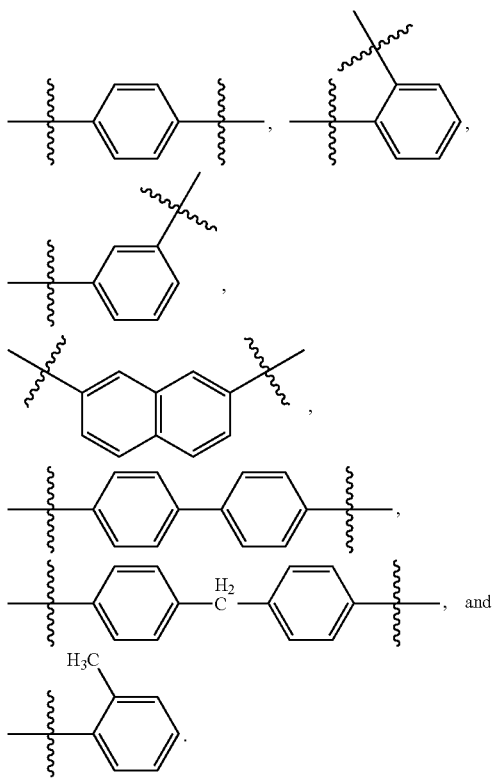

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl or cycloalkyl, as those terms are defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", "acyloxy", "alkylsulfonyloxy" when used without the "substituted" modifier, refers to groups, defined as —OR, in which R is alkenyl, alkynyl, aryl, aralkyl, heteroaryl, heterocycloalkyl, acyl, and alkylsulfonyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The term "alkylsulfonyl" when used without the "substituted" modifier refers to the group —S(O)$_2$R, in which R is an alkyl, as that term is defined above. The terms "cycloalkylsulfonyl", "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects, or +/−5% of the stated value.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living vertebrate organism, such as a human, monkey, cow, sheep, goat, dog, cat, mouse, rat, guinea pig, bird, fish or transgenic species thereof. In certain embodiments, the patient or subject is a primate. Non-limiting examples of human subjects are adults, juveniles, infants and fetuses.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of the compound of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease, including reactivation.

"Prodrug" means a compound that is convertible in vivo metabolically into an inhibitor according to the present disclosure. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Effective amount," "therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. In some embodiments, treatment of a patient afflicted with one of the pathological conditions described herein comprises administering to such a patient an amount of compound described herein which is therapeutically effective in controlling the condition or in prolonging the survivability of the patient beyond that expected in the absence of such treatment. As used herein, the term "inhibition" of the condition also refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

E. Therapeutic Methods

1. Pharmaceutical Formulations

In particular embodiments, where clinical application of an active ingredient is undertaken, it will be necessary to prepare a pharmaceutical composition appropriate for the intended application. Generally, this will entail preparing a pharmaceutical composition that is essentially free of pyrogens, as well as any other impurities or contaminants that could be harmful to humans or animals. One also will generally desire to employ appropriate buffers to render the complex stable and allow for uptake by target cells.

Aqueous compositions of the present disclosure comprise an effective amount of the active compound, as discussed above, further dispersed in pharmaceutically acceptable carrier or aqueous medium. Such compositions also are referred to as inocula. The phrase "pharmaceutically or pharmacologically acceptable" refers to compositions that do not produce an adverse, allergic or other untoward reaction when administered to an animal, or a human, as appropriate, as well as the requisite sterility for in vivo uses.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present disclosure are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, a controlled release patch, salve or spray. In some embodiments, the topical formulation by used for administration to the skin, to mucosa membranes such as the eye, eye lids, the genitals, the anus, or the inside of the mouth or nose, and in particular to the cornea.

An effective amount of the therapeutic composition is determined based on the intended goal. The term "unit dose" or "dosage" refers to physically discrete units suitable for use in a subject, each unit containing a predetermined quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment and the potency, stability and toxicity of the particular therapeutic substance.

2. Routes of Administration

Formulations of the present disclosure are suitable for oral administration. However, the therapeutic compositions of the present disclosure may be administered via any common route so long as the target tissue is available via that route. This includes nasal, buccal, corneal, ocularly, rectal, vaginal, or topical administration, and intradermal, subcutaneous, intramuscular, intraperitoneal or intravenous injection. As such, compositions would be formulated pharmaceutically in route-acceptable compositions that include physiologically acceptable carriers, buffers or other excipients.

As with dosing amounts, the timing of delivery (including intervals and total number of doses) depends on the judgment of the practitioner and are peculiar to each individual. Factors affecting dose include physical and clinical state of the patient, the route of administration, the intended goal of treatment and the potency, stability and toxicity of the particular therapeutic substance.

3. Combination Therapy

In many clinical situations, it is advisable to use a combination of distinct therapies. Thus, it is envisioned that, in addition to the therapies described above, one would also wish to provide to the patient more "traditional" pharmaceutical anti-fungal therapies. Examples of standard therapies are described above. Combinations may be achieved by administering a single composition or pharmacological formulation that includes both agents, or with two distinct compositions or formulations, at the same time, wherein one composition includes the agents of the present disclosure and the other includes the standard therapy. Alternatively, standard therapy may precede or follow the present agent treatment by intervals ranging from minutes to weeks to months. In embodiments where the treatments are applied separately, one would generally ensure that a significant period of time did not expire between the time of each delivery, such that the agents would still be able to exert an advantageously combined effect on the subject. In such instances, it is contemplated that one would administer both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the agent of the present disclosure, or the standard therapy will be desired. Various combinations may be employed, where the present disclosure compound is "A" and the standard therapy is "B," as exemplified below:

A/B/A B/A/B B/B/A A/A/B B/A/A A/B/B B/B/B/A B/B/A/B
A/A/B/B A/B/A/B A/B/B/A B/B/A/B B/A/B/A B/A/A/B B/B/B/A
A/A/A/B B/A/A/A A/B/A/A A/A/B/A A/B/B/B B/A/B/B B/B/A/B

Other combinations are contemplated as well. Drugs suitable for such combinations are described above and include, but are not limited to, amphotericin B, an azole anti-fungal compound, echinocandins, or flucytosine. Some non-limiting examples of azole anti-fungal compounds include fluconazole, itraconazole, posaconazole, or voriconazole. It is contemplated that other anti-fungal compounds may be used in combination with the present compounds.

E. EXAMPLES

The following examples are included to further illustrate various aspects of the disclosure. It should be appreciated by those of skill in the art that the techniques disclosed in the examples which follow represent techniques and/or compositions discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

1. Synthesis and Characterization

Synthesis:

All starting materials and reagents were purchased from commercially available sources and used without further purification, with exception of $CH_2Cl_2$ and benzene, which was purified on a solvent purification system prior to the reaction. $^1H$ NMR shifts are measured using the solvent residual peak as the internal standard ($CHCl_3$ d 7.26, $D_2O$ d 4.79), and reported as follows: chemical shift, multiplicity (s=singlet, bs=broad singlet, d=doublet, t=triplet, dd=doublet of doublet, q=quartet, m=multiplet), coupling constant (Hz), integration. $^{13}C$ NMR shifts are measured using the solvent residual peak as the internal standard ($CDCl_3$ d 77.20 or $D_2O$), and reported as chemical shifts. Infrared (IR) spectral bands are characterized as broad (br), strong (s), medium (m), and weak (w). Microwave reactions were preformed via the Biotage Intiator 2.5. Purification via normal phase column chromatography was performed on the Biotage Isolera Prime, with Biotage SNAP 10-25 g cartridges, in a solvent system of ethyl acetate in hexane. Purification for final compounds via reverse phase column chromatography was preformed on the Biotage Isolera Prime, with Biotage SNAP 12 g cartridges, in a solvent system of $CH_3CN$ in water each solvent containing 0.05% trifluoroacetic acid (TFA).

II. Synthesis of Aryl Ketone αHTs (308, 309, 311-313, 315)

A. General Synthetic Overview

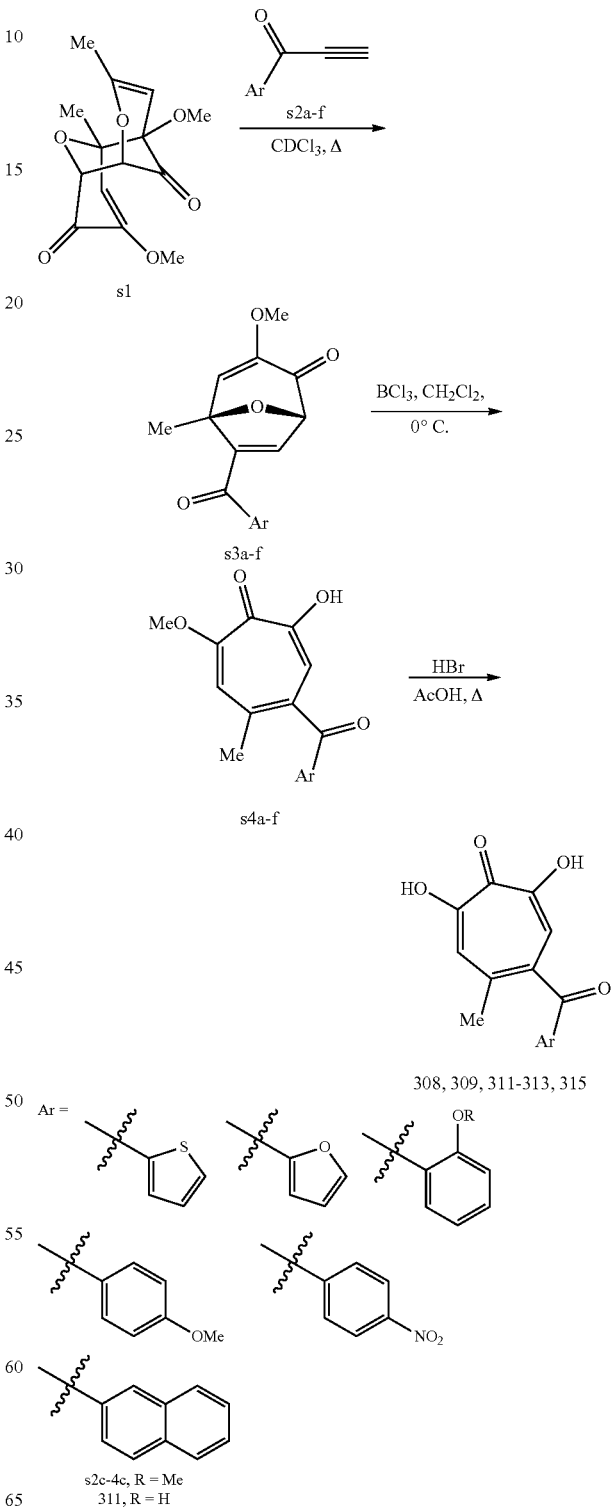

Scheme 1. Schematic Overview of Aryl Ketone αHT Synthesis

Synthesis of Alkynones (s2a-e)

Closely following literature precedent (Schubert, et al., 2001), in a round bottom flask, to a solution of acid chloride (1-2 g, 4.5 mM-9 mM, 1.0 eq) in $CH_2Cl_2$ (0.056 M), TMS acetylene (480-1000 mg, 4.95-9.9 mmol, 1.1 eq) is added. The flask was cooled to 0° C., then $AlCl_3$ (14-28 mmol, 3.1 eq) is added with vigorous stirring and left at 0° C. for 30 minutes. Then, the temperature was raised to room temperature, for 30 minutes. The reaction was quenched with 2M HCl and extracted with $CH_2Cl_2$. The organic layers were washed twice with saturated $NaHCO_3$ solution, followed by brine wash. After drying with $Na_2SO_4$, organic layers were filtered and concentrated under reduced pressure, to be used as such in next step. (Crude yields 80->100%)

Oxidopyrylium Cycloaddition: Synthesis of s3a-e

To a solution of (1R, 2S, 6S, 7R)-6,9-dimethoxy-4,7-dimethyl-3,11-dioxatricyclo[5.3.1.12,6]dodeca-4,8-diene-10,12-dione (s1) (Schubert, et al., 2001) (150-250 mg) in $CDCl_3$ (0.4-0.5 M, 1.1 mL) in a sealed tube, was added alkynones s2a-f (700-1200 mg, 4.2-6.36 mmol, 4-12 eq.). After stirring at 120° C., for 3 hr in an oil bath, the solvent was evaporated and crude material loaded onto column cartridge using 1-1.5 mL toluene, was purified by chromatography (Biotage Isolera Prime, SNAP 25 g silica gel, 18 cm×1.8 cm, solvent gradient: 5% EtOAc in hexanes (100 mL); 10% EtOAc in hexanes (200 mL); 20% EtOAc in hexanes (200 mL)). Product fractions were concentrated to yield s3a-f (60-95% yield)

$BCl_3$-Mediated Ring-Opening: Synthesis of s4a-e

A solution of $BCl_3$ (1.0 M in $CH_2Cl_2$, 7 eq, 2.955-5.91 mmol) was diluted with $CH_2Cl_2$ (0.014 M, 30-60 mL) and cooled to 0° C. In a separate round bottom flask, s3a-f (120-250 mg, 0.42-0.84 mmol) was dissolved in $CH_2Cl_2$ (0.014M, 30-60 mL), was cooled to 0° C. and was added to the $BCl_3$ solution. After 10 min of stirring at 0° C., the reaction mixture was quenched with $H_2O$ (60.3 mL), stirred for 2 min at 0° C., and then warmed to room temperature where it continued to stir for 1 hr. The organic layer was isolated and the aqueous layer was extracted with $CH_2Cl_2$ (5×10 mL). Combined organics were dried over $Na_2SO_4$, filtered, and concentrated under reduced pressure to yield s4a-e as solids. Reactions were immediately carried to next step.

HBr/AcOH Demethylation: Synthesis of α-Hydroxytropolones

A round bottom flask containing methoxytropolones s4a-f (100-200 mg) fitted with reflux condenser and base trap, a 33% HBr in acetic acid (0.09 M) was added to flask, and the reaction was heated to 120° C. for 1 hr. After 1 hour, reaction mixture was let to cool to room temperature, quenched with phosphate buffer (pH=7), and diluted with $CH_2Cl_2$. The organic layer was washed several times with the phosphate buffer. The organic layer was dried over $Na_2SO_4$, and evaporated under reduced pressure to yield pale yellow to brown solids 308, 309, 311-313, 315 (50-70% crude yield over two steps from s3a-e). They were further purified using reverse phase column chromatography conditions (Biotage Isolera Prime, SNAP 12 g C18 silica gel column, solvent gradient: 2-85% acetonitrile in water (35 CV); acetonitrile and water each contained 0.05% TFA)). Crude material loaded onto column cartridge using 1-1.5 mL DMSO. Product fractions were concentrated to yield 308, 309, 311-313, 315 (10-60 mg, 20-60% yields).

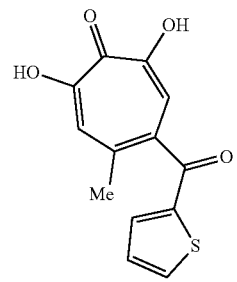

308

IIb. 4-(thiopene-2-carbonyl)-2,7-dihydroxy-5-methylcyclohepta-2,4,6-trien-1-one. (308)

1-(thiophen-2-yl) prop-2-yn-1-one (s2a) (340 mg, 2.5 mmol, 4 eq), was synthesized as described in the general synthetic method using thiophene-2-carbonyl chloride and carried through oxidopyrylium cycloaddition procedure with s1 (175 mg, 0.625 mmol, 1 eq) in $CDCl_3$ (0.4 M, 1.5 mL) to yield s3a as a pale brown oil. (250 mg, 0.71 mmol, 56% yield)$^1$H NMR (200 MHz, $CDCl_3$) δ 7.75 (dd, J=3.8 Hz, 0.8 Hz 2H), 7.18 (t, J=5 Hz, 4.4 Hz, 1H), 6.96 (d, J=2.4 Hz, 1H), 6.24 (s, 1H), 5.17 (d, J=2 Hz, 1H), 3.58 (s, 3H), 1.74 (s, 3H). Ring opening of s3a (250 mg, 0.905 mmol, 1 eq) was carried out with $BCl_3$ solution (6.34 mL, 6.34 mmol, 7 eq) to yield 318 as a pale brown solid (213 mg, 0.768 mmol, 85% yield). $^1$H NMR (400 MHz, $CDCl_3$) δ 7.80 (dd, J=4.9, 1.2 Hz, 1H), 7.42 (dt, J=6.7, 3.4 Hz, 1H), 7.31 (s, 1H), 7.16-7.12 (m, 1H), 7.07 (s, 1H), 4.05 (s, 3H), 2.40 (s, 3H). Demethylation of s4a (190 mg, 0.76 mmol, 1 eq) with HBr/AcOH (8.5 mL, 0.09M) followed by reverse phase column chromatography (Biotage Isolera Prime, SNAP 12 g C18 silica gel column, solvent gradient: 2-85% acetonitrile in water (35 CV); acetonitrile and water each contained 0.05% TFA)) yielded 308 (69 mg, 38% yield). 4-(thiopene-2-carbonyl)-2,7-dihydroxy-5-methylcyclohepta-2,4,6-trien-1-one. Pale brown liquid. IR (ATR, ZnSe) 3265 (b), 2862 (w), 1652 (s), 1533 (s), 1518 (s), 1400 (s), 1356 (m), 1287 (m), 1232 (m), 1090 (w), 913 (w), 803 (w), 728 (w) $cm^{-1}$. $^1$H NMR (400 MHz, $CDCl_3$) δ 7.81 (dd, J=4 Hz, 0.8 Hz 1H), 7.51 (s, 1H), 7.42 (s, 1H), 7.40 (t, J=3.2 Hz, 1H), 7.14 (dd, J=4 Hz, 0.8 Hz, 1H), 2.39 (s, 3H). $^{13}$C NMR (100 MHz, $CDCl_3$) δ 189.29, 168.29, 159.08, 156.85, 157.05, 142.97, 139.28, 138.25, 136.49, 135.98, 128.66, 124.56, 119.10, 24.45. HRMS (ESI+): m/z calc'd for $C_{13}H_{10}O_4SH+$: 262.0372 Found: 263.0384.

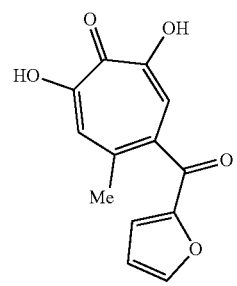

309

IIc. 4-(furan-2-carbonyl)-2,7-dihydroxy-5-methylcyclohepta-2, 4,6-trien-1-one. (309)

1-(furan-2-yl) prop-2-yn-1-one (s2b) (900 mg, 8 mmol, 7 eq) was synthesized as described in the general synthetic method using furan-2-carbonyl chloride and carried through oxidopyrylium cycloaddition procedure with s1 (280 mg, 1 mmol, 1 eq) in CDCl$_3$ (0.5 M, 2 mL) to yield s3b as a pale brown oil (220 mg, 0.85 mmol, 42% yield) $^1$H NMR (200 MHz, CDCl$_3$) δ 7.66 (dd, J=3.8 Hz, 0.8 Hz 2H), 7.26 (m, 2H), 6.60 (t, J=1.6 Hz, 2 Hz, 1H), 6.23 (s, 1H), 5.17 (dd, J=1.2 Hz, 1H), 3.57 (s, 3H), 1.77 (s, 3H). Ring opening of s3b (250 mg, 0.905 mmol, 1 eq) was carried out with BCl$_3$ solution (5.91 mL, 5.91 mmol, 7 eq) to yield a mixture of s4b and 309 (220 mg, ~85% crude yield), which was homogenized with HBr/AcOH (9 mL, 0.09 M) and chromatographed (Biotage Isolera Prime, SNAP 12 g C18 silica gel column, solvent gradient: 2-85% acetonitrile in water (35 CV); acetonitrile and water each contained 0.05% TFA)) to yield 309 as a pale yellow solid 309 (12 mg, 5% yield over 2 steps). IR (ATR, ZnSe) 3259 (b), 2924 (w), 1662 (s), 1389 (m), 1300 (m), 1226 (m), 1161 (w), 1090 (w) cm$^{-1}$. $^1$H NMR (400 MHz, CDCl$_3$) 7.71 (dd, J=1.6 Hz 1H), 7.51 (s, 1H), 7.41 (s, 1H), 7.09 (d, J=3.2 Hz, 1H), 6.60 (dd, J=3.6 Hz, 1.6 Hz, 1H), 2.39 (s, 3H). $^{13}$C NMR (100 MHz, CDCl$_3$) δ 184.24, 168.35, 158.97, 156.85, 151.45, 148.61, 138.90, 138.24, 124.36, 121.88, 119.12, 112.92, 24.35. HRMS (ESI+): m/z calc'd for C$_{13}$H$_{10}$O$_5$H+: 247.0600 Found: 247.0606.

311

IId. 4-(2-hydroxybenzoyl)-2,7-dihydroxy-5-methyl-cyclohepta-2,4,6-trien-1-one (311)

1-(2-methoxyphenyl)prop-2-yn-1-one (s2c) (430 mg, 2.68 mmol, 5 eq) was synthesized as described in the general synthetic method using 2-methoxybenzoyl chloride and carried through oxidopyrylium cycloaddition procedure with (150 mg, 0.53 mmol, 1 eq) in CDCl$_3$ (0.4 M, 1.32 mL) to yield s3c as a pale brown oil (230 mg, 0.76 mmol, 71% yield). $^1$H NMR (200 MHz, CDCl$_3$) δ 7.42-7.32 (m, 2H), 6.95 (t, J=8.2 Hz, 2H), 6.58 (d, J=2.8 Hz, 1H), 6.21 (s, 1H), 5.01 (dd, J=2.6 Hz, 1H), 3.77 (s, 3H), 3.55 (s, 3H), 1.78 (s, 3H). Ring opening of s3c (230 mg, 0.76 mmol, 1 eq) was carried out with BCl$_3$ solution (5.36 mL, 5.36 mmol, 7 eq) to yield a mixture of s4c and 311 (200 mg, ~85% crude yield), which was homogenized with HBr/AcOH to yield 311 as a pale brown solid (60 mg, 0.22 mmol, 28% yield over 2 steps). IR (ATR, ZnSe) 3055 (b), 2925 (w), 2847 (w), 1625 (s), 1531 (s), 1486 (s), 1400 (s), 1356 (m), 1287 (m), 1232 (m), 1144 (m), 1063 (w), 906 (w) cm$^{-1}$. $^1$H NMR (400 MHz, CDCl$_3$) δ 7.55 (dt, J=7.2 Hz, 5.6 Hz, 1.6 Hz, 1H), 7.51 (s, 1H), 7.30 (s, 1H), 7.09 (dd, J=8 Hz, 0.4 Hz, 1H), 6.86 (d, J=0.8 Hz, 1H), 6.83 (t, J=7.2 Hz, 1H), 2.34 (s, 3H). $^{13}$C NMR (100 MHz, CDCl$_3$) δ 202.62, 168.39, 163.65, 159.01, 157.16, 137.89, 137.81, 137.58, 132.81, 124.34, 119.56, 118.80, 118.74, 118.57, 24.45. HRMS (ESI+): m/z calc'd for C$_{15}$H$_{12}$O$_5$H+: 273.0757 Found: 273.0994.

312

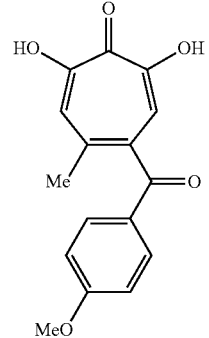

IIe. 4-(4-methoxybenzoyl)-2,7-dihydroxy-5-methyl-cyclohepta-2,4,6-trien-1-one (312)

1-(4-methoxyphenyl) prop-2-yn-1-one (s2d) (430 mg, 2.68 mmol, 5 eq) was synthesized as described in the general synthetic method using 4-methoxybenzoyl chloride and carried through oxidopyrylium cycloaddition procedure with s1 (150 mg, 0.53 mmol, 1 eq) in CDCl$_3$ (0.4 M, 1.32 mL) to yield s3d as a pale brown solid (230 mg, 0.76 mmol, 71% yield) $^1$H NMR (200 MHz, CDCl$_3$) δ 7.42-7.32 (m, 2H), 6.95 (t, J=8.2 Hz, 2H), 6.58 (d, J=2.8 Hz, 1H), 6.21 (s, 1H), 5.01 (dd, J=2.6 Hz, 1H), 3.77 (s, 3H), 3.55 (s, 3H), 1.78 (s, 3H). Ring opening of s3d (530 mg, 1.76 mmol, 1 eq) was carried out with BCl$_3$ solution (12.36 mL, 12.36 mmol, 7 eq) to yield a mixture of s4d and 312 (375 mg, ~70% crude yield), which was homogenized with HBr/AcOH (14 mL, 0.09M) and chromatographed (Biotage Isolera Prime, SNAP 12 g C18 silica gel column, solvent gradient: 2-85% acetonitrile in water (35 CV); acetonitrile and water each contained 0.05% TFA)) to yield 312 as a pale yellow solid (66 mg, 0.23 mmol, 13% yield over 2 steps). IR (ATR, ZnSe) 3243 (b), 1661 (s), 1598 (s), 1568 (s), 1531 (s), 1504 (s), 1389 (b), 1290 (m), 1163 (s), 1093 (s), 1021 (s), 903 (s) cm$^{-1}$. $^1$H NMR (400 MHz, CDCl$_3$) δ 7.77 (d, J=8 Hz, 2H), 7.50 (s, 1H), 7.31 (s, 1H), 6.95 (d, J=8.4 Hz 2H), 3.88 (s, 3H), 2.25 (s, 3H). $^{13}$C NMR (400 MHz, CDCl$_3$) δ 195.68, 168.11, 164.56, 158.80, 157.23, 140.26, 137.91, 132.56, 128.48, 124.56, 119.16, 114.28, 55.65, 24.37. HRMS (ESI+): m/z calc'd for C$_{16}$H$_{14}$O$_5$H$^+$: 287.0913. Found: 287.0926.

313

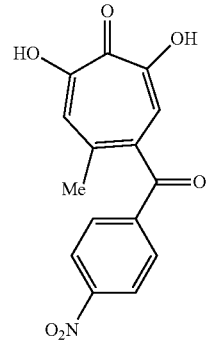

IIe. 2,7-dihydroxy-4-methyl-5-(4-nitrobenzoyl)cyclohepta-2,4,6-trien-1-one (313)

1-(4-nitrophenyl) prop-2-yn-1-one (s2e) (1.20 g, 6.85 mmol, 12 eq) was synthesized as described in the general synthetic method using 4-methoxybenzoyl chloride and carried through oxidopyrylium cycloaddition procedure with s1 (150 mg, 0.53 mmol, 1 eq) in CDCl$_3$ (0.4 M, 4.6 mL) to yield s3e as a pale brown solid (120 mg, 0.38 mmol, 35% yield). $^1$H NMR (200 MHz, CDCl$_3$) δ 7.42-7.32 (m, 2H), 6.95 (t, J=8.2 Hz, 2H), 6.58 (d, J=2.8 Hz, 1H), 6.21 (s, 1H), 5.01 (dd, J=2.6 Hz, 1H), 3.77 (s, 3H), 3.55 (s, 3H), 1.78 (s, 3H). Ring opening of s3e (120 mg, 0.38 mmol, 1 eq) was carried out with BCl$_3$ solution (2.66 mL, 2.66 mmol, 7 eq) to yield a mixture of s4e and 313 (>120 mg crude yield), which was homogenized with HBr/AcOH (4.55 mL, 0.09M) and chromatographed (Biotage Isolera Prime, SNAP 12 g C18 silica gel column, solvent gradient: 2-85% acetonitrile in water (35 CV); acetonitrile and water each contained 0.05% TFA)) to yield 313 as a pale yellow solid (40 mg, 0.13 mmol, 32% yield over 2 steps). IR (ATR, ZnSe) 2957 (b), 2940 (s), 2858 (s), 1673 (s), 1598 (s), 1454 (s), 1394 (b), 1349 (s), 1286 (m), 1078 (s), 1021 (s), 907 (s) cm$^{-1}$. $^1$H NMR (400 MHz, CDCl$_3$) δ 8.34 (d, J=8.4 Hz, 2H), 7.98 (d, J=8.4 Hz, 2H), 7.53 (s, 1H), 7.26 (s, 1H), 2.32 (s, 3H). $^{13}$C NMR (100 MHz, CDCl$_3$) δ 195.44, 168.70, 159.05, 156.89, 150.94, 140.21, 138.33, 137.78, 130.98, 124.24, 118.33, 24.62. HRMS (ESI+): m/z calc'd for C$_{15}$H$_{11}$NO$_6$H$^+$: 302.0658. Found: 302.0660.

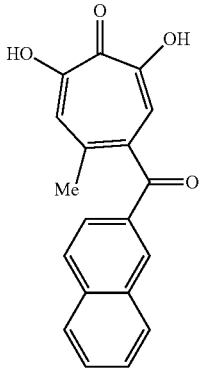

315

IIg. 4-(2-naphthoyl)-2,7-dihydroxy-5-methylcyclohepta-2, 4,6-trien-1-one (315)

1-(naphthalen-2-yl) prop-2-yn-1-one (s2f) (763 mg, 4.24 mmol, 8 eq) was synthesized as described in the general synthetic method using 2-naphthoyl chloride and carried through oxidopyrylium cycloaddition procedure with s1 (150 mg, 0.53 mmol, 1 eq) in CDCl$_3$ (0.4 M, 1.32 mL) as described previously to yield s3 g as a pale brown solid. (101 mg, 0.31 mmol, 30% yield). $^1$H NMR (200 MHz, CDCl$_3$) δ 8.37 (d, J=0.8 Hz, 1H), 7.99 (d, J=8.2 Hz, 1H), 7.87 (d, J=5.8 Hz, 1H), 7.71 (d, J=7.4 Hz, 1H), 7.42-7.32 (m, 2H), 6.65 (s, 1H), 6.33 (d, J=1.2 Hz, 1H), 5.09 (dd, J=1.6 Hz, 1.4 Hz, 1H), 3.60 (s, 3H), 1.86 (s, 3H). Ring opening of s3f (101 mg, 0.31 mmol, 1 eq) was carried out with BCl$_3$ solution (2.2 mL, 2.2 mmol, 7 eq) to yield a mixture of s4f and 315 (68 mg, ~68% crude yield), which was homogenized with HBr/AcOH (2.4 mL, 0.09 M) and chromatographed (Biotage Isolera Prime, SNAP 12 g C18 silica gel column, solvent gradient: 2-85% acetonitrile in water (35 CV); acetonitrile and water each contained 0.05% TFA)) to yield 315 as a pale yellow solid (11 mg, 0.03 mmol, 11% yield over 2 steps). $^1$H NMR (400 MHz, CDCl$_3$) δ 8.10 (s, 1H), 8.02-7.87 (m, 4H), 7.65 (dt, J=1.6 Hz, 1.2 Hz, 1H), 7.56 (dt, J=1.6 Hz, 1.2 Hz, 1H), 7.55 (s, 1H), 7.34 (s, 1H), 2.35 (s, 3H). $^{13}$C NMR (100 MHz, CDCl$_3$) δ 197.13, 168.37, 158.75, 157.02, 139.91, 138.20, 136.13, 133.07, 132.96, 132.41, 129.80, 129.39, 129.19, 127.95, 127.21, 124.42, 124.39, 118.98, 24.55. HRMS (ESI+): m/z calc'd for C$_{19}$H$_{14}$O$_4$H$^+$: 307.0964 Found: 307.0967.

III. Synthesis and Characterization of Hydroxytropolone 310

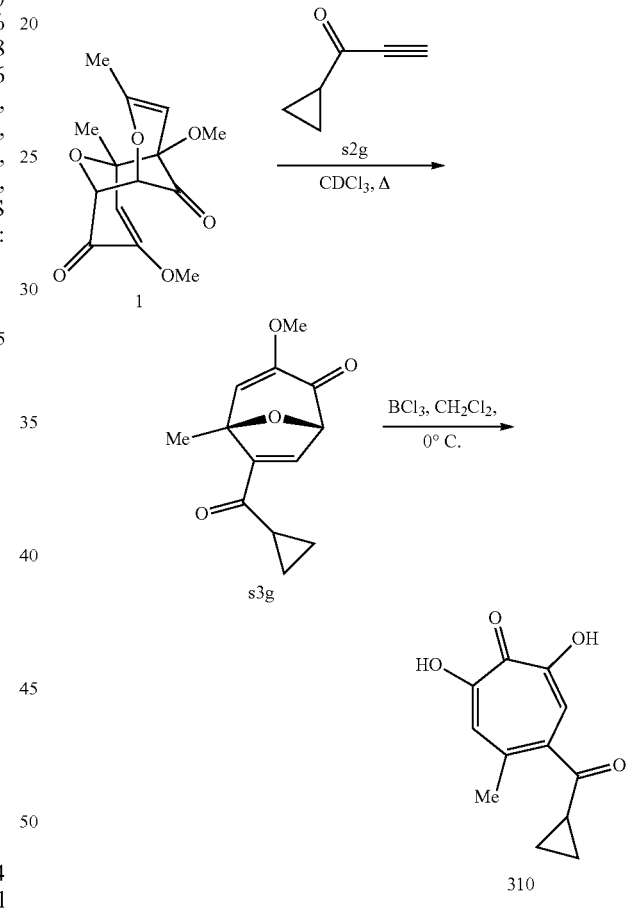

1-cyclopropylprop-2-yn-1-one (s2 g) (1.12 g, 4.24 mmol, 22 eq) was synthesized as described in the general synthetic method using cyclopropanecarbonyl chloride and carried through oxidopyrylium cycloaddition procedure with s1 (150 mg, 0.53 mmol, 1 eq) as described previously to yield s3 g. (122 mg, 0.55 mmol, 52% yield) (1S,5S)-6-(cyclopropanecarbonyl)-3-methoxy-5-methyl-8-oxabicyclo[3.2.1]octa-3,6-dien-2-one pale brown solid. $^1$H NMR (200 MHz, CDCl$_3$) δ 7.14 (s, 1H), 6.09 (s, 1H), 5.80 (s, 1H), 7.71 (d, J=7.4 Hz, 1H), 3.53 (s, 3H), 2.28 (m, 1H), 1.71 (s, 3H), 1.13-0.98 (m, 4H). Ring opening of s3 g (122 mg, 0.55 mmol, 1 eq) with BCl$_3$ solution (3.91 mL, 3.91 mmol, 7 eq) yielded direct conversion to 310. (22 mg, 0.1 mmol, 20% yield) 4-(cyclopropanecarbonyl)-2,7-dihydroxy-5-methyl-cyclohepta-2,4,6-trien-1-one. pale yellow oil. IR (ATR, ZnSe) 3253 (b), 3004 (w), 1683 (s), 1611 (s), 1539 (m), 1434 (m), 1376 (m), 1281 (m), 1197 (m), 1156 (w), 1124 (w), 1095 (w), 974 (m) cm$^{-1}$. $^1$H NMR (400 MHz, CDCl$_3$) δ 7.49 (s, 2H), 2.47 (s, 3H), 2.22 (t, J=4.8 Hz, 4.4 Hz, 1H), 1.339 (t, J=4.4 Hz, 3.6 Hz, 2H), 1.34-1.15 (m, 2H). $^{13}$C NMR (100 MHz, CDCl$_3$) δ 206.66, 168.16, 158.67, 157.18, 142.11, 137.62, 124.61, 118.61, 24.64, 21.99, 13.40, 13.29. HRMS (ESI+): m/z calc'd for C$_{12}$H$_{12}$O$_4$H$^+$: 221.0808. Found: 221.0815.

IV. Synthesis and Characterization of Methoxytropolone 317

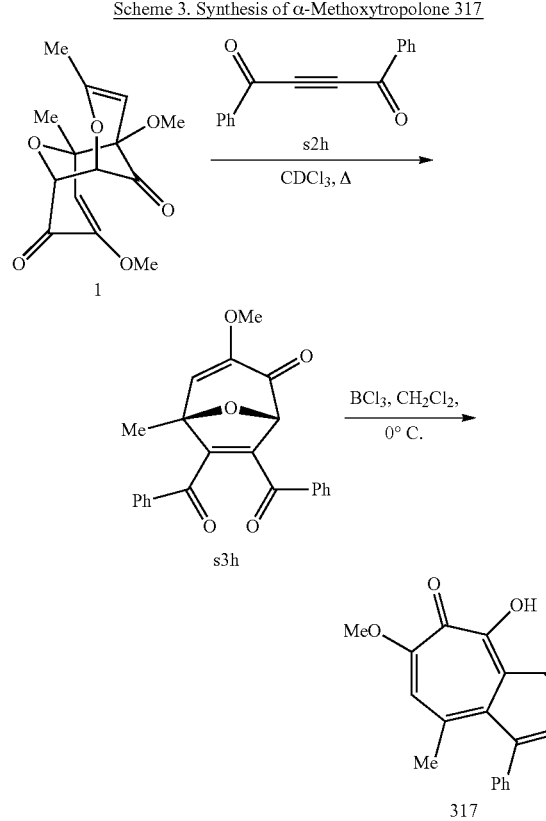

To a solution of s1 (44 mg, 0.32 mmol, 1.5 eq) in CDCl$_3$ (0.14 M, 1.5 mL) was added 1,4-diphenylbut-2-yne-1,4-dione s2h (50 mg, 0.213 mmol, 1 eq). After microwave irradiation at 100° C. for 15 minutes, the reaction mixture was purified by chromatography (Biotage Isolera Prime, SNAP 10 g silica gel column, solvent gradient: 5% EtOAc in hexanes (3 CV); 5-30% EtOAc in hexanes (20 CV)). Product fractions were concentrated to yield s3h. (52 mg, 0.13 mmol, 65% yield). R$_f$=0.50 in 40% EtOAc in hexanes. ((1S, 5S)-3-methoxy-1-methyl-4-oxo-8-oxabicyclo [3.2.1] octa-2,6-diene-6,7-diyl)bis(phenylmethanone) pale yellow liquid $^1$H NMR (400 MHz, CDCl$_3$) δ 7.46-7.36 (m, 1H), 7.31-7.27 (m, 1H), 7.24-7.16 (m, 1H), 6.33 (s, 1H), 5.61 (s, 1H), 3.69 (d, J=20.0 Hz, 1H), 1.70 (d, J=30.3 Hz, 1H). $^{13}$C NMR (100 MHz, CDCl$_3$) δ 192.27, 189.66, 187.54, 155.05, 145.45, 143.28, 137.36, 136.99, 133.92, 133.51, 128.59, 128.54, 128.51, 128.38, 119.87, 89.54, 88.69, 77.36, 77.05, 76.73, 55.08, 20.95. Ring opening of s3h (100 mg, 0.26 mmol, 1 eq) was carried out with BCl$_3$ solution (1.86 mL, 1.86 mmol, 7 eq) according to previous procedure to yield 317 (100 mg, 0.26 mmol, 100% yield) (7-hydroxy-5-methoxy-3-methyl-6-oxocyclohepta-2, 4,7-triene-1, 2-diyl) bis (phenyl methanone) pale brown solid. IR (ATR, ZnSe) 2898 (w), 1671 (s), 1592 (s), 1571 (m), 1556 (m), 1444 (m), 1389 (s), 1175 (m), 1090 (w), 1021 (s), 845 (w), 770 (s) cm$^{-1}$. $^1$H NMR (400 MHz, CDCl$_3$) δ 7.81-7.66 (m, 1H), 7.54 (dt, J=11.0, 7.5 Hz, 1H), 7.39 (dt, J=11.1, 7.8 Hz, 1H), 7.11 (s, 1H), 4.07 (s, 1H), 2.24 (s, 1H). $^{13}$C NMR (100 MHz, CDCl$_3$) δ 196.95, 194.60, 170.52, 158.88, 156.14, 138.09, 136.61, 136.37, 134.22, 133.97, 133.88, 133.81, 129.77, 129.46, 128.83, 128.63, 128.51, 122.09, 77.41, 77.29, 77.09, 76.77, 56.73, 25.57. HRMS (ESI+): m/z calc'd for C$_{16}$H$_{14}$O$_5$H$^+$: 375.1226. Found: 375.1233.

V. Synthesis of αHT Carboxylic Acid 319

4,6-dihydroxy-2-methyl-5-oxocyclohepta-1, 3,6-triene-1-carboxylic Acid 319

To a solution of methyl 3-methoxy-5-methyl-2-oxo-8-oxabicyclo [3.2.1] octa-3, 6-diene-6-carboxylate (Meck, et al., 2012) (300 mg, 1.34 mmol) in CH$_2$Cl$_2$ (13.4 mL) was added triflic acid (473 μL, 5.36 mmol). The reaction was allowed to stir for 30 min at rt, at which point NaOAc (1.1 g, 13.4 mmol) was added and stirred for an additional 10 min at rt. The reaction mixture was concentrated under reduced pressure, and H$_2$O (724 μL, 40.2 mmol) in 13 mL of 33% HBr/AcOH solution was added. The reaction was heated to 120° C. for 4 h before being quenched with pH 7 phosphate buffer to a pH of 4. The reaction mixture was extracted with CH$_2$Cl$_2$ (5×20 mL) followed by EtOAc (3×20 mL). The combined organics were dried over Na$_2$SO$_4$, filtered, and concentrated under reduced pressure to yield 1 as a brown solid (135 mg, 51% yield) that decomposes at 235° C. IR (ATR, ZnSe) 3302 (m), 3157 (b), 2925 (m), 2853 (m), 1708 (s), 1611 (w), 1533 (s), 1495 (w), 1431 (w), 1176 (s), 1137 (m), 906 (m), 782 (w), 713 (w) cm$^{-1}$. $^1$H NMR (400 MHz, MeOD) δ 7.62 (s, 1H), 7.45 (s, 1H), 2.53 (s, 3H). $^{13}$C NMR (100 MHz, DMSO-d$_6$) δ 170.15, 168.48, 159.87, 157.16, 137.56, 131.99, 123.67, 119.29, 24.56. HRMS (ESI+): m/z calc'd for C$_9$H$_9$O$_5$$^+$: 197.0444. Found: 197.0443.

VI. Synthesis of αHT Lactone 280

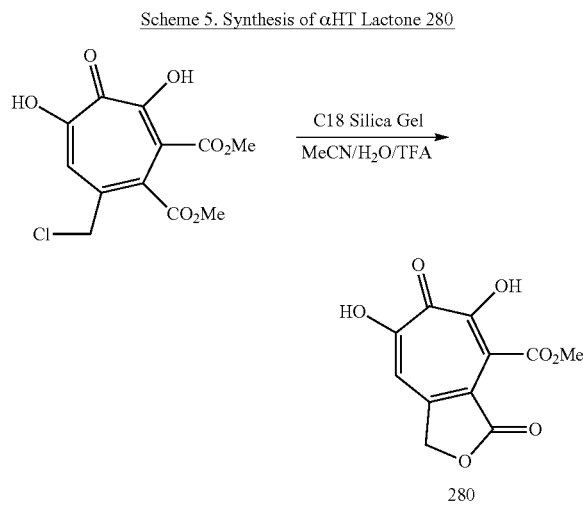

Methyl 5,7-dihydroxy-3,6-dioxo-3,6-dihydro-1H-cyclohepta[c]furan-4-carboxylate (280)

Dimethyl 3-(chloromethyl)-5,7-dihydroxy-6-oxocyclohepta-2,4,7-triene-1,2-dicarboxylate (Meck, et al., 2012) (26 mg, 0.086 mmol) was subjected to reverse phase column chromatography conditions (Biotage Isolera Prime, SNAP 12 g C18 silica gel column, solvent gradient: 2-85% acetonitrile in water (35 CV); acetonitrile and water each contained 0.05% TFA)). Product fractions were concentrated to yield 280 as a yellow solid (12 mg, 55% yield). MP=252-255° C. IR (ATR, ZnSe) 3325 (b), 2930 (w), 1737 (s), 1723 (s), 1714 (s), 1623 (w), 1569 (m), 1471 (m), 1438 (m), 1354 (s), 1303 (s), 1259 (m), 1146 (s), 1034 (m), 980 (m), 793 (m) cm$^{-1}$. $^1$H NMR (400 MHz, Acetone-d$_6$) δ 7.62 (s, 1H), 5.39 (s, 2H), 3.92 (s, 3H). $^{13}$C NMR (150 MHz, Acetone-d$_6$) δ 173.61, 170.64, 165.61, 162.70, 155.70, 149.87, 122.38, 118.98, 113.06, 71.49, 52.95. HRMS (ESI+): m/z calc'd for C$_{11}$H$_8$O$_7$Na$^+$: 275.0162. Found: 275.0163.

VI. Synthesis of Monosubstituted αHTs

The following procedures are derived from the work of Banwell et al, whereby 1,4-cyclohexadiene was converted into 4-bromo-2,7-dihydroxycyclohepta-2,4,6-trien-1-one (s5), (Amon, et al., 1987) which subsequently serves as an intermediate for various αHTs through cross-coupling and demethylation sequence (Banwell, et al., 1991).

Scheme S5. General Overview of Banwell αHT synthesis strategy

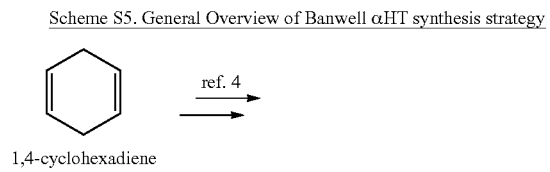

1,4-cyclohexadiene

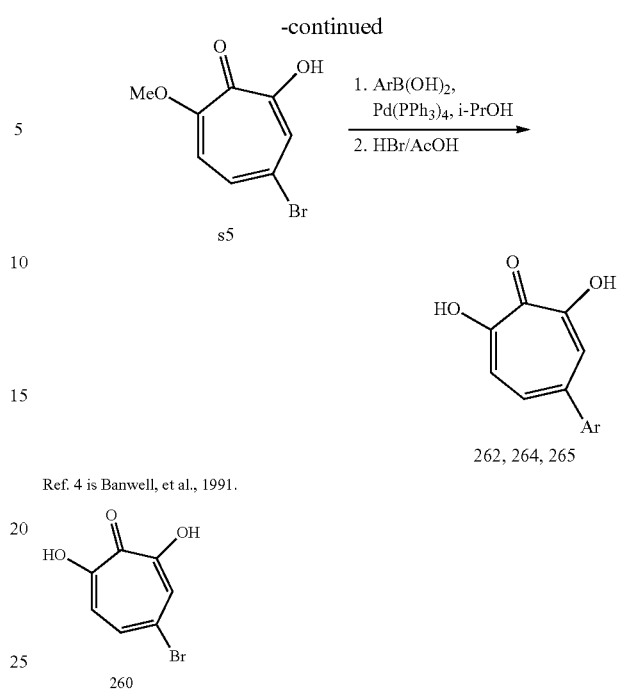

Ref. 4 is Banwell, et al., 1991.

VIa. 4-bromo-2,7-dihydroxycyclohepta-2,4,6-trien-1-one (260)

4-bromo-2,7-dihydroxycyclohepta-2,4,6-trien-1-one (s5) (100.8 mg, 0.436 mmol) was dissolved in 33% HBr in acetic acid to a concentration of 0.1M, and heated to 120° C. in a sealed vessel for 1 hr. The reaction was diluted 20 fold with CH$_2$Cl$_2$ and 0.2M phosphate buffer was added until the pH of the aqueous layer was ~6. The reaction was then extracted 3× with CH$_2$Cl$_2$ and the combined organic extracts dried over Na$_2$SO$_4$, and the solvent evaporated under reduced pressure to afford the product, 4-bromo-2,7-dihydroxycyclohepta-2,4,6-trien-1-one, as a brown solid. (94 mg, >95% yield)$^1$H NMR (400 MHz, CDCl$_3$) δ 8.34 (br s, 1H), 7.80 (d, J=2.0 Hz, 1H), 7.51 (dd, J=11.0, 2.0 Hz, 1H), 7.25 (d, J=11.0 Hz, 1H). HRMS (TOF MS ES+) m/z Calcd for C$_8$H$_5$BrO$_3$: 216.9500. Mass Found: 216.9513.

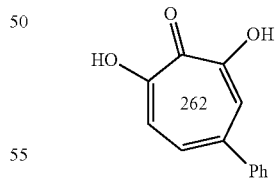

VIb. 2,7-dihydroxy-4-phenylcyclohepta-2,4,6-trien-1-one (262)

4-bromo-2,7-dihydroxycyclohepta-2,4,6-trien-1-one (s5) (19.6 mg, 0.085 mmol) and benzene boronic acid (14.5 mg, 0.119 mmol) were dissolved in 4.25 mL of 2-propanol. 1.19 mL of 1 M aq. Na$_2$CO$_3$ was then added and the solution was purged with Ar for 15 min, and Pd(PPh$_3$)$_4$ (9.8 mg, 0.008 mmol) was added, and the reaction was stirred in a sealed vessel at 85° C. for 48 hrs. The reaction was poured into water, and extracted 3×DCM. The combined organic extracts were dried over $Na_2SO_4$, and the solvent evaporated under reduced pressure. The product, 7-hydroxy-2-methoxy-4-phenylcyclohepta-2,4,6-trien-1-one (15 mg, 77% isolated yield), was purified by RP-Flash chromatography using a C18 column and eluting with a linear gradient of 20%-60% acetonitrile in water containing 0.05% trifluoroacetic acid over 20 column volumes. Isolated 7-hydroxy-2-methoxy-4-phenylcyclohepta-2,4,6-trien-1-one (19.7 mg, 0.086 mmol) was then dissolved in 33% HBr in acetic acid to a concentration of 0.1M, and heated to 120° C. in a sealed vessel for 1 hr. The reaction was diluted 20 fold with DCM and 0.2M phosphate buffer was added until the pH of the aqueous layer was ~6. The reaction was then extracted 3×DCM and the combined organic extracts dried over $Na_2SO_4$, and the solvent evaporated under reduced pressure to yield a yellow oil. The residue was subjected RP-Flash chromatography using a C18 column and eluting with a linear gradient of 20%-60% acetonitrile in water containing 0.05% trifluoroacetic acid over 20 column volumes. Fractions containing product were redissolved in $CH_2Cl_2$ and treated with saturated aq. $K_2CO_3$. The DCM layer was discarded, then the pH of the aqueous layer was adjusted to ~6, and extracted 3×DCM. The combined organic extracts were dried over $Na_2SO_4$, and the solvent evaporated under reduced pressure to afford pure 2,7-dihydroxy-4-phenylcyclohepta-2,4,6-trien-1-one (5.8 mg, 31% yield). $^1$H NMR (400 MHz, $CDCl_3$) δ 7.80 (s, 1H), 7.56-7.36 (m, 7H). HRMS (TOF MS ES+) m/z Calcd for $C_{13}H_{11}O_3$: 215.0708. Mass Found: 215.0726.

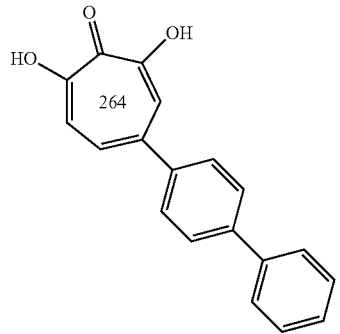 [SMILES: O=c1c(O)ccc(-c2ccc(-c3ccccc3)cc2)cc1O]

VIc. 4-([1,1'-biphenyl]-4-yl)-2,7-dihydroxycyclohepta-2,4,6-trien-1-one (264)

4-bromo-2,7-dihydroxycyclohepta-2,4,6-trien-1-one (s5) (20.7 mg, 0.090 mmol) and 4-biphenyl boronic acid (25 mg, 0.125 mmol) were dissolved in 4.5 mL of 2-propanol. 1.25 mL of 1M aq. $K_2CO_3$ was then added and the solution was purged with Ar for 15 min, and $Pd(PPh_3)_4$ (10.4 mg, 0.009 mmol) was added, and the reaction was stirred in a sealed vessel at 85° C. for 48 hrs. The reaction was poured into water, and extracted 3×DCM. The combined organic extracts were dried over $Na_2SO_4$, and the solvent evaporated under reduced pressure. The product, 4-([1,1'-biphenyl]-4-yl)-7-hydroxy-2-methoxycyclohepta-2,4,6-trien-1-one (9.6 mg, 35% isolated yield), was purified by RP-Flash chromatography using a C18 column and eluting with a linear gradient of 20%-60% acetonitrile in water containing 0.05% trifluoroacetic acid over 20 column volumes. Isolated 4-([1,1'-biphenyl]-4-yl)-7-hydroxy-2-methoxycyclohepta-2,4,6-trien-1-one (9.6 mg, 0.032 mmol) was then dissolved in 33% HBr in acetic acid to a concentration of 0.1M, and heated to 120° C. in a sealed vessel for 1 hr. The reaction was diluted 20 fold with DCM and 0.2M phosphate buffer was added until the pH of the aqueous layer was ~6. The reaction was then extracted 3×DCM and the combined organic extracts dried over $Na_2SO_4$, and the solvent evaporated under reduced pressure to yield a pale yellow oil. The product, 4-([1,1'-biphenyl]-4-yl)-2,7-dihydroxycyclohepta-2,4,6-trien-1-one (1.8 mg, 19% isolated yield), was isolated as an off-white yellow solid by RP-Flash chromatography using a C18 column and eluting with a linear gradient of 20%-60% acetonitrile in water containing 0.05% trifluoroacetic acid over 20 column volumes. $^1$H NMR (400 MHz, $CDCl_3$) δ 7.85 (d, J=1.7 Hz, 1H), 7.74-7.68 (m, 2H), 7.63 (ddd, J=18.6, 10.0, 6.0 Hz, 5H), 7.51-7.43 (m, 3H), 7.39 (ddd, J=7.3, 3.8, 1.2 Hz, 1H). HRMS (TOF MS ES+) m/z Calcd for $C_{19}H_{15}O_3$: 291.1021. Mass Found: 291.1015.

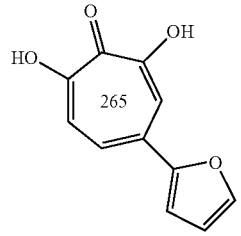 [SMILES: O=c1c(O)ccc(-c2ccco2)cc1O]

VId. 4-(furan-2-yl)-2,7-dihydroxycyclohepta-2,4,6-trien-1-one (265)

4-bromo-2,7-dihydroxycyclohepta-2,4,6-trien-1-one (s5) (19.3 mg, 0.063 mmol) and 2-furan boronic acid (9.8 mg, 0.124 mmol) were dissolved in 3.15 mL of 2-propanol. 0.88 mL of 1M aq. $K_2CO_3$ was then added and the solution was purged with Ar for 15 min, and $Pd(PPh_3)_4$ (7.3 mg, 0.006 mmol) was added, and the reaction was stirred in a sealed vessel at 85° C. for 48 hrs. The reaction was poured into water, and extracted 3×DCM. The combined organic extracts were dried over $Na_2SO_4$, and the solvent evaporated under reduced pressure. The product, 44-(furan-2-yl)-7-hydroxy-2-methoxycyclohepta-2,4,6-trien-1-one (8.8 mg, 48% isolated yield), was purified by RP-Flash chromatography using a C18 column and eluting with a linear gradient of 20%-60% acetonitrile in water containing 0.05% trifluoroacetic acid over 20 column volumes. Isolated 4-([1,1'-biphenyl]-3-yl)-7-hydroxy-2-methoxycyclohepta-2,4,6-trien-1-one (13.1 mg, 0.06 mmol) was then dissolved in 33% HBr in acetic acid to a concentration of 0.1M, and heated to 120° C. in a sealed vessel for 1 hr. The reaction was diluted 20 fold with DCM and 0.2 M phosphate buffer was added until the pH of the aqueous layer was ~6. The reaction was then extracted 3×DCM and the combined organic extracts dried over $Na_2SO_4$, and the solvent evaporated under reduced pressure to yield the product, 4-(furan-2-yl)-2,7-dihydroxycyclohepta-2,4,6-trien-1-one (12.4 mg, >95%) was isolated as a light yellow solid. $^1$H NMR (400 MHz, $CDCl_3$) δ 7.94 (d, J=1.6 Hz, 1H), 7.66 (dd, J=10.9, 1.6 Hz, 1H), 7.54 (s, 1H), 7.52 (d, J=10.9 Hz, 1H,), 6.81 (d, J=3.5 Hz, 1H), 6.53 (dt, J=8.8, 4.4 Hz, 1H). HRMS (TOF MS ES+) m/z Calcd for $C_{11}H_9O_4$: 205.0501. Mass Found: 205.0558.

Figure 11A:
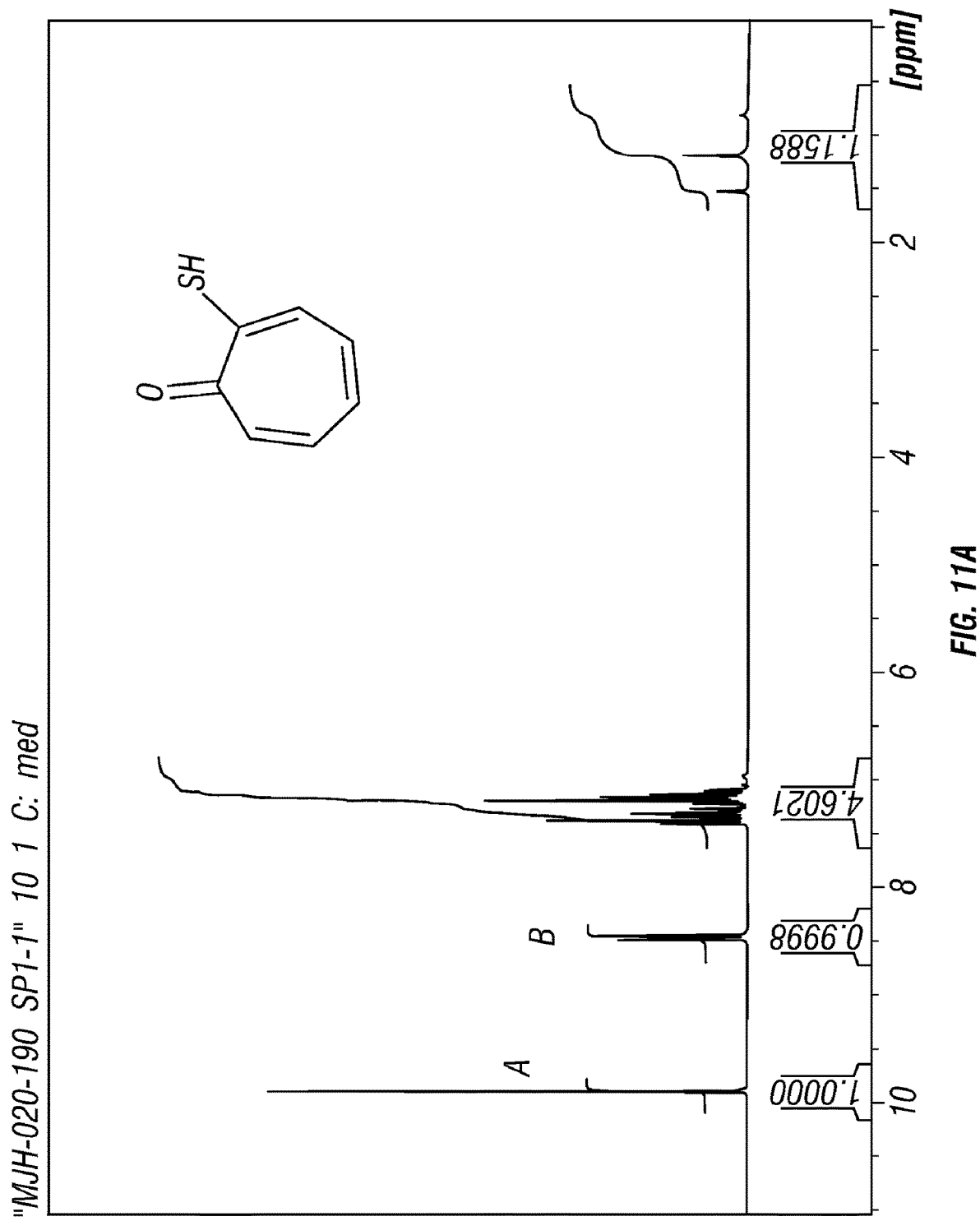
FIGS. 11A-11C show the $^1$H NMR of compounds #363 (FIG. 11A), #364 (FIG. 11B), and #365 (FIG. 11C).
Figure 11B:
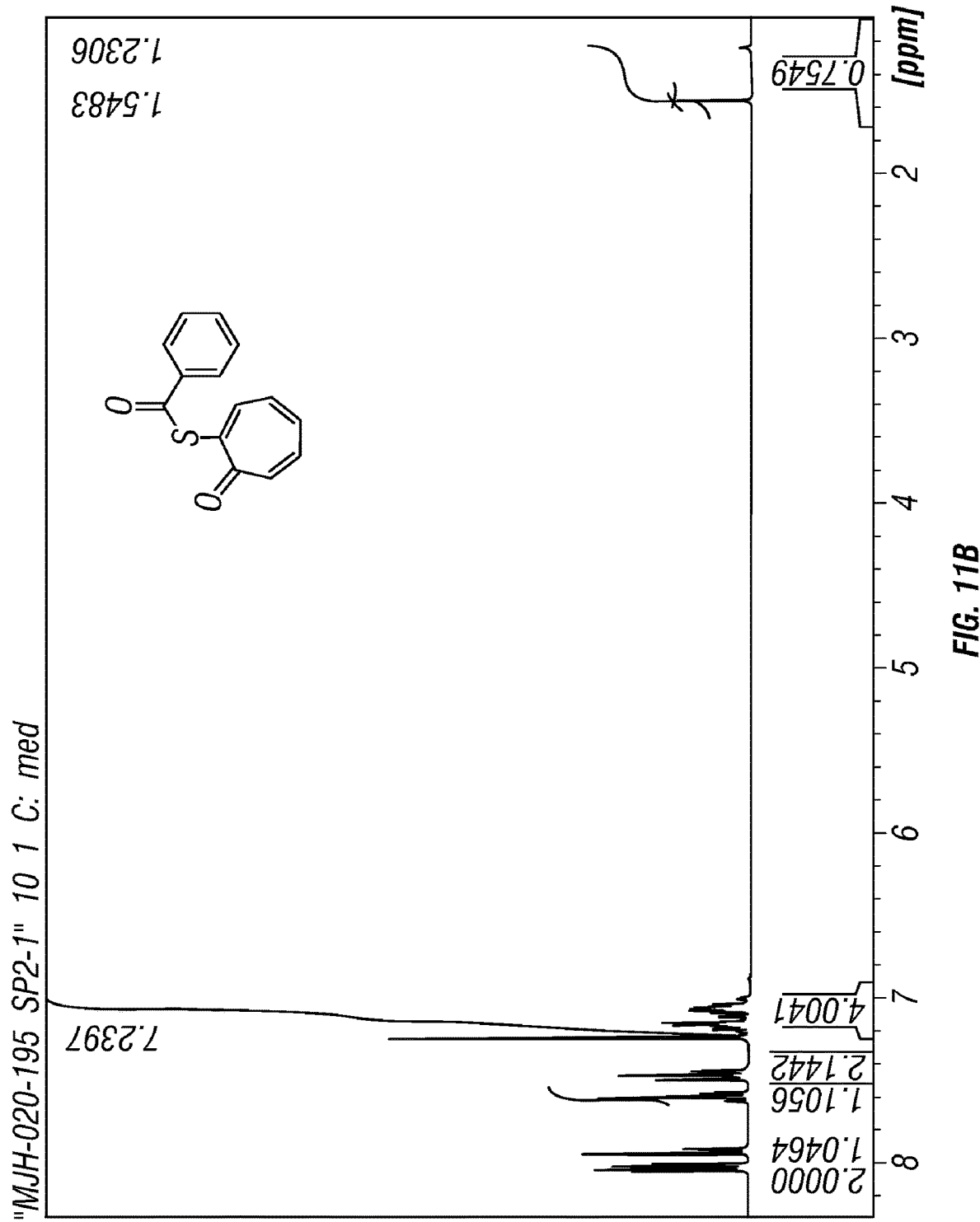
Figure 11C:
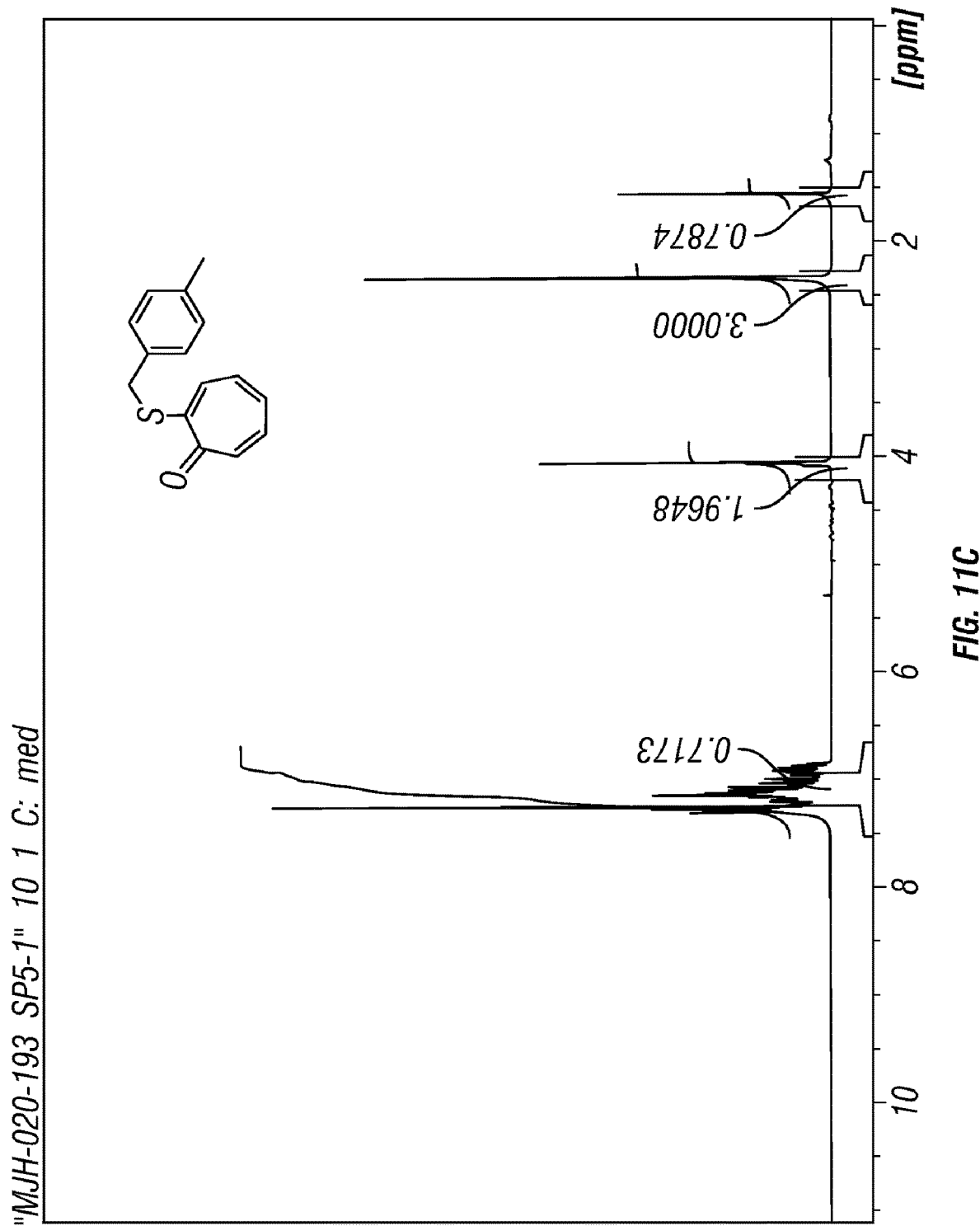

Compounds #363-#365 were synthesized using methods analogous to those described in Machiguchi, et al., 1993;

Nozoe, et al., 1952a, Nozoe, et al., 1952b, Nozoe, et al., 1952c, Nozoe, et al., 1953, Takeshita, et al., 1984, and U.S. Pat. No. 4,066,784. $^1$H NMR spectra for these compounds are shown in FIGS. 11A-11C.

3. Biological Activity

A. Methods

Strains and media. All inhibition assays were performed with *C. neoformans* var *grubii*, KN99 (serotype A, MATα; kindly provided by Jennifer Lodge). Two clinical strains of *C. neoformans* var *grubii*, serotype A, were kindly provided by Tamara Doering and Andre Spec. Cells were passaged on YPD (1% yeast extract, 2% yeast peptone, 2% dextrose) agar plates and grown overnight at 30° C. in YPD liquid media prior to dilution for the limiting dilution assays to determine the minimal inhibitory concentration (MIC) of inhibition. YNB-02 (0.67% yeast nitrogen base, 0.2% dextrose, pH 7.0 with 50 mM MOPs) was used for all limiting dilution inhibition assays unless otherwise noted. cRPMI is RPMI-1650 (Sigma) with glutamine+0.625% fetal bovine serum.

Compound Acquisition and Synthesis.

Figure 4A:
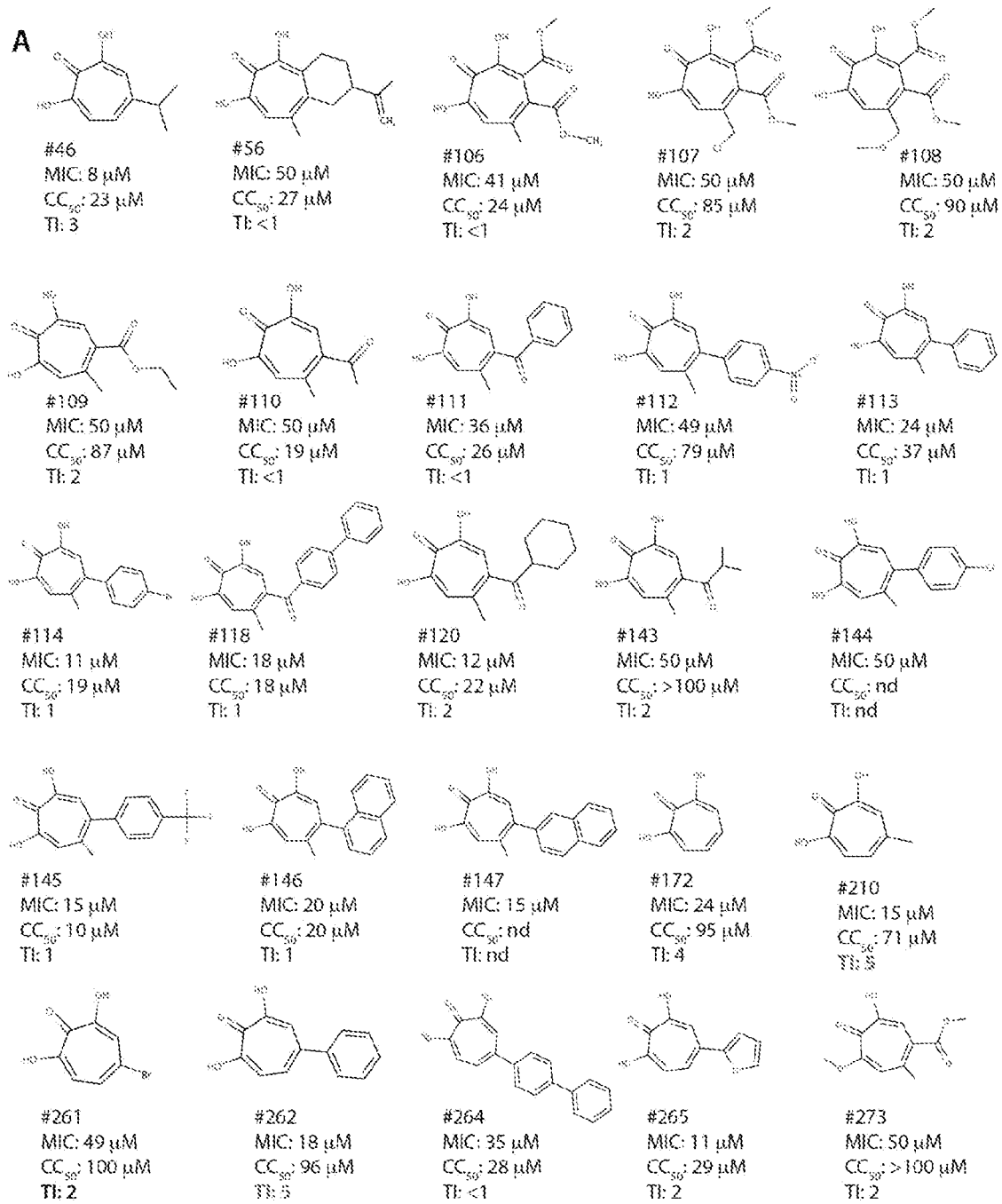
FIGS. 4A-4C. Structures of α-hydroxytropolones, α-methoxytropolones, and other tropolones.
Figure 4B:
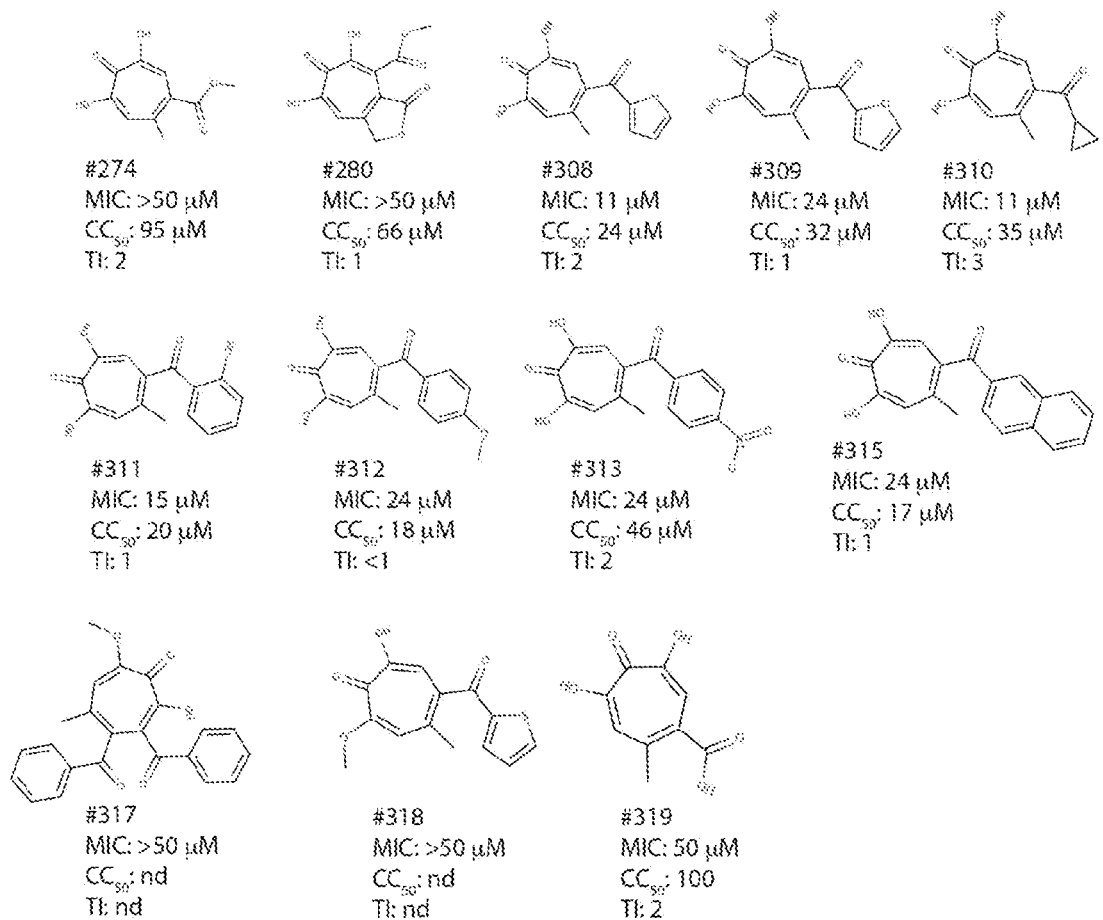
Figure 4C:
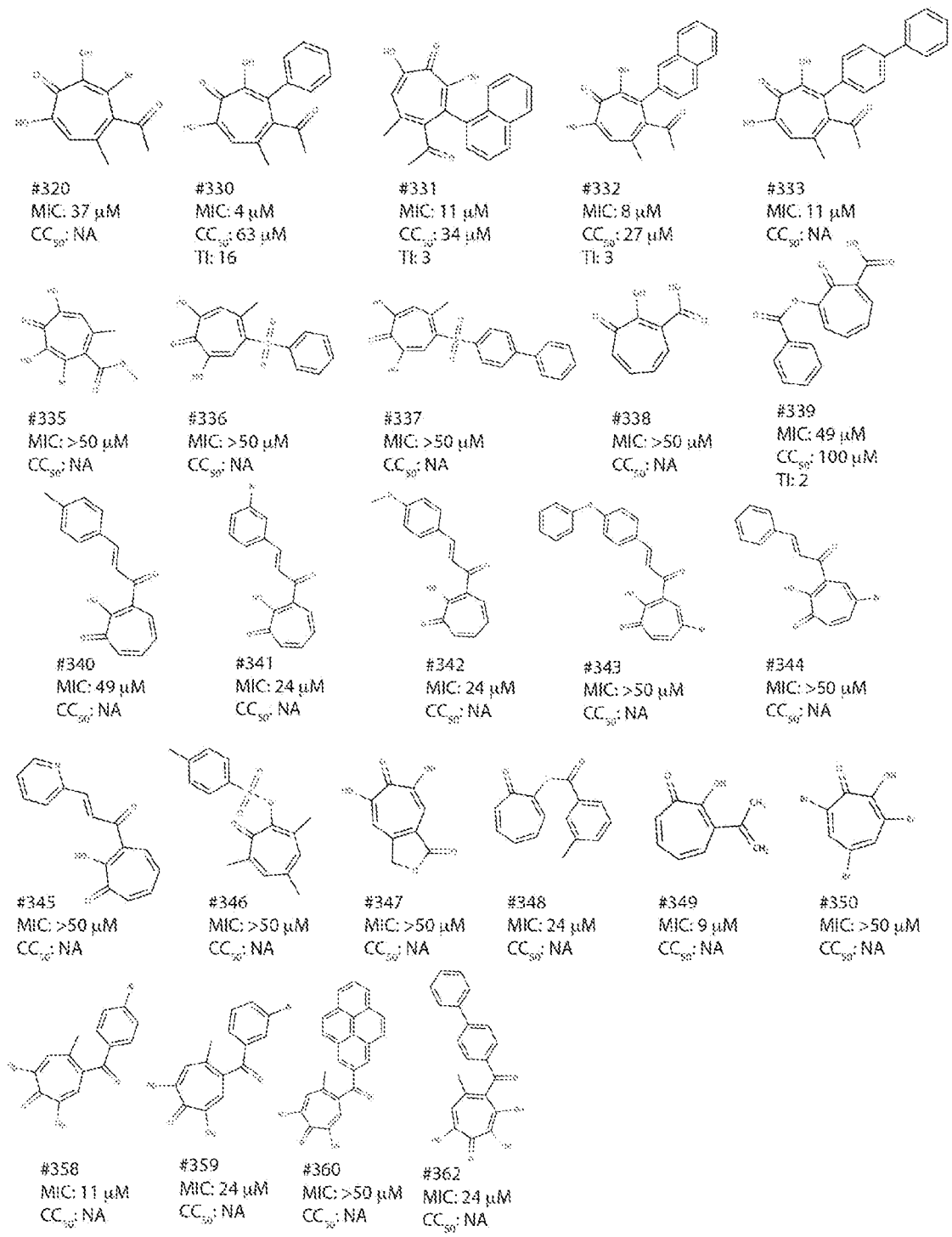

The compounds employed are in Table 2 and their structures are in FIGS. 4 & 5. Compounds #46-57 and 195 were acquired from the National Cancer Institute (NCI) Developmental Therapeutics Program. Compounds #60-63, 281-285 and 305 were purchased. α-Hydroxytropolone (compound #172) was synthesized in 3 steps from tropolone based on the procedure of Takeshita et al. Compounds #106-120, 143-147, and 273-274 were synthesized in 5 to 7 steps from kojic acid as previously described (Ireland et al., 2016, Meck et al., 2012, Williams et al., 2013, Hirsch et al., 2014 and D'Erasmo et al., 2016). Compounds #280, 308-313, 315, and 317-319 were synthesized using an analogous strategy and are described above. Compounds #261-264 were made from 1,4-cyclohexadiene using the Banwell αHT synthesis method (Amon et al., 1987 and Banwell et al., 1991) and specifics of these synthesis can be found above. Compounds were ≥95% pure by $^1$H NMR analysis. The compounds were dissolved in dimethyl sulfoxide (DMSO) and stored at −80° C.

Inhibition of *C. neoformans* Growth.

Compounds were tested in a limiting dilution assay with a starting optical density (650 nM) of 0.001 in YNB-02+1% DMSO. Cells were incubated without shaking for 48 hours at 35° C. and cell density was measured at 650 nM. The minimal inhibitory concentration (MIC) was determined using compound concentrations from 0.19 to 50 μM of the compound in YNB-02+1% DMSO. Each assay was done in triplicate and all values are the average of two or more independent assays. The data are presented as the average cell density as a percent of DMSO-only treated cells. MICs are reported as the minimal concentration needed to inhibit 80% of *C. neoformans* growth relative to vehicle-treated controls.

Cytotoxicity in Hepatoma Cells.

HepDES19 cells (1.0×10$^4$ cells per well) were seeded in 96-well plates and incubated in DMEM with 10% fetal bovine serum (FBS) plus 1% penicillin and streptomycin, 1% nonessential amino acids, and 1% glutamine. The compounds were diluted in the medium at concentrations ranging from 0.78 to 100 μM plus 1% DMSO and added to the cells 48 hours after plating, with each concentration tested in triplicate. Cells were incubated with the compound for 72 hours and cytotoxicity was measured using a mitochondrial metabolic assay with MTS (Promega). The data were transformed to log[inhibitor] and fit to a 4-variable slope curve using GraphPad Prism (v6, www.graphpad.com). The concentration at which 50% of cells were inhibited relative to vehicle-treated control is reported as the $CC_{50}$ value.

Synergy Assay.

The minimal inhibitory concentration (MIC) of compounds #54 and #284 were measured in combination with Fluconazole (FLC) and Amphotericin B (AMB) in a checkerboard assay (White, et al., 1996; Banerjee, et al., 2014). The MICs of #54, FLC and AMB were measured using compound concentrations from 0.19 to 50 μM, while the MIC of #284 was measured using concentrations from 0.04 to 10 μM. Each assay was performed in triplicate and all values are the average of two or more independent assays. The fractional inhibitory concentration index (FICI) model is expressed as $\Sigma FIC=FIC_A+FIC_B=MIC_A/MIC_{A'}+MIC_B/MIC_{B'}$, where $MIC_A$, and $MIC_B$ are the MIC values of agents A and B used alone and $MIC_{A'}$ and $MIC_{B'}$ are the MICs of agents A and B used in combination. The interaction between FLC or AMB and the test compounds was interpreted as synergistic when FICI was ≤0.5, as indifferent when FICI was between >0.5 and 4 and as antagonistic when FICI was >4 (Berenbaum, 1978; Odds, 2003).

Fungicidal Assay.

To test for fungicidal activity, aliquots of cells were removed after 48 hours of growth in the presence of test compounds at 2×, 4×, and 8× the respective MICs and spotted them on YPD plates. The plates were incubated at 30° C. for 2 days and checked for growth. Growth of cells treated with test compounds was compared to FLC-treated cells, which is known to be fungistatic and to AMB-treated cells, which is known to be fungicidal (Klepser, et al., 1998; Mesa-Arango, et al., 2014).

Hydrolysis of Compound #284.

To hydrolyze #284, 0.1 M NaOH was added to a solution of 10 mM #284 to 20 mM. The solution was mixed by vortexing until a prominent color change (pale yellow to dark orange) was apparent. This reaction was performed in triplicate. One aliquot of the reaction mixture was stored at room temperature, one at 35° C., and one at 40° C. After 24 hours, the reaction mixtures were neutralized with HCl. MIC assays were prepared in triplicate for each aliquot in a dilution series from 0.19-50 μM. Assays were incubated for 48 hours at 35° C., and cell density was measured at 650 nm.

Growth in Capsule-Inducing Conditions.

KN99α cells were grown overnight in YPD at 30° C. with shaking. The cells were diluted to an $OD_{650}=1$ in YNB-02 or cRPMI, then diluted 1:100 in YNB-02+1% DMSO or cRPMI+1% DMSO and incubated with the compounds at 37° C.+5% $CO_2$ for 48 hours. Capsule was visualized using bright-field microscopy as a halo surrounding the yeast cell through India ink exclusion.

B. Results

Development of a *C. neoformans* Growth Inhibition Assay.

Figures 5A, 5B:
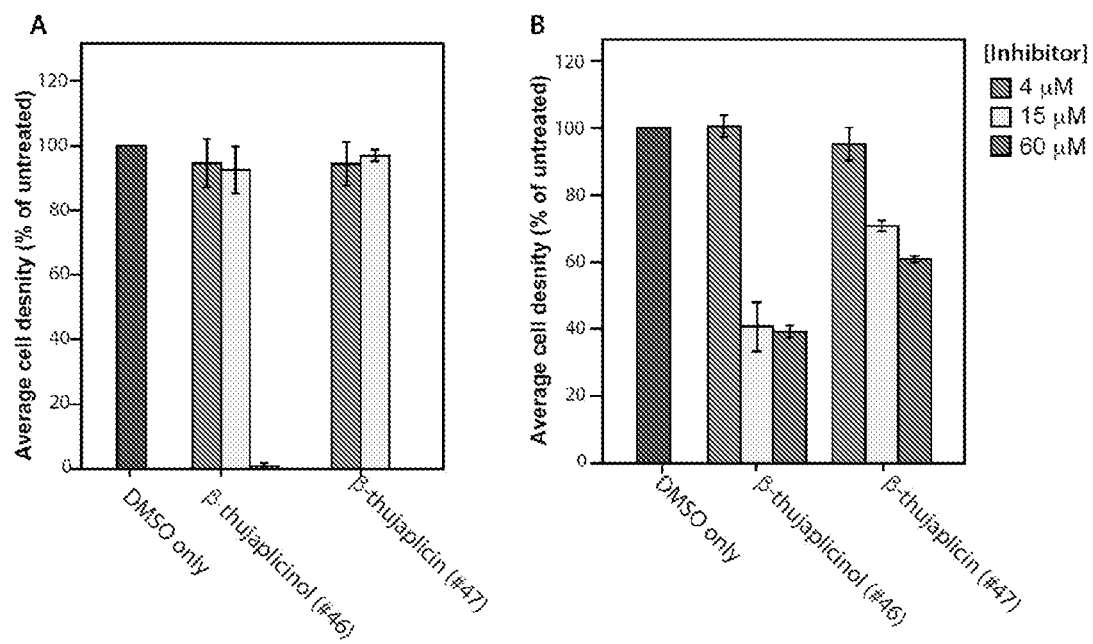
FIGS. 5A & 5B. Inhibition of KN99α cells by β-thujaplicinol and β-thujaplicin under conditions (FIG. 5A) YPD at 25° C.

An assay was developed that could cheaply and reproducibly measure inhibition of *C. neoformans* growth using a 96-well format. *C. neoformans* growth was initially tested in YPD versus YPD+1% DMSO at 25° C. with shaking for 24 and 48 hours. The DMSO-treated cells showed a significant growth lag for the first 24 hours but caught up with untreated cells after 48 hours, resulting in more consistent and higher levels of cell growth. Inhibition was tested with β-thujaplicin and β-thujaplicinol in YPD+1% DMSO at 25° C. at 3.75, 15 and 60 μM and demonstrated that they almost completely inhibited C. neoformans growth at 60 µM (FIG. 5A). However, these conditions are unlike conditions encountered by C. neoformans in mammalian infections, where nutrients are limited, and the pH and temperature are higher than in YPD media. The cryptococcal stress response to low glucose and high pH and temperature may alter its susceptibility to the inhibitors. It is also possible that the enzymes targeted by the inhibitors may render the cell temperature sensitive when inhibited. To better mimic growth in mammals, growth was tested without shaking in nutrient-limited media at 35° C. First, the cell culture media, RPMI-1640+0.4% glucose+1% DMSO (Sigma) as defined by National Committee for Clinical Laboratory Standards (NCCLS) was tested for anti-fungal susceptibility testing. However, the cells grew very poorly under these conditions. Then, growth in YNB (pH 7.0) with 0.2% glucose+1% DMSO without shaking at 35° C. was tested, which has been identified as an appropriate substitute for C. neoformans susceptibility testing (Ghannoum et al., 1992), and saw more consistent cell growth over the 48-hour assay. β-thujaplicin and β-thujaplicinol were tested at 3.75, 15 and 60 µM in YNB-02+1% DMSO at 35° C. and observed some inhibition at 15 and 60 µM (FIG. 5B), but did not observe the nearly complete lack of growth at 60 µM as was observed in YPD at 25° C. (FIG. 5A). However, as the nutrient-limited media and higher temperature is more similar to mammalian cell growth conditions, these conditions were used for all further assays.

Determination of the Minimal Inhibitory Concentration (MIC) for Troponoids.

Figure 3:
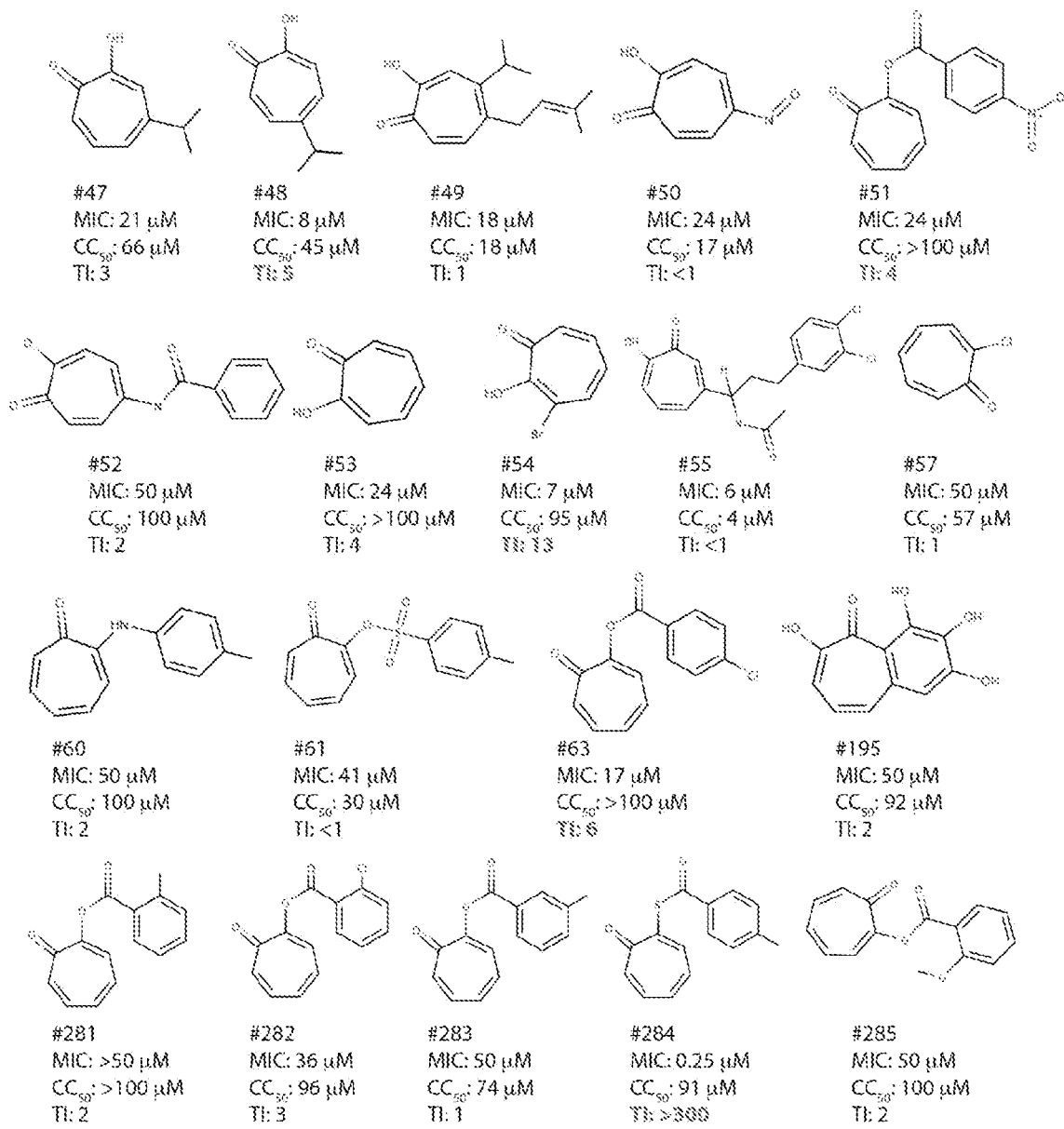
FIG. 3. Structures of tropones and tropolones.

Since only 56 troponoids (Table 2, FIGS. 3 & 4) were available to test, MICs were determined for all compounds to provide an accurate measure of the inhibitory potential of the compounds. The MIC was measured by employing the limiting dilution assay, and defined the MIC as the concentration at which cells were inhibited ≥80% relative to vehicle-treated cells. All values were measured at least two times in independent experiments and the average MIC is reported.

TABLE 2

Compound Activity

| Compound Number | Name/Catalog number | $MIC_{80}$ (µM) | $CC_{50}$ (µM) | TI |
|---|---|---|---|---|
| Tropones | | | | |
| 57 | 2-chlorotropone | 50 | 57.0 | 1 |
| 60 | Chembridge 5942159 | 50 | >100 | 2 |
| 61 | Chembridge 5940946 | 41 | 30.5 | <1 |
| 63 | Chembridge 5938894 | 17 | 100.0 | 6 |
| 281 | Chembridge 5947055 | 50 | 100.0 | 2 |
| 282 | Chembridge 5942369 | 36 | 96.5 | 3 |
| 283 | Chembridge 5940028 | 50 | 74.0 | 1 |
| 284 | Vitas-M Lab STK526992 | 0.25 | 91.0 | >300 |
| 285 | Sigma 378400 | 49 | >100 | 2 |
| Tropolones | | | | |
| 47 | β-thujaplicin | 21 | 66.5 | 3 |
| 48 | γ-thujaplicin | 8 | 45.0 | 5 |
| 49 | Nootkatin | 18 | 18.5 | 1 |
| 50 | 5-nitrosotropolone | 24 | 17.5 | 1 |
| 51 | tropolone p-nitrobenzoate | 24 | >100 | 4 |
| 52 | NSC 79556 | 50 | >100 | 2 |

TABLE 2-continued

Compound Activity

| Compound Number | Name/Catalog number | $MIC_{80}$ (µM) | $CC_{50}$ (µM) | TI |
|---|---|---|---|---|
| 53 | Tropolone | 24 | 100.0 | 4 |
| 54 | 3-bromotropolone | 7 | 95.0 | 13 |
| 55 | NSC 282885 | 6 | 4.3 | <1 |
| 195 | Purpurogallin | 50 | 92.0 | 2 |
| α-hydroxytropolones | | | | |
| 46 | β-thujaplicinol | 8 | 23.0 | 3 |
| 56 | Manicol | 50 | 27.0 | <1 |
| 106 | CM1012-6a | 41 | 24.5 | <1 |
| 107 | CM1012-6b | 50 | 85.5 | 2 |
| 108 | CM1012-6c | 50 | 90.5 | 2 |
| 109 | CM1012-6d | 50 | 87.5 | 2 |
| 110 | CM1012-6e | 50 | 19.0 | <1 |
| 111 | CM1012-6f | 36 | 26.3 | 1 |
| 112 | CM1012-6i | 49 | 74.0 | 1 |
| 113 | RM-YM-1-0613 | 24 | 37.5 | 2 |
| 114 | RM-YM-2-0613 | 11 | 18.6 | 1 |
| 118 | RM-MD-2-0813 | 18 | 17.5 | 1 |
| 120 | RM-MD-1-0713 | 12 | 21.5 | 2 |
| 143 | MD-1-138 | 50 | >100 | 2 |
| 144 | DH-1-148 | 50 | nd | |
| 145 | DH-1-163 | 15 | 11.0 | 1 |
| 146 | DH-2-8 | 20 | 20.0 | 1 |
| 147 | DH-2-4 | 15 | 13.1 | 1 |
| 172 | 7-Hydroxytropolone | 24 | 100.0 | 4 |
| 210 | MolMoll 19617 | 15 | 71.0 | 5 |
| 261 | AG40 | 49 | 100 | 2 |
| 262 | AG51 | 18 | 96.0 | 5 |
| 264 | AG44 | 35 | 28.0 | <1 |
| 267 | AG59 | 24 | 17.0 | <1 |
| 273 | DH-4-116 | 50 | 100.0 | 2 |
| 274 | DH-4-117 | 50 | 92.5 | 2 |
| 280 | AG77 | 50 | 66.0 | 1 |
| 308 | AG-II-18-P | 11 | 24.0 | 2 |
| 309 | AG-I-183-P | 24 | 35.0 | 1 |
| 310 | AG-II-21-P | 11 | 35.0 | 3 |
| 311 | AG-II-3-P | 15 | 20.0 | 1 |
| 312 | AG-II-4-P | 18 | 18.0 | 1 |
| 313 | AG-II-5-P | 24 | 46.0 | 2 |
| 315 | AG-I-186-P | 24 | 17 | 1 |
| 317 | AG-II-22-P | 50 | >100 | 2 |
| 318 | AG-II-17-P | 50 | nd | |
| 319 | AB-1-111 | 50 | >100 | 2 |

The library consists of tropolone (#53), which had moderate activity (MIC=24 µM), and derivatives thereof. Eight of the tropolone analogs had moderate substitution on the tropone ring (#47-50, 52, 54, 55, 195), and were for the most part at least as good as tropolone itself, with three of these seven compounds (#48, 54, 55) having MIC values almost three-fold lower than #53, and only two (#52 and 195) showing decreased activity. Another ten of the troponoids tested were variants of #53 with modifications to the tropolone hydroxyl or —OH, and most of these had decreased activity, such as compounds with a change to a chlorine (#57), an aniline (#60), and a sulfonyl ester (#61). The activity of several benzoylated variants (#51, 63, 281-283, 285) seemed to be impacted by the electronics of the phenyl ring: Those with electron-donating groups (#281, 283, 285) had higher MIC values, whereas those with electron-withdrawing groups (#51, 63, 282) had values more similar to tropolone. By far the most potent inhibition of C. neoformans growth was observed when the tropolone hydroxyl or —OH was instead a thioester (#284), which led to activity 100-fold more potent than tropolone.

Figures 10A, 10B:
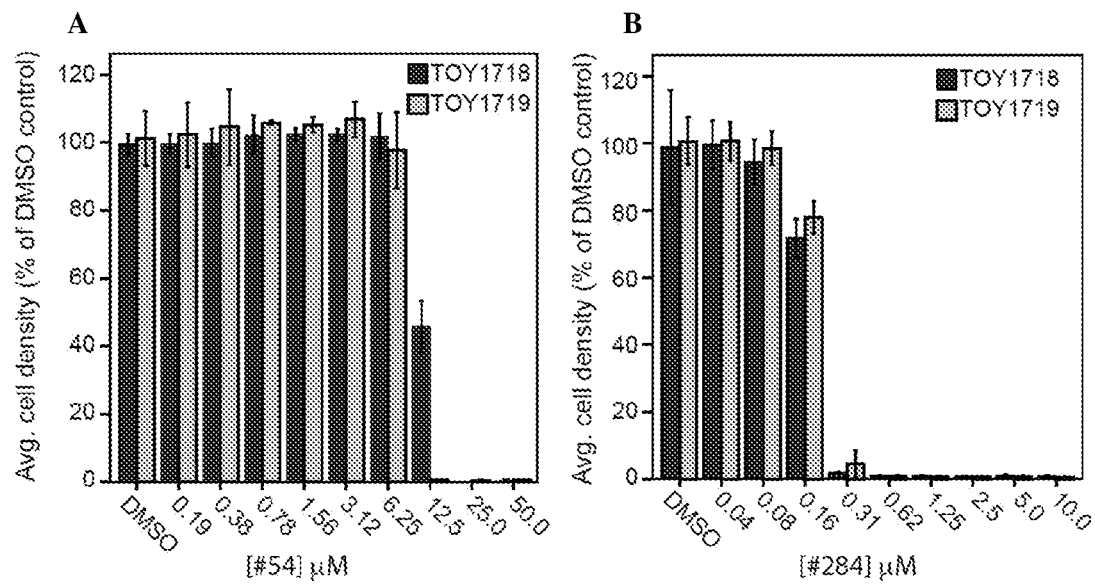
FIGS. 10A & 10B show the activity of compound #54 (FIG. 10A) and compound #284 (FIG. 10B) in a clinically relevant cell line.

Another thirty-seven of the molecules are αHTs (FIG. 4), which have a third contiguous oxygen atom on the troponoid ring. The αHT with no substitutions (#172) had an MIC of 24 µM, which was consistent with tropolone (#54), demonstrating these are likely comparable as a starting pharmacophore. Six of the molecules tested had substitution at only C4 (#46, 210, 260, 262, 264, 265) and half of these (#46, 210, 265) had activity ≤15 µM. Of note, β-thujaplicinol (#46) and β-thujaplicin (#48) share a common isopropyl appendage and had comparable activities. Five of the αHTs had substitution at C4, C5, and C6 (#56, 106-108 and 280) and all had higher MICs than #172. Most of the synthetic αHTs made through the previously described synthetic strategy (Meck et al., 2012, Williams et al., 2013 and D'Erasmo et al., 2014) had a methyl substitution at C5 and varied at C4 with the tropolone directly linked to an aromatic (#112-114, 144-147) or a carbonyl functional group (#109-111, 118, 120, 143, 308-313, 315, 319). Most of these molecules had MIC values higher than #172, although four of the 14 carbonyl-appended compounds (#118, 120, 310 & 311), and three of the seven aromatic-linked compounds (#114, 145, 147) were slightly more potent. Three additional α-methoxytropolones, (#172, 317, 318), synthetic precursors to αHTs, were also tested, and these had little activity. The MIC of two of hits, #54 and #284, was measured in two independent clinical strains and confirmed that these compounds showed very similar levels of inhibitor activity, with a MIC of 6-12 µM for #54 and a MIC of 0.16-0.32 µM for #284. (FIGS. 10A & 10B).

Hydrolyzed Compound #284 Remains Active.

Figure 6:
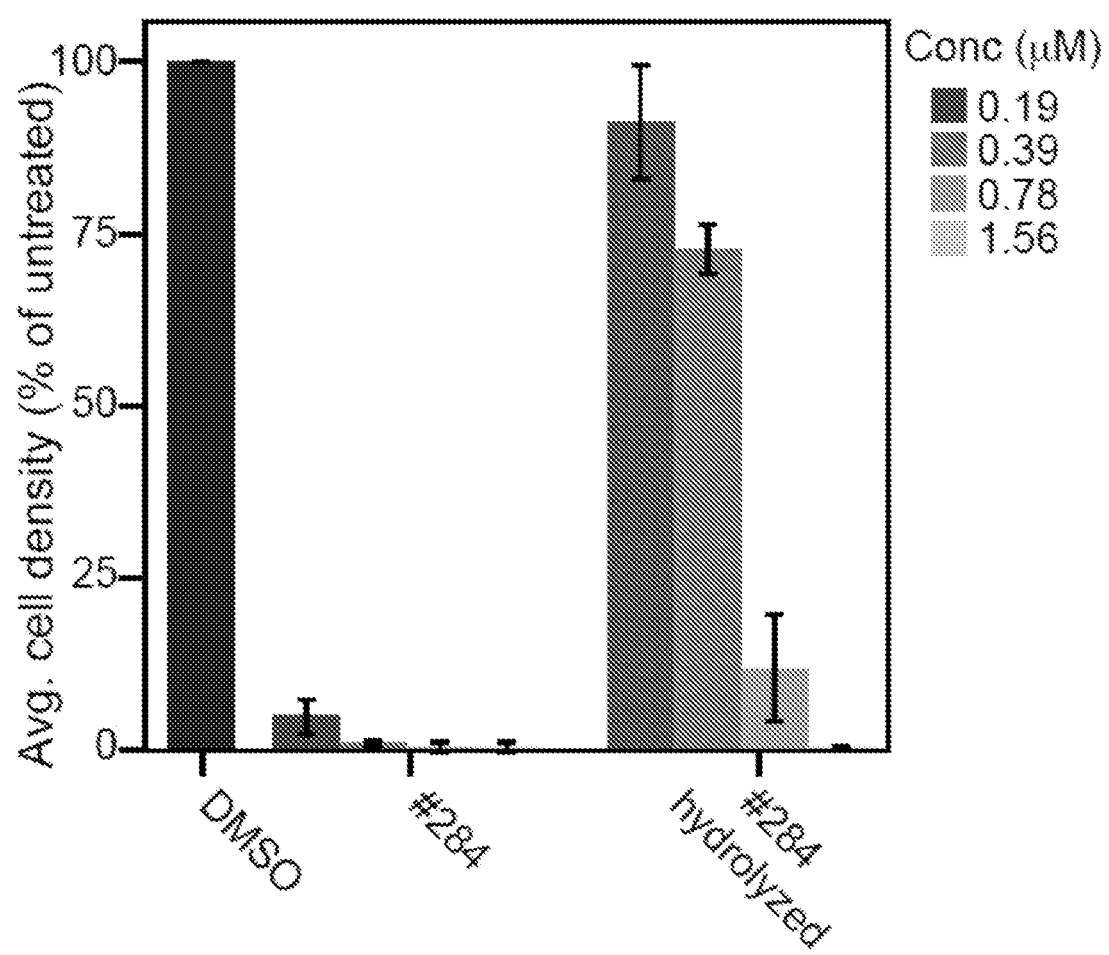
FIG. 6. Inhibition of KN99α cells with #284 or hydrolyzed products of #284 measured by cell density after 48 hours at 35° C. in YNB-02+1% DMSO. Values are mean±standard deviation from three replicates.

Compound #284 (FIG. 3) has a labile thioester linkage that is likely to be hydrolyzed in vivo. This would release a tropothione, possibly in multiple oxidation states, as well as p-benzoic acid, any of which could potentially act as inhibitors. Tropothione was not available commercially for testing for inhibition of *C. neoformans*, but p-benzoic acid was tested as well as the hydrolysis products of #284 in MIC assays. p-Benzoic acid did not inhibit fungal growth up to 50 µM whereas the hydrolyzed products were able to inhibit growth with an MIC of 0.78 µM (FIG. 6). The hydrolysis products of #284 were analyzed by mass spectrometry and observed the loss of the starting material, but could not resolve the hydrolysis products. The fact that the hydrolysis products still inhibited *C. neoformans* growth whereas p-benzoic acid did not suggests that tropothione or oxidized derivatives of tropothione are effective inhibitors of *C. neoformans* growth.

Inhibition Under Capsule-Inducing Conditions.

Figures 7A, 7B, 7C, 7D:
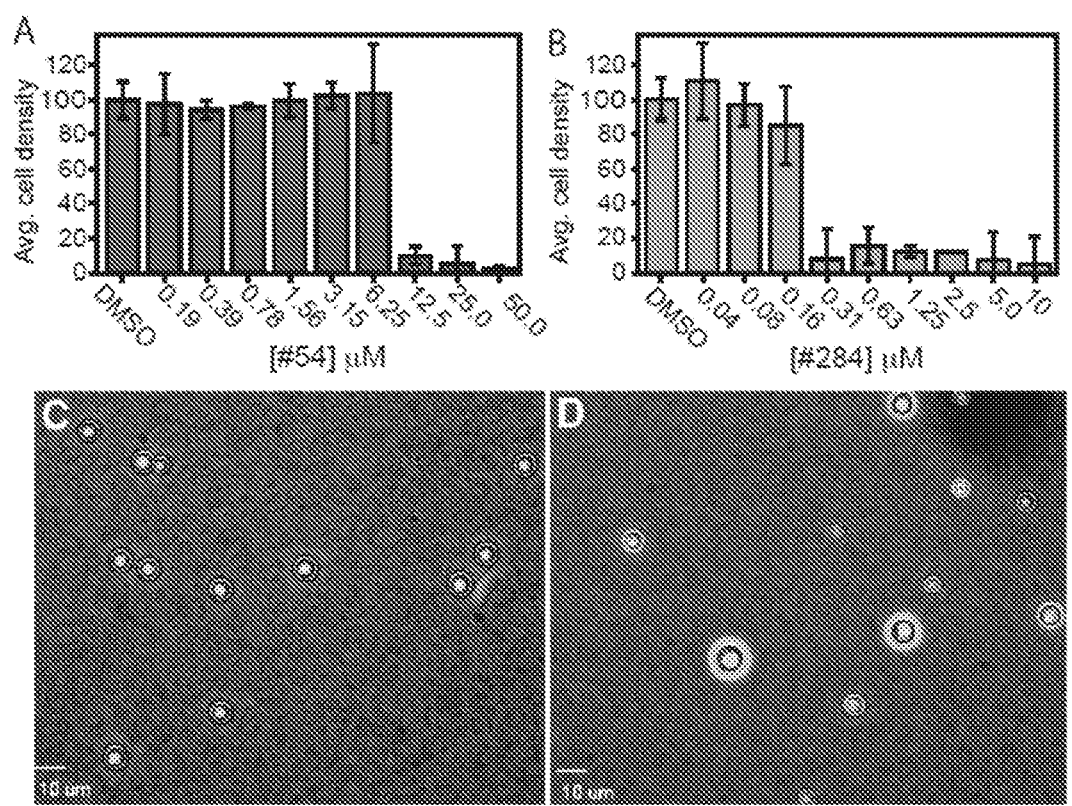
FIGS. 7A-7D. Inhibition of KN99α cells as measured by cell density after 48 hours at 37° C.+5% CO$_2$ in YNB-02+1% DMSO for (FIG. 7A) #54 or (FIG. 7B) #284. Values are mean±standard deviation from three replicates. India ink exclusion assay of capsule production of the cells cultured in (FIG. 7C) YPD or (FIG. 7D) YNB-02+1% DMSO at 37° C.+5% CO$_2$. Scale bar: 10 µm.

The screening was conducted in the nutrient-limited media YNB-02 at 35° C. to mimic some aspects of the growth conditions in humans. However, it is possible the compounds may demonstrate less potency under conditions that induce the cryptococcal yeast cells to elaborate a polysaccharide capsule (Doering, 2009). Two hits (FIG. 3, #284, 54) were tested under conditions that induce capsule elaboration: nutrient limiting, 37° C. and 5% $CO_2$. MICs for #54 and #284 were measured in cells grown for 48 hours in either YNB-02+1% DMSO or RPMI+1% DMSO at 37° C. with 5% $CO_2$. No growth was observed in RPMI under these conditions, but cells did grow in YNB-02. The MIC for #54 was between 6 and 12 µM (FIG. 7A) while the MIC for #284 was between 0.16 and 0.31 µM (FIG. 7B). The untreated cells grown in YNB-02 were able to elaborate the capsule (FIG. 7D) compared to cells grown overnight in YPD at 30° C. (FIG. 7C). The MICs for #54 and #284 were only slightly higher when cells were grown under conditions that elaborate the capsule, suggesting the capsule induction does not block the inhibitors from entering the cells or substantially impair their activity.

Compounds #54 and #284 are not Antagonistic with Fluconazole or Amphotericin B.

An important consideration of any new antifungal is whether it will be compatible with existing antifungal therapies. Therefore, the MICs of AMB, FLC, #54 and #284 were measured alone and in combination. The MIC at which 80% of cells were inhibited relative to vehicle-treated cells was 3 µM (0.9 µg/mL), 1.5 µM (1.4 µg/mL), 12 µM and 0.31 µM for FLC, AMB, #54 and #284 respectively. These values remained unchanged for either #54 or #284 when used in combination with either FLC or AMB. This results in FIC values of 1 for each compound in combination with either FLC or AMB and an FIC index of 2. Thus, interaction of the combination of either #54 or #284 with either FLC or AMB shows indifference (Odds, 2003). Importantly, neither #54 nor #284 was antagonistic when used in combination with FLC or AMB.

Figures 8A, 8B, 8C, 8D, 8E, 8F:
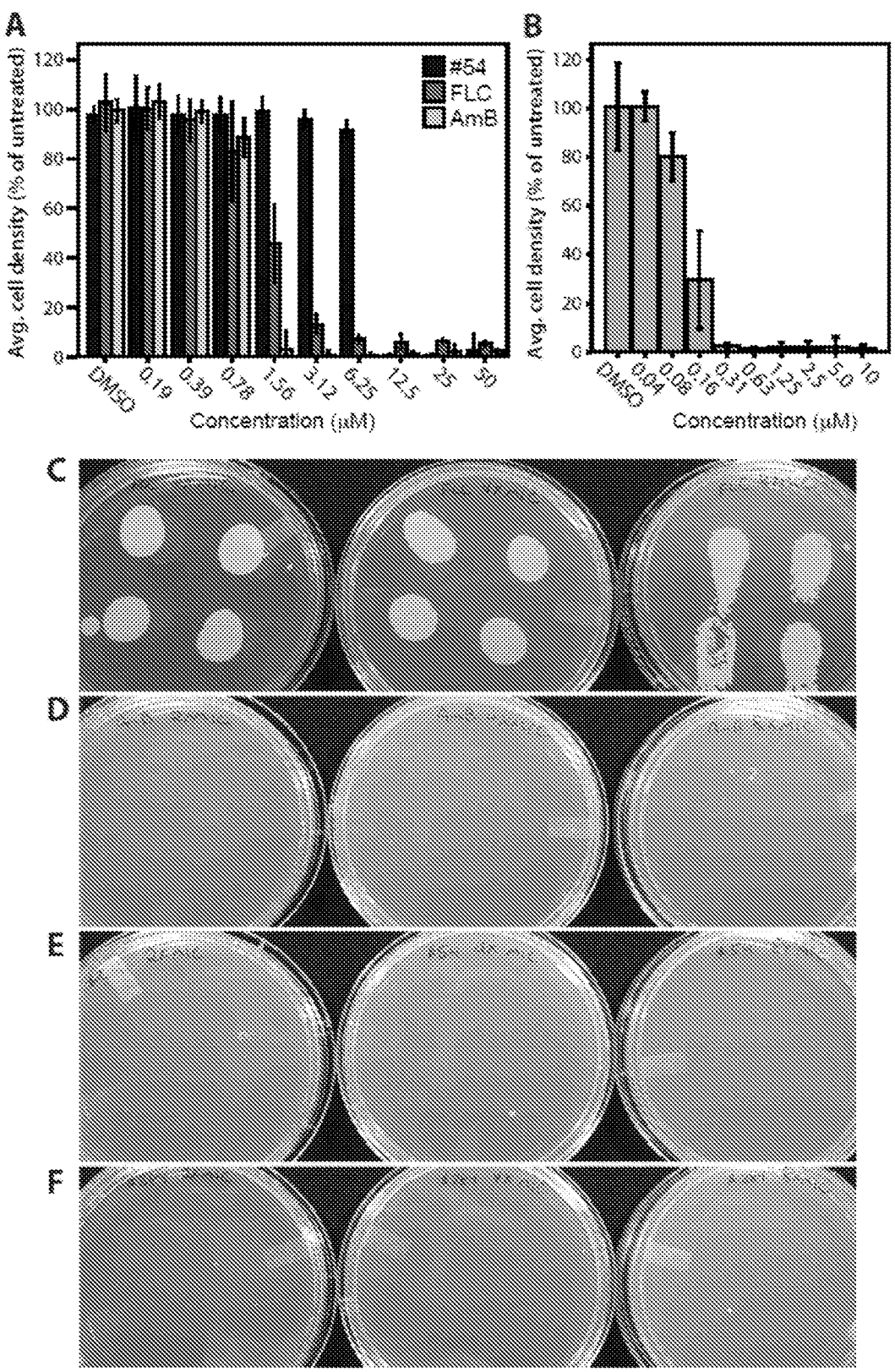
FIGS. 8A-8F. KN99α cells were treated with (FIGS. 8A & 8B) FLC, AmB, #54, and #284 at 0.19, 0.39, 0.78, 1.56, 3.12, 6.25, 12.5, 25 and 50 µM showing the average cell density as a percentage of the untreated cells.

Tropolones are Fungicidal.

compounds #54 and #284 were evaluated for fungicidal versus fungistatic activity. This analysis was done in a qualitative assay in parallel with FLC, which is known to be fungistatic (Klepser, et al., 1998) and AMB, which is known to be fungicidal (Mesa-Arango, et al., 2014). The MICs were 3 µM (0.9 µg/mL), 1.5 µM (1.4 µg/mL), 12 µM and 0.31 µM for FLC, AMB, #54 and #284 respectively. (FIGS. 8A & 8B). Following drug exposure for 48 hours, 30 µL of each of the remaining replicate cultures at 2×, 4× and 8× the MIC were spotted on YPD plates and incubated at 30° C. for 2 days. Significant cell growth was observed for FLC-treated cells up to 8× the MIC (FIG. 8C) whereas no cell growth was observed for AMB-, #54- or #284-treated cells at 2-8× the MIC (FIGS. 8D-8F). Based on these data, it was concluded that both #54 and #284 are fungicidal against *C. neoformans*.

Cytotoxicity in Mammalian Cells.

Finally, the ability of key *C. neoformans* inhibitors to induce cytotoxicity in mammalian cells was tested to begin evaluating potential use of troponoids as antifungals in humans. HepDES19 cells were chosen because they are a derivative of the HepG2 hepatoblastoma cell line that is commonly used for initial evaluation of potential hepatocytoxocity (Guo et al., 2007). Cytotoxicity was measured using an MTS assay that measures mitochondrial function because some troponoids have been reported to reduce mitochondrial function Tavis et al., 2013) and because the MTS assay has been the most sensitive of the assays we have employed to identify potential adverse effects on function of mammalian cells for this compound class.

HepDES19 cells were treated with medium carrying varying concentrations of key *Cryptococcus* inhibitors and select additional compounds for comparison in a final concentration of DMSO of 1%. Three days later, the MTS reagent was added for 90 minutes prior to terminating the incubation period and reading the $OD_{480}$. We measured fifty percent cytotoxicity values ($CC_{50}$s) for 52 of the 56 compounds, and the $CC_{50}$ values ranged from 4 to >100 µM (Table 2). The tropones were relatively non-toxic, with the lowest $CC_{50}$ being 30.5 µM for #61. Of the 10 tropolones, 3 had $CC_{50}$ values ≤20 µM, with #55 being the most toxic with a $CC_{50}$ of 4 µM. The αHTs had a range of toxicity from 11 to >100 mM. 23 of the 32 αHTs tested had $CC_{50}$ values >20 µM.

Comparing the MIC and $CC_{50}$ data permitted calculation of a therapeutic index (TI, $CC_{50}$/MIC) for the *Cryptococcus* inhibitors. TI values for most of the tropolones were fairly low, with TIs for 30 of the 32 compounds being <8. However, promising TI values >8 were found for two compounds, #54 and #284, most notably the TI of >300 that was observed for #284.

Therefore, substantial cytotoxicity could be induced by most of the troponoids in a liver-derived cell line, but at least one compound, #284, had a high TI value of >300 that opens a window for development of it into a potentially clinically useful cryptococcal inhibitor.

C. Discussion

Tropolone bioactivity is often associated with the ability to bind to and inhibit metalloenzymes (Jacobsen et al., 2010 and Nakano et al., 2015). This binding takes place through bidentate chelation of the metal between the tropolone carbonyl and the tropolone OH, which is likely deprotonated at physiological pH and enhances coordination to the metal center (Jacobsen et al., 2007). As such, if the activity against *C. neoformans* were due to similar metalloenzyme inhibition, modifications to this hydroxyl would be expected to result in a loss of activity. Indeed, most analogs modified at this group led to decreased or complete loss of activity, such as the change to a chloride (#57), aniline (#60) or sulfonyl ester (#61), as well as several benzoylated analogs (#281, 283, 285). Benzoylated derivatives with an electron-withdrawing appendage (#51, 63, 282), however, did maintain activity comparable to tropolone (#53). Since electron-withdrawing groups would destabilize the carbonyl ester, it is possible that these molecules are hydrolyzing in the assays, although further tests are needed to evaluate this hypothesis.

The most potent inhibitor was compound #284, which had the lowest MIC (0.2 µM) and best TI of all compounds tested. The presence of the high-energy thioester linkage strongly suggests that this molecule is hydrolyzed within cells or in the growth medium. Hydrolysis of #284 would likely result in release of p-benzoic acid and tropone with a free sulfhydryl group (thiotropolone) that may react with free cysteines in enzymes or attenuate the metal-binding abilities of the troponoid. The p-benzoic acid by itself was not effective as an inhibitor, whereas the hydrolyzed products of #284 remained effective inhibitors, with an MIC of 0.75 µM. These studies imply that the thiotropolone and/or one of its derivatives are effective inhibitors of *C. neoformans* growth. Furthermore, the almost 100-fold increase in activity between #284 and tropolone (#53) suggests an enormous benefit to the sulfur atom, possibly due to increased affinity of heavy metals such as iron or zinc which may prefer coordination to the sulfur of thiotropolone over the oxygen of the tropolone. Further efforts are underway to develop chemistry that would permit greater SAR of thiotropolones against *C. neoformans*.

The remaining library tested centered around substituted tropolones. The tropolone with no other substitutions (#53) was a moderate inhibitor and was also relatively non-cytotoxic. Substitutions to the tropone ring led to a variety of effects on these activities. For example, the electron withdrawing substitution of Br (#54) at position C3 decreased the MIC without increasing cytotoxicity, and an isopropyl group at position C5 (#48, β-thujaplicin) also decreased the MIC with a moderate increase in cytotoxicity. A similar isopropyl substitution at C4 (#47) did not decrease the MIC value relative to #53, suggesting the importance of the positioning of the appendage. However, a larger and more complex appendage at C4 containing both an amide and a dichlorophenyl (#55) was similarly potent as β-thujaplicinol but also substantially more cytotoxic. Another fairly common tropolone natural product, purpurogallin (#195), that has a fused polyphenol appendage, was largely ineffective against *C. neoformans*.

In prior studies of tropolones and αHTs against various fungi, the activity between the two classes were either equivalent or the tropolones were superior growth inhibitors (39). Against *C. neoformans*, tropolone and αHTs are roughly equivalent in their inhibitory activity, as is evidenced by the comparable activity of #53 and 172, as well as the comparable activity between γ-thujaplicin (#46) and β-thujaplicinol (#48). γ-Thujaplicin (#46) and β-thujaplicinol (#48) share identical potency enhancement when a single isopropyl group is added, thus both scaffolds are viable starting points for future optimization. As such, 30 αHTs with diverse substitution were tested against *C. neoformans*. αHTs with substitutions only at position C4 were for the most part better or at least equivalent in their ability to inhibit *C. neoformans* growth. A smaller aliphatic or aromatic substitution (#46, 210, 262 and 265) showed equivalent or moderately improved activity to #172. An electron withdrawing (#261) or large hydrophobic group (#264), on the other hand, decreased inhibition. All five αHTs with a substitution only at C3 (#56, 106-108, 280) had decreased inhibition compared to #172. The remaining αHTs all had substitutions at position C4 plus a methyl group at C5. Seven had a benzene ring at C4 (#112-114, 144-146). While the presence of a Br or trifluoromethyl group at the para position on the benzene improved inhibition but also increased cytotoxicity, other electron withdrawing groups (Cl or nitro) decreased inhibition. Substitution with a naphthalene group (#146 and 147) improved inhibition but also increased cytotoxicity. The remaining 14 αHTs had a carbonyl at C3, (#109-111, 118, 120, 143, 274, 308-313, 315, 318). Smaller esters (#109, 274) and the carboxylate (#319) showed very little inhibition (MIC≥50 µM), as was the case with smaller methyl- (#110) and isopropyl-ketones (#143). However, the activity was restored (MIC≤36 M) among the remaining 10 ketones, and in some instances (#120, 308, 310) approached that of β-thujaplicinol (MIC=11-12 M). Three additional α-methoxytropolones (#273, 317, and 318) were also tested and showed no activity. Without wishing to be bound by any theory, it is believed that the lack of activity of #318, which is a close analog of one of the more active αHTs, #308, suggests that the C7 hydroxylate may be involved in metalloenzyme binding for the αHTs.

This screen was conducted with the aim of determining if tropones or tropolones could be a potential scaffold for developing new inhibitors of *C. neoformans*. The α-hydroxytropolones are likely to inhibit at least in part through their ability to coordinate divalent cations in metalloenzyme active sites. These compounds are effective inhibitors of HIV, HBV and Herpes Simplex viruses, most likely via coordination of the $Mg^{++}$ ions in the active sites of enzymes that are members of the nucleotidyl transferase superfamily (Lu et al., 2015, Ireland et al., 2016 and Meck et al., 2014). There are at least 40 proteins encoded in the *C. neoformans* genome that likely belong to this class of enzymes (Janbon et al., 2014), and of the various αHTs tested, nine (#46, 114, 120, 145, 147, 265, 308, 310, 311) have MICs≤15 M. Given the large number of potential enzyme targets, it is possible that these compounds inhibit more than one enzyme in *C. neoformans*.

Figures 9A, 9B, 9C, 9D, 9E:
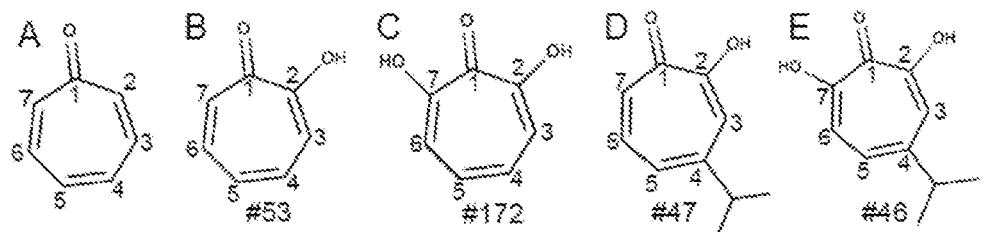
FIGS. 9A-9E. Structures of (FIG. 9A) tropone, (FIG. 9B) tropolone, (FIG. 9C) α-hydroxytropolone (FIG. 9D) β-thujaplicin and (FIG. 9E) β-thujaplicinol with the R-group numbering and the natural products.

Tropolone itself (FIG. 9B) is bacteriostatic and bactericidal against a wide range of bacterial species, and is known to inhibit metalloproteases, with particularly high activity against carboxypeptidase A, a $Zn^{++}$-dependent matrix metalloprotease (Jacobsen et al., 2007). Tropolone and j-thujaplicin (FIG. 9A) also inhibit the $Zn^{++}$-dependent glyoxalase I of *Plasmodium falciparum*: at low µM concentrations (Ishiyama et al., 2014). There are over 30 potential $Zn^{++}$-binding proteins, including members of the carboxypeptidase and glyoxalase protein families, in the *C. neoformans* genome. Thus, the tropone and tropolones appear to be a promising scaffold to explore for anti-cryptococcal inhibitors as 4 of the 19 tested have MICs<10 µM, including #284 which has an MIC<1 µM with a TI of >300.

The hit (#284) inhibits >80% of cryptococcal growth at 0.2 µM and is relatively nontoxic in liver cells ($CC_{50}$=71 µM), giving it a therapeutic index of >300 under these conditions. It is fungicidal and does not interact antagonistically with either approved antifungal, FLC or AMB. Compound #284 is a tropone with a thioester linkage. The high-energy nature of thioester bonds makes it likely that this compound is hydrolyzed in the cells or culture media resulting in a tropothione and p-benzoic acid. The fact that the hydrolyzed products are still potent inhibitors of cryptococcal growth (FIG. 6) and p-benzoic acid is not suggests strongly that the tropothione or its oxidized derivatives are functionally active derivatives of this compound.

2. Additional Biological Testing

Activity data for compounds #363-#365 is shown below in Table 3. This data was obtained using similar methods to the data described above. Given the loss of activity for the compounds with the benzylthio derivative relative to the thioacyl or the free thiol compound suggests that a hydrolysable thioester bond or a free thiol is important for activity.

TABLE 3

Activity of Compounds #363-#365

| Compound | Compound ID | MIC (µM) | $CC_{50}$ (µM) | TI |
|---|---|---|---|---|
| tropone with SH substituent | 363 | 0.2 | 21 | 105 |
| tropone with thiobenzoate (S-C(=O)-phenyl) | 364 | 0.2 | 46 | 230 |
| tropone with S-CH2-(4-methylphenyl) | 365 | >50 | >100 | ~2 |

Additional compounds have also been tested and are shown in FIG. 5C.

Eight compounds in the 1-Hydroxy-1,8-naphthyridin-2 (1H)-one (HNO) chemical family were also tested. Three compounds, #149, #153 and #154, inhibited growth of *C. neoformans* >80% with MICs of ~10 µM, ~4 µM and ~20 µM respectively.

These compounds were also cytotoxic at low M levels as measured by the MTT assay in human hepatoma cells which detects mitochondrial function, leading to TI values of ~2 for all compounds. However, the cells had not died by the end of the treatment window. Based upon these data and without wishing to be bound by any theory, it is believed that the compounds may be cytostatic rather than cytotoxic, which would make minimization of the negative effects on the cells.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references to the extent that they provide exemplary procedural or other details supplementary to those set forth herein, are specifically incorporated herein by reference.

U.S. Pat. No. 4,066,784
Amon et al., *Journal of Organic Chemistry*, 52:4851-4855, 1987.
Banerjee, et al., *PLoS One*, 9:e87246, 2014.
Banwell et al., *Australian Journal of Chemistry*, 44:705-728, 1991.
Berenbaum, *J Infect Dis*, 137:122-130, 1978.
D'Erasmo et al., *Bioorg Med Chem Lett*, 24:4035-4038, 2014.
D'Erasmo et al., *MedChemComm*, 7:1789-1792, 2016.
Doering, *Annu Rev Microbiol*, 63:223-247, 2009.
Ghannoum et al., *J Clin Microbiol*, 30:2881-2886, 1992.
Guo et al., *J Virol*, 81:12472-12484, 2007.
Hirsch et al., *Bioorg Med Chem Lett*, 24:4943-4947, 2014.
Ireland et al., *Antimicrob Agents Chemother*, doi:10.1128/aac.02675-15, 2016.
Ishiyama et al., *J Antibiot* (Tokyo), 67:545-547, 2014.
Jacobsen et al., *Biochim Biophys Acta*, 1803:72-94, 2010.
Jacobsen et al., *Inorganica Chimica Acta*, 360:264-272, 2007.
Janbon et al., *PLoS Genet*, 10:e1004261, 2014.
Klepser et al., *J Antimicrob Chemother*, 41:397-401, 1998.
Lu et al., *Antimicrob Agents Chemother*, 59:1070-1079, 2015.
Machiguchi, et al., *Bull. Chem. Soc. Japan*, 66(12):3699-3706, 1993.
Meck et al., *MedChemComm*, 5:842-852, 2014.
Meck et al., *Org Lett*, 14:5988-5991, 2012.
Mesa-Arango, et al., *Antimicrob Agents Chemother*, 58:6627-6638, 2014.
Nakano et al., *Sci Rep*, 5:15337, 2015.
Nozoe, et al., *Proc. Jap. Acad.*, 8:407-409, 1952a.
Nozoe, et al., *Proc. Jap. Acad.*, 28:410-412, 1952b.
Nozoe, et al., 9:483-487, 1952c.
Nozoe, et al., *Proc. Jap. Acad.*, 29:22-26, 1953.

Odds, *J Antimicrob Chemother,* 52:1, 2003.

Takeshita, et al., *Bull. Chem. Soc. Jpn.,* 57:2321-2322, 1984.

Tavis et al., *PLoS Pathog,* 9:e1003125, 2013.

White, et al., *Antimicrob Agents Chemother,* 40:1914-1918, 1996.

Williams et al., *J Org Chem,* 78:11707-11713, 2013.

What is claimed:

1. A method of treating a fungal infection in a patient comprising administering to the patient a therapeutically effective amount of a compound of the formula:

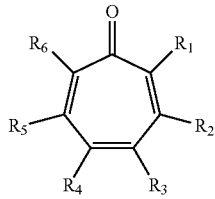

(I)

wherein:

$R_1$ and $R_6$ are each independently hydrogen, halo, or a group of the formula: —X—$Y_1$, wherein:

X is C(O), O, S, or $NR_1'$, wherein:

$R_1'$ is hydrogen, alkyl$_{(C\leq 8)}$, substituted alkyl$_{(C\leq 8)}$, aryl$_{(C\leq 8)}$, or substituted aryl$_{(C\leq 8)}$; and $Y_1$ is hydrogen, hydroxy, or alkyl$_{(C\leq 12)}$, aryl$_{(C\leq 12)}$, acyl$_{(C\leq 12)}$, alkoxy$_{(C\leq 12)}$, alkylsulfonyl$_{(C\leq 12)}$, arylsulfonyl$_{(C\leq 12)}$, or a substituted version of any of these groups;

$R_2$ and $R_5$ are each independently hydrogen, hydroxy, halo, alkyl$_{(C\leq 12)}$, substituted alkyl$_{(C\leq 12)}$, cycloalkyl$_{(C\leq 12)}$, substituted cycloalkyl$_{(C\leq 12)}$, alkenyl$_{(C\leq 12)}$, substituted alkenyl$_{(C\leq 12)}$, aryl$_{(C\leq 12)}$, substituted aryl$_{(C\leq 12)}$, aralkyl$_{(C\leq 12)}$, substituted aralkyl$_{(C\leq 12)}$, heteroaryl$_{(C\leq 12)}$, substituted heteroaryl$_{(C\leq 12)}$, alkoxy$_{(C\leq 12)}$, substituted alkoxy$_{(C\leq 12)}$, acyl$_{(C\leq 12)}$, substituted acyl$_{(C\leq 12)}$, or a group of the formula: —C(O)$Y_2R_2'$, wherein:

$Y_2$ is alkenediyl$_{(C\leq 8)}$ or substituted alkenediyl$_{(C\leq 8)}$; and $R_2'$ is aryl$_{(C\leq 12)}$, heteroaryl$_{(C\leq 12)}$, arenediyl$_{(C\leq 12)}$-O-aryl$_{(C\leq 12)}$, or a substituted version of any of these groups; and $R_3$ and $R_4$ are each independently hydrogen, hydroxy, halo, nitroso, alkyl$_{(C\leq 12)}$, substituted alkyl$_{(C\leq 12)}$, cycloalkyl$_{(C\leq 12)}$, substituted cycloalkyl$_{(C\leq 12)}$, alkenyl$_{(C\leq 12)}$, substituted alkenyl$_{(C\leq 12)}$, aryl$_{(C\leq 18)}$, substituted aryl$_{(C\leq 18)}$, heteroaryl$_{(C\leq 18)}$, substituted heteroaryl$_{(C\leq 18)}$, acyl$_{(C\leq 18)}$, substituted acyl$_{(C\leq 18)}$, amido$_{(C\leq 18)}$, substituted amido$_{(C\leq 18)}$, or C(O)$R_a$ or S(O)$_2R_a$ wherein:

$R_a$ is alkyl$_{(C\leq 18)}$, cycloalkyl$_{(C\leq 18)}$, aryl$_{(C\leq 18)}$, heteroaryl$_{(C\leq 18)}$, alkoxy$_{(C\leq 18)}$, aryloxy$_{(C\leq 18)}$, -alkanediyl$_{(C\leq 6)}$-cycloalkyl$_{(C\leq 12)}$; or a substituted version of any of these groups; or $R_2$ and $R_3$ are taken together and are a compound of the formula:

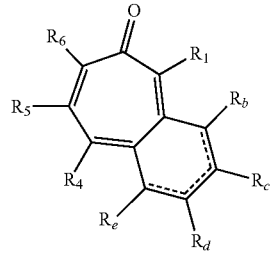

(IA)

wherein:

$R_b$, $R_c$, $R_d$, and $R_e$ are each independently hydrogen, hydroxy, or alkyl$_{(C\leq 8)}$, cycloalkyl$_{(C\leq 8)}$, alkenyl$_{(C\leq 8)}$, or a substituted version of any of these groups; or -alkanediyl$_{(C\leq 6)}$-alkylamino$_{(C\leq 8)}$, -alkane-diyl$_{(C\leq 6)}$-dialkylamino$_{(C\leq 8)}$, or a substituted version of either of these groups; or $R_1$ and $R_2$ are taken together and are a compound of the formula:

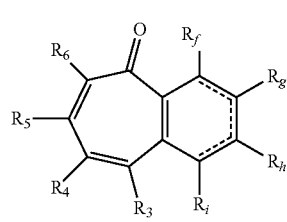

(IB)

wherein:

$R_f$, $R_g$, $R_h$, and $R_i$ are each independently hydrogen, hydroxy, or alkyl$_{(C\leq 8)}$, cycloalkyl$_{(C\leq 8)}$, alkenyl$_{(C\leq 8)}$, or a substituted version of any of these groups; or -alkanediyl$_{(C\leq 6)}$-alkylamino$_{(C\leq 8)}$, -alkane-diyl$_{(C\leq 6)}$-dialkylamino$_{(C\leq 8)}$, or a substituted version of either of these groups; or $R_3$ and $R_4$ are taken together and are a compound of the formula:

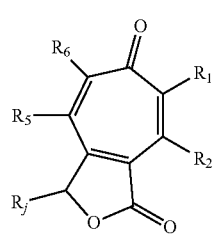

(IC)

wherein:

$R_j$ is hydrogen, hydroxy, halo, or alkyl$_{(C\leq 8)}$, cycloalkyl$_{(C\leq 8)}$, alkenyl$_{(C\leq 8)}$, or a substituted version of any of these groups; or -alkanediyl$_{(C\leq 6)}$-alkylamino$_{(C\leq 8)}$, -alkane-diyl$_{(C\leq 6)}$-dialkylamino$_{(C\leq 8)}$, or a substituted version of either of these groups; or a compound of the formula:

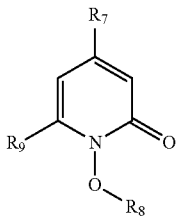

(II)

wherein:
R$_7$ is alkyl$_{(C\leq12)}$, aryl$_{(C\leq12)}$, aralkyl$_{(C\leq12)}$, heteroaryl$_{(C\leq12)}$, or a substituted version of any of these groups;
R$_8$ is hydrogen, alkyl$_{(C\leq8)}$, or substituted alkyl$_{(C\leq8)}$; and
R$_9$ is hydrogen, alkyl$_{(C\leq12)}$, or substituted alkyl$_{(C\leq12)}$;
a compound of the formula:

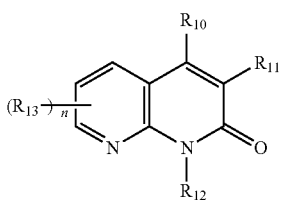

(III)

wherein:
R$_{10}$ is amino, hydroxy, or aryl$_{(C\leq18)}$, aralkyl$_{(C\leq18)}$, aryloxy$_{(C\leq18)}$, cycloalkylamino$_{(C\leq18)}$, aralkoxy$_{(C\leq18)}$, arylamino$_{(C\leq18)}$, aralkamino$_{(C\leq18)}$, diarylamino$_{(C\leq18)}$, diaralkamino$_{(C\leq18)}$, or a substituted version of any of these groups;
R$_{11}$ is hydrogen, acyl$_{(C\leq12)}$, or substituted acyl$_{(C\leq12)}$, or —C(O)R$_a$; wherein:
R$_a$ is amino, hydroxy, alkoxy$_{(C\leq8)}$, substituted alkoxy$_{(C\leq8)}$, alkylamino$_{(C\leq8)}$, substituted alkylamino$_{(C\leq8)}$, dialkylamino$_{(C\leq8)}$, or substituted dialkylamino$_{(C\leq8)}$;
R$_{12}$ is hydrogen, alkoxy$_{(C\leq8)}$, or substituted alkoxy$_{(C\leq8)}$;
R$_{13}$ is amino, cyano, halo, hydroxy, nitro, alkyl$_{(C\leq8)}$, substituted alkyl$_{(C\leq8)}$, acyl$_{(C\leq8)}$, substituted acyl$_{(C\leq8)}$, alkoxy$_{(C\leq8)}$, substituted alkoxy$_{(C\leq8)}$, acyloxy$_{(C\leq8)}$, substituted acyloxy$_{(C\leq8)}$, alkylamino$_{(C\leq8)}$, substituted alkylamino$_{(C\leq8)}$, dialkylamino$_{(C\leq8)}$, substituted dialkylamino$_{(C\leq8)}$, amido$_{(C\leq8)}$, or substituted amido$_{(C\leq8)}$; and
n is 1, 2, or 3;
or a pharmaceutically acceptable salt or tautomer thereof;
wherein the compound is formulated as a pharmaceutical composition comprising the compound and an excipient, further wherein the pharmaceutical composition is formulated for oral administration, intraarterial administration, intravenous administration, parenteral administration, or for administration to the lungs;
provided that the compound is not thujaplicin when the fungal infection is a *Candida albicans* infection.

2. The method of claim 1, wherein the compound is further defined as:

a compound of the formula:

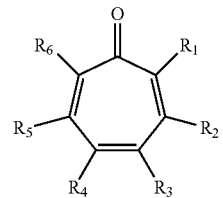

(I)

wherein:
R$_1$ and R$_6$ are each independently hydrogen, halo, or a group of the formula: —X—Y$_1$, wherein:
X is O, S, or NR$_1$', wherein:
R$_1$' is hydrogen, alkyl$_{(C\leq8)}$, substituted alkyl$_{(C\leq8)}$, aryl$_{(C\leq8)}$, or substituted aryl$_{(C\leq8)}$; and
Y$_1$ is hydrogen, or alkyl$_{(C\leq12)}$, aryl$_{(C\leq12)}$, acyl$_{(C\leq12)}$, alkylsulfonyl$_{(C\leq12)}$, arylsulfonyl$_{(C\leq12)}$, or a substituted version of any of these groups;
R$_2$ and R$_5$ are each independently hydrogen, hydroxy, halo, alkyl$_{(C\leq12)}$, substituted alkyl$_{(C\leq12)}$, cycloalkyl$_{(C\leq12)}$, substituted cycloalkyl$_{(C\leq12)}$, aryl$_{(C\leq12)}$, substituted aryl$_{(C\leq12)}$, aralkyl$_{(C\leq12)}$, substituted aralkyl$_{(C\leq12)}$, heteroaryl$_{(C\leq12)}$, substituted heteroaryl$_{(C\leq12)}$, alkoxy$_{(C\leq12)}$, substituted alkoxy$_{(C\leq12)}$, acyl$_{(C\leq12)}$, substituted acyl$_{(C\leq12)}$; and
R$_3$ and R$_4$ are each independently hydrogen, hydroxy, halo, nitroso, alkyl$_{(C\leq12)}$, substituted alkyl$_{(C\leq12)}$, cycloalkyl$_{(C\leq12)}$, substituted cycloalkyl$_{(C\leq12)}$, alkenyl$_{(C\leq12)}$, substituted alkenyl$_{(C\leq12)}$, aryl$_{(C\leq18)}$, substituted aryl$_{(C\leq18)}$, heteroaryl$_{(C\leq18)}$, substituted heteroaryl$_{(C\leq18)}$, acyl$_{(C\leq18)}$, substituted acyl$_{(C\leq18)}$, amido$_{(C\leq18)}$, substituted amido$_{(C\leq18)}$, or —C(O)R$_a$, wherein:
R$_a$ is alkyl$_{(C\leq18)}$, cycloalkyl$_{(C\leq18)}$, aryl$_{(C\leq18)}$, heteroaryl$_{(C\leq18)}$, alkoxy$_{(C\leq18)}$, aryloxy$_{(C\leq18)}$, -alkanediyl$_{(C\leq6)}$-cycloalkyl$_{(C\leq12)}$; or a substituted version of any of these groups; or
R$_2$ and R$_3$ are taken together and are a compound of the formula:

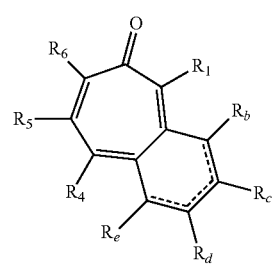

(IA)

wherein:
R$_b$, R$_c$, R$_d$, and R$_e$ are each independently hydrogen, hydroxy, or alkyl$_{(C\leq8)}$, cycloalkyl$_{(C\leq8)}$, alkenyl$_{(C\leq8)}$, or a substituted version of any of these groups; or -alkanediyl$_{(C\leq6)}$-alkylamino$_{(C\leq8)}$, -alkane-diyl$_{(C\leq6)}$-dialkylamino$_{(C\leq8)}$, or a substituted version of either of these groups; or
R$_1$ and R$_2$ are taken together and are a compound of the formula:

wherein:

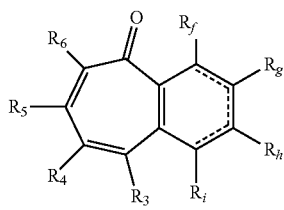
(IB)

R_f, R_g, R_h, and R_i are each independently hydrogen, hydroxy, or alkyl$_{(C\leq8)}$, cycloalkyl$_{(C\leq8)}$, alkenyl$_{(C\leq8)}$, or a substituted version of any of these groups; or -alkanediyl$_{(C\leq6)}$-alkylamino$_{(C\leq8)}$, -alkane-diyl$_{(C\leq6)}$-dialkylamino$_{(C\leq8)}$, or a substituted version of either of these groups; or R_3 and R_4 are taken together and are a compound of the formula:

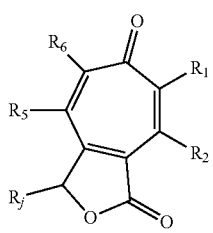
(IC)

wherein:

R_3 is hydrogen, hydroxy, halo, or alkyl$_{(C\leq8)}$, cycloalkyl$_{(C\leq8)}$, alkenyl$_{(C\leq8)}$, or a substituted version of any of these groups; or -alkanediyl$_{(C\leq6)}$-alkylamino$_{(C\leq8)}$, -alkanediyl$_{(C\leq6)}$-dialkylamino$_{(C\leq8)}$, or a substituted version of either of these groups; or a compound of the formula:

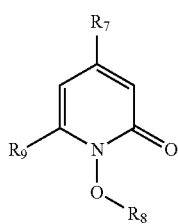
(II)

wherein:

R_7 is alkyl$_{(C\leq12)}$, aryl$_{(C\leq12)}$, aralkyl$_{(C\leq12)}$, heteroaryl$_{(C\leq12)}$, or a substituted version of any of these groups;

R_8 is hydrogen, alkyl$_{(C\leq8)}$, or substituted alkyl$_{(C\leq8)}$; and

R_9 is hydrogen, alkyl$_{(C\leq12)}$, or substituted alkyl$_{(C\leq12)}$;

a compound of the formula:

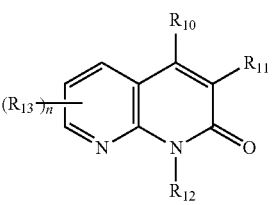
(III)

wherein:

R_10 is amino, hydroxy, or aryl$_{(C\leq18)}$, aralkyl$_{(C\leq18)}$, aryloxy$_{(C\leq18)}$, cycloalkylamino$_{(C\leq18)}$, aralkoxy$_{(C\leq18)}$, arylamino$_{(C\leq18)}$, aralkamino$_{(C\leq18)}$, diarylamino$_{(C\leq18)}$, diaralkamino$_{(C\leq18)}$, or a substituted version of any of these groups;

R_11 is hydrogen, acyl$_{(C\leq12)}$, or substituted acyl$_{(C\leq12)}$, or —C(O)R_a; wherein:
R_a is amino, hydroxy, alkoxy$_{(C\leq8)}$, substituted alkoxy$_{(C\leq8)}$, alkylamino$_{(C\leq8)}$, substituted alkylamino$_{(C\leq8)}$, dialkylamino$_{(C\leq8)}$, or substituted dialkylamino$_{(C\leq8)}$;

R_12 is hydrogen, alkoxy$_{(C\leq8)}$, or substituted alkoxy$_{(C\leq8)}$;

R_13 is amino, cyano, halo, hydroxy, nitro, alkyl$_{(C\leq8)}$, substituted alkyl$_{(C\leq8)}$, acyl$_{(C\leq8)}$, substituted acyl$_{(C\leq8)}$, alkoxy$_{(C\leq8)}$, substituted alkoxy$_{(C\leq8)}$, acyloxy$_{(C\leq8)}$, substituted acyloxy$_{(C\leq8)}$, alkylamino$_{(C\leq8)}$, substituted alkylamino$_{(C\leq8)}$, dialkylamino$_{(C\leq8)}$, substituted dialkylamino$_{(C\leq8)}$, amido$_{(C\leq8)}$, or substituted amido$_{(C\leq8)}$; and n is 1, 2, or 3;

or a pharmaceutically acceptable salt thereof.

3. The method of claim 1, wherein the fungal infection is an infection of a *Cryptococcus* fungus.

4. The method of claim 3, wherein the fungal infection is an infection of *Cryptococcus neoformans*.

5. The method of claim 1, wherein the compound is further defined as:

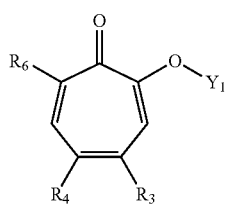
(IV)

wherein:

Y_1 is hydrogen, alkyl$_{(C\leq8)}$, substituted alkyl$_{(C\leq8)}$, acyl$_{(C\leq8)}$, or substituted acyl$_{(C\leq8)}$;

R_6 is hydrogen, hydroxy, alkoxy$_{(C\leq8)}$, substituted alkoxy$_{(C\leq8)}$, acyloxy$_{(C\leq8)}$, or substituted acyloxy$_{(C\leq8)}$; and R_3 and R_4 are each independently selected from hydrogen, hydroxy, nitroso, or alkyl$_{(C\leq12)}$, substituted alkyl$_{(C\leq12)}$, cycloalkyl$_{(C\leq12)}$, substituted cycloalkyl$_{(C\leq12)}$, alkenyl$_{(C\leq12)}$, substituted alkenyl$_{(C\leq12)}$, aryl$_{(C\leq18)}$, substituted aryl$_{(C\leq18)}$, heteroaryl$_{(C\leq8)}$, substituted heteroaryl$_{(C\leq8)}$, acyl$_{(C\leq12)}$, substituted acyl$_{(C\leq12)}$, or —C(O)R_a, wherein:
R_a is alkyl$_{(C\leq18)}$, cycloalkyl$_{(C\leq18)}$, aryl$_{(C\leq18)}$, heteroaryl$_{(C\leq18)}$, alkoxy$_{(C\leq18)}$, aryloxy$_{(C\leq18)}$, -alkanediyl$_{(C≤6)}$-cycloalkyl$_{(C≤12)}$; or a substituted version of any of these groups;

or a pharmaceutically acceptable salt or tautomer thereof.

6. The method of claim 5, wherein the compound is further defined as:

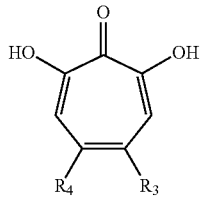

(V)

wherein:

R$_3$ and R$_4$ are each independently hydrogen, hydroxy, alkyl$_{(C≤12)}$, substituted alkyl$_{(C≤12)}$, cycloalkyl$_{(C≤12)}$, substituted cycloalkyl$_{(C≤12)}$, alkenyl$_{(C≤12)}$, substituted alkenyl$_{(C≤12)}$, aryl$_{(C≤18)}$, substituted aryl$_{(C≤18)}$, heteroaryl$_{(C≤8)}$, substituted heteroaryl$_{(C≤8)}$, acyl$_{(C≤12)}$, substituted acyl$_{(C≤12)}$, or —C(O)R$_a$, wherein:

R$_a$ is alkyl$_{(C≤18)}$, cycloalkyl$_{(C≤18)}$, aryl$_{(C≤18)}$, heteroaryl$_{(C≤18)}$, alkoxy$_{(C≤18)}$, aryloxy$_{(C≤18)}$, -alkanediyl$_{(C≤6)}$-cycloalkyl$_{(C≤12)}$; or a substituted version of any of these groups;

or a pharmaceutically acceptable salt or tautomer thereof.

7. The method of claim 1, wherein the compound is further defined as:

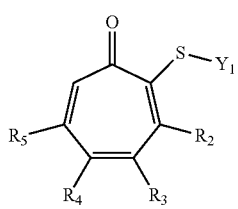

(V)

wherein:

Y$_1$ is hydrogen or alkyl$_{(C≤12)}$, aryl$_{(C≤12)}$, acyl$_{(C≤12)}$, alkylsulfonyl$_{(C≤12)}$, arylsulfonyl$_{(C≤12)}$, or a substituted version of any of these groups;

R$_2$ and R$_5$ are each independently hydrogen, hydroxy, halo, alkyl$_{(C≤12)}$, substituted alkyl$_{(C≤12)}$, cycloalkyl$_{(C≤12)}$, substituted cycloalkyl$_{(C≤12)}$, aryl$_{(C≤12)}$, substituted aryl$_{(C≤12)}$, aralkyl$_{(C≤12)}$, substituted aralkyl$_{(C≤12)}$, heteroaryl$_{(C≤12)}$, substituted heteroaryl$_{(C≤12)}$, alkoxy$_{(C≤12)}$, substituted alkoxy$_{(C≤12)}$, acyl$_{(C≤12)}$, or substituted acyl$_{(C≤12)}$; and R$_3$ and R$_4$ are each independently hydrogen, hydroxy, halo, nitroso, alkyl$_{(C≤12)}$, substituted alkyl$_{(C≤12)}$, cycloalkyl$_{(C≤12)}$, substituted cycloalkyl$_{(C≤12)}$, alkenyl$_{(C≤12)}$, substituted alkenyl$_{(C≤12)}$, aryl$_{(C≤18)}$, substituted aryl$_{(C≤18)}$, heteroaryl$_{(C≤18)}$, substituted heteroaryl$_{(C≤18)}$, acyl$_{(C≤18)}$, substituted acyl$_{(C≤18)}$, amido$_{(C≤18)}$, substituted amido$_{(C≤18)}$, or —C(O)R$_a$, wherein:

R$_a$ is alkyl$_{(C≤18)}$, cycloalkyl$_{(C≤18)}$, aryl$_{(C≤18)}$, heteroaryl$_{(C≤18)}$, alkoxy$_{(C≤18)}$, aryloxy$_{(C≤18)}$, -alkanediyl$_{(C≤6)}$-cycloalkyl$_{(C≤12)}$; or a substituted version of any of these groups;

or a pharmaceutically acceptable salt or tautomer thereof.

8. The method of claim 7, wherein the compound is further defined as:

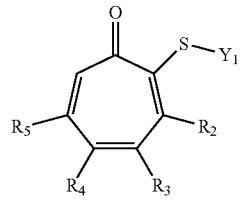

(VI)

wherein:

Y$_1$ is hydrogen or alkyl$_{(C≤12)}$, aryl$_{(C≤12)}$, acyl$_{(C≤12)}$, alkylsulfonyl$_{(C≤12)}$, arylsulfonyl$_{(C≤12)}$, or a substituted version of any of these groups;

R$_2$ and R$_5$ are each independently hydrogen, hydroxy, halo, alkyl$_{(C≤12)}$, substituted alkyl$_{(C≤12)}$, cycloalkyl$_{(C≤12)}$, substituted cycloalkyl$_{(C≤12)}$, alkoxy$_{(C≤12)}$, substituted alkoxy$_{(C≤12)}$, acyl$_{(C≤12)}$, or substituted acyl$_{(C≤12)}$; and R$_3$ and R$_4$ are each independently hydrogen, hydroxy, halo, nitroso, alkyl$_{(C≤12)}$, substituted alkyl$_{(C≤12)}$, cycloalkyl$_{(C≤12)}$, substituted cycloalkyl$_{(C≤12)}$, alkenyl$_{(C≤12)}$, substituted alkenyl$_{(C≤12)}$, aryl$_{(C≤18)}$, substituted aryl$_{(C≤18)}$, heteroaryl$_{(C≤18)}$, substituted heteroaryl$_{(C≤18)}$, acyl$_{(C≤18)}$, substituted acyl$_{(C≤18)}$, amido$_{(C≤18)}$, substituted amido$_{(C≤18)}$, or —C(O)R$_a$, wherein:

R$_a$ is alkyl$_{(C≤18)}$, cycloalkyl$_{(C≤18)}$, aryl$_{(C≤18)}$, heteroaryl$_{(C≤18)}$, alkoxy$_{(C≤18)}$, aryloxy$_{(C≤18)}$, -alkanediyl$_{(C≤6)}$-cycloalkyl$_{(C≤12)}$; or a substituted version of any of these groups;

or a pharmaceutically acceptable salt or tautomer thereof.

9. The method of claim 8, wherein the compound is further defined as:

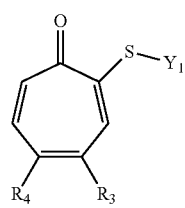

(VII)

wherein:

Y$_1$ is hydrogen or alkyl$_{(C≤12)}$, aryl$_{(C≤12)}$, acyl$_{(C≤12)}$, or a substituted version of any of these groups; and R$_3$ and R$_4$ are each independently hydrogen, hydroxy, halo, nitroso, alkyl$_{(C≤12)}$, substituted alkyl$_{(C≤12)}$, cycloalkyl$_{(C≤12)}$, substituted cycloalkyl$_{(C≤12)}$, alkenyl$_{(C≤12)}$, or substituted alkenyl$_{(C≤12)}$;

or a pharmaceutically acceptable salt or tautomer thereof.

10. The method of claim 1, wherein the compound is further defined as:

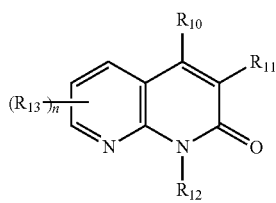

(III)

wherein:

$R_{10}$ is amino, hydroxy, aryl$_{(C \le 18)}$, aralkyl$_{(C \le 18)}$, aryloxy$_{(C \le 18)}$, aralkoxy$_{(C \le 18)}$, cycloalkylamino$_{(C \le 12)}$, arylamino$_{(C \le 18)}$, aralkamino$_{(C \le 18)}$, diarylamino$_{(C \le 18)}$, or diaralkamino$_{(C \le 18)}$;

$R_{11}$ is hydrogen, acyl$_{(C \le 12)}$, or substituted acyl$_{(C \le 12)}$, or —C(O)R$_a$; wherein:

$R_a$ is amino, hydroxy, alkoxy$_{(C \le 8)}$, substituted alkoxy$_{(C \le 8)}$, alkylamino$_{(C \le 8)}$, substituted alkylamino$_{(C \le 8)}$, dialkylamino$_{(C \le 8)}$, or substituted dialkylamino$_{(C \le 8)}$; and $R_{12}$ is hydrogen, alkoxy$_{(C \le 8)}$, or substituted alkoxy$_{(C \le 8)}$;

or a pharmaceutically acceptable salt or tautomer thereof.

11. The method of claim 1, wherein the compound is further defined as:

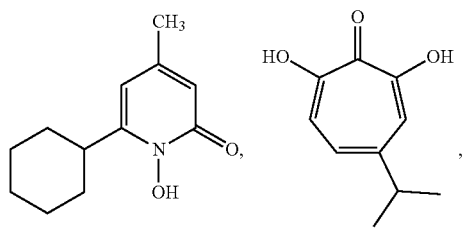

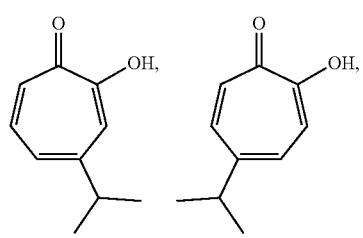

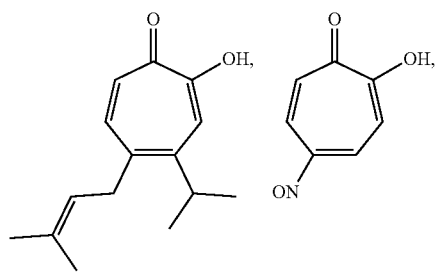

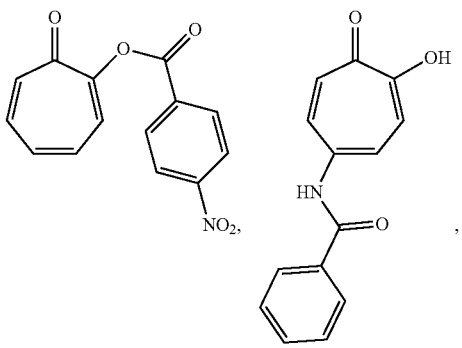

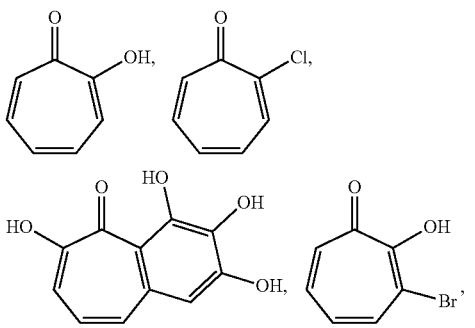

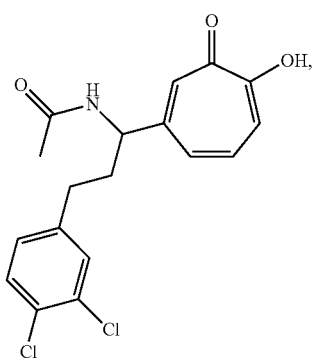

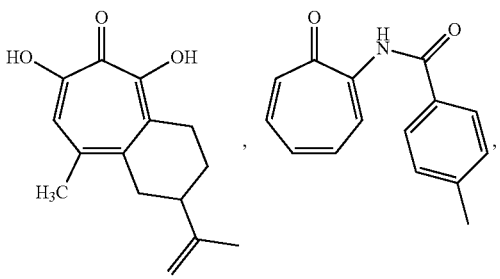

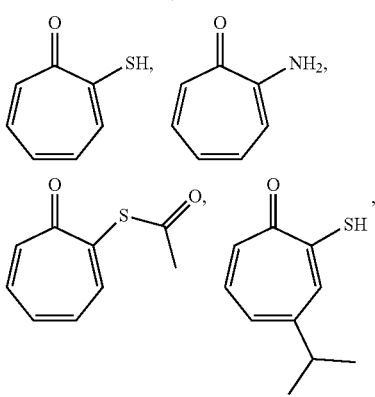

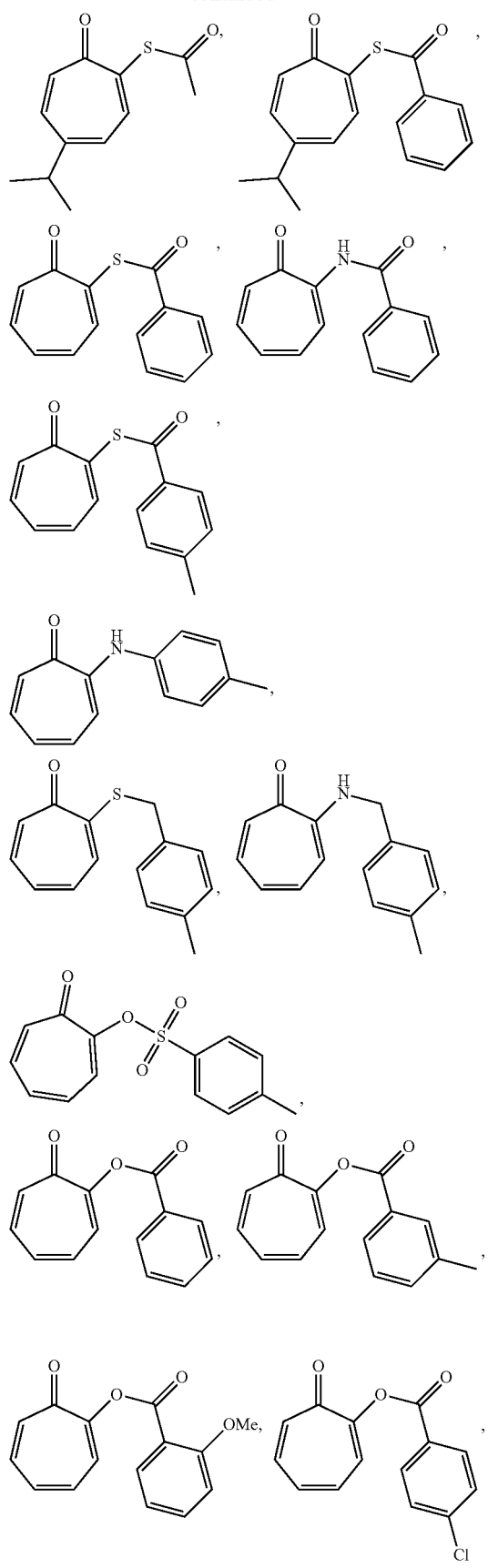
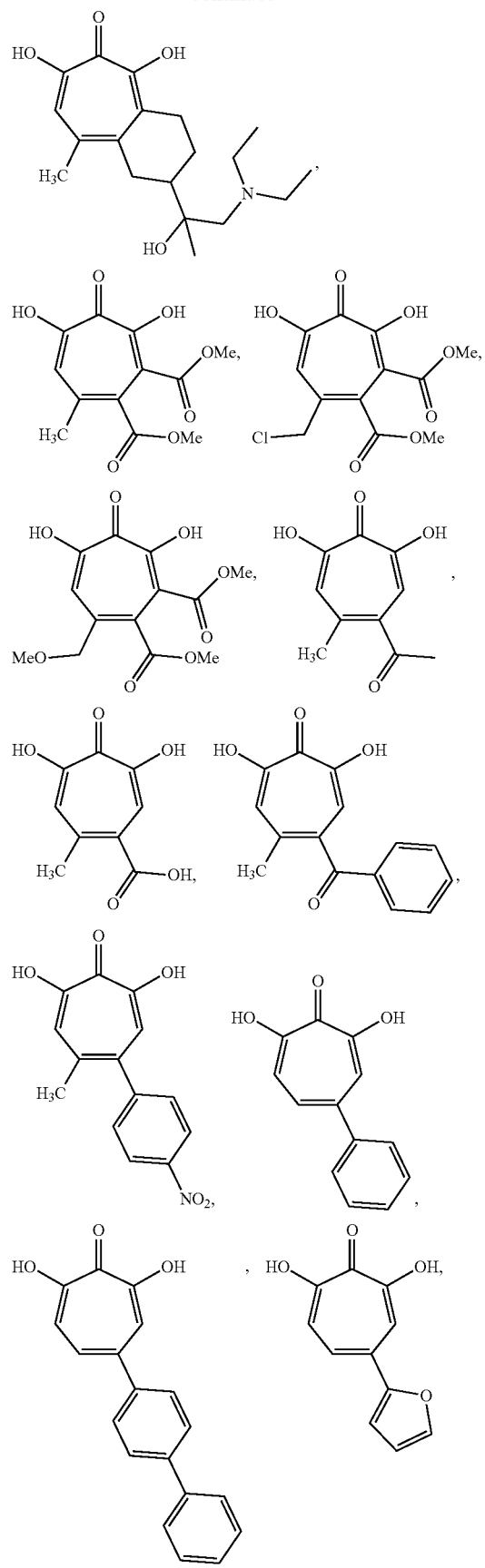

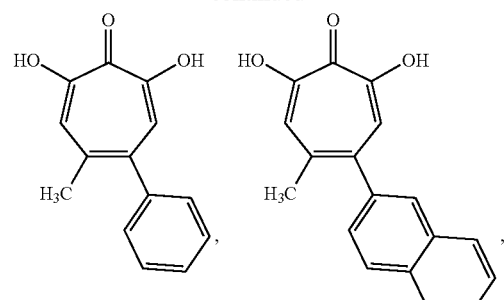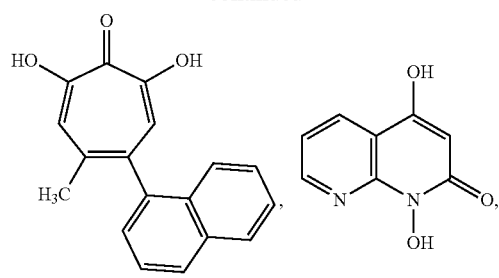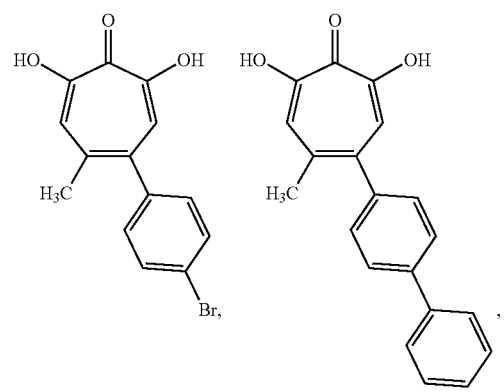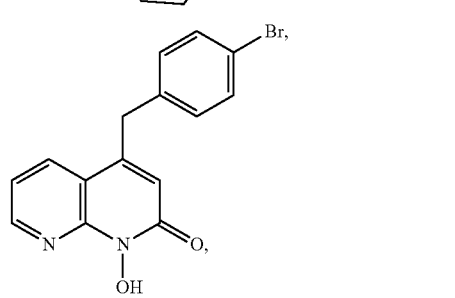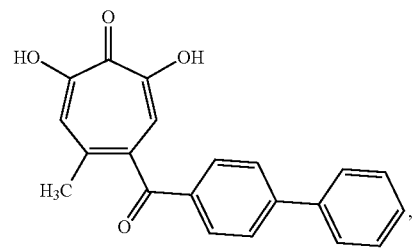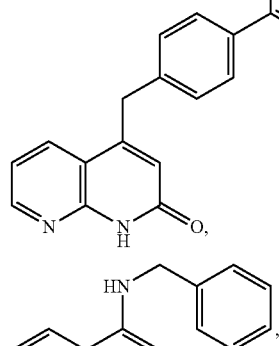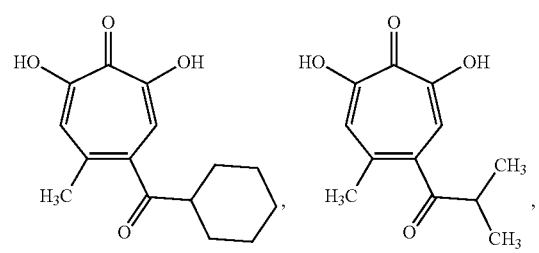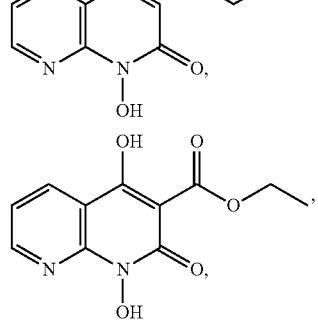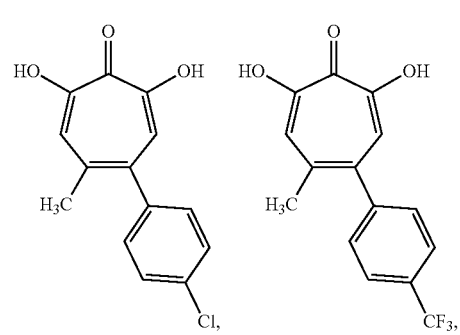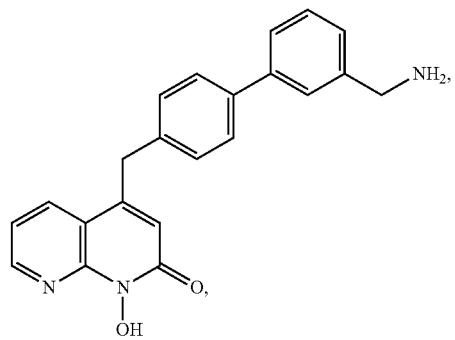

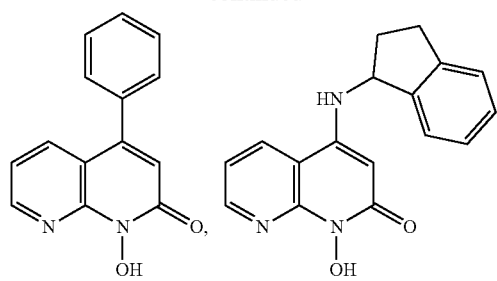
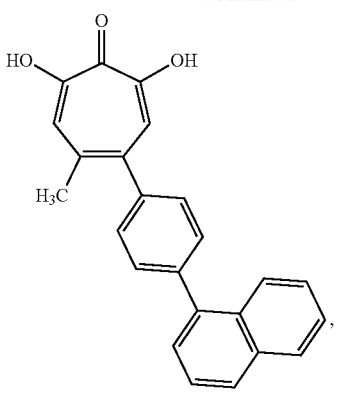
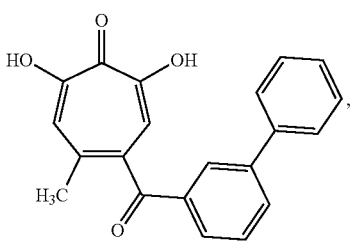
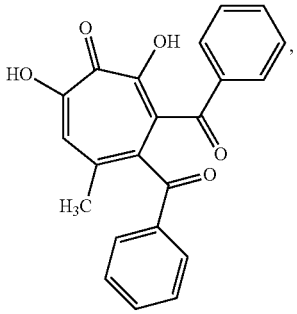
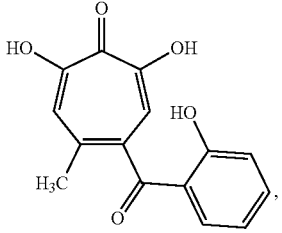
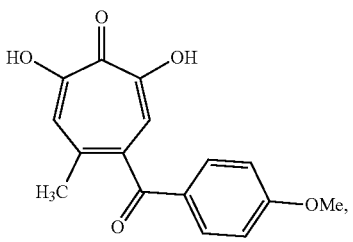
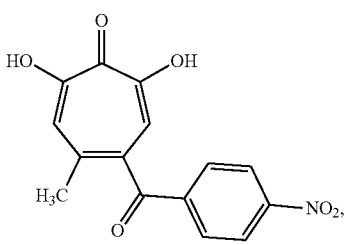

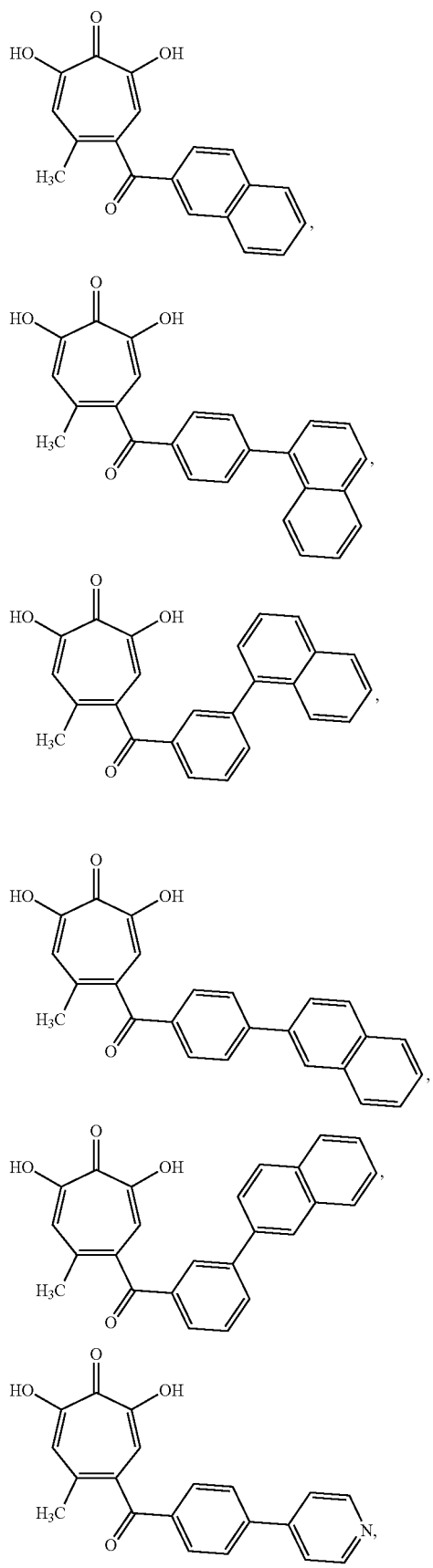
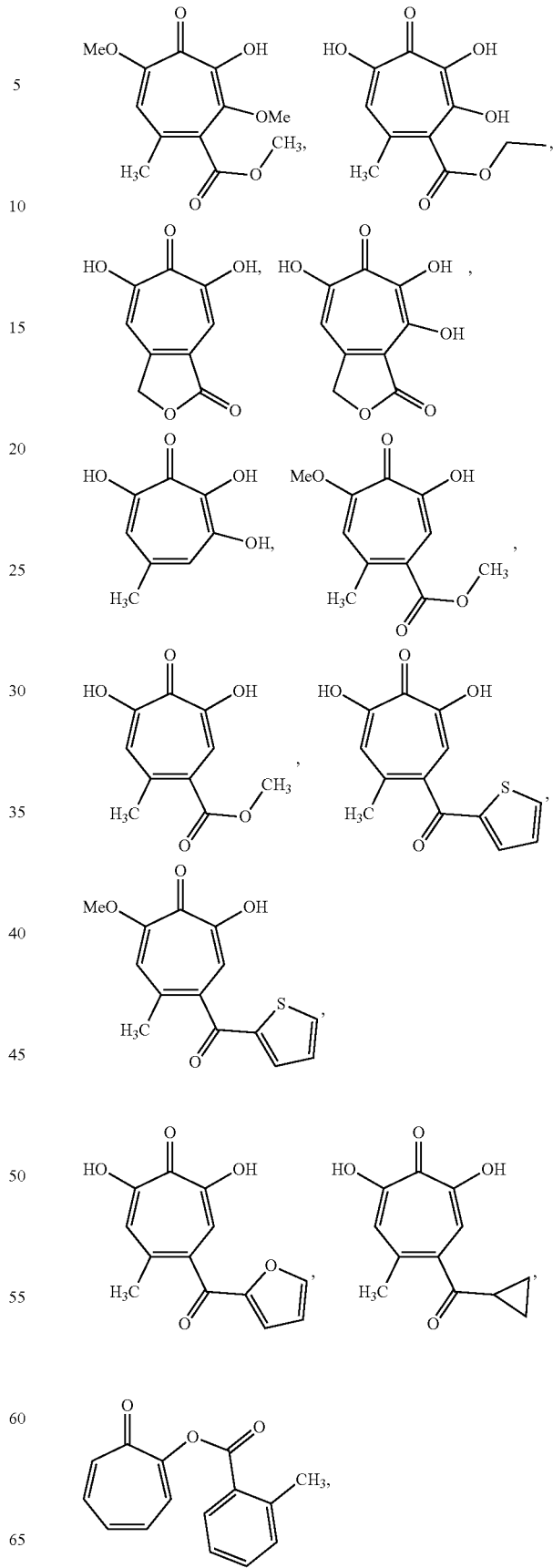

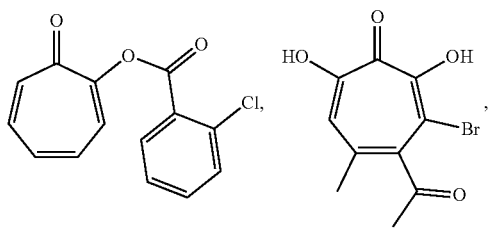
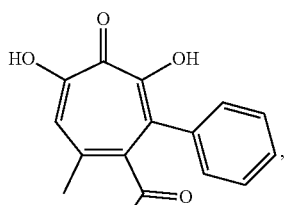
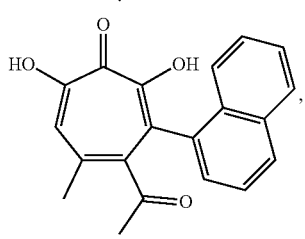
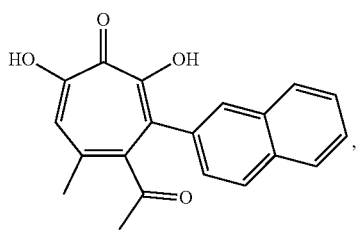
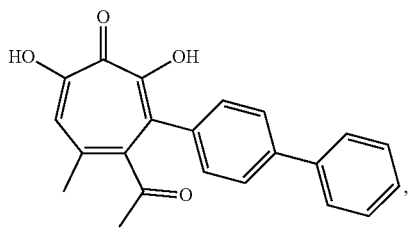
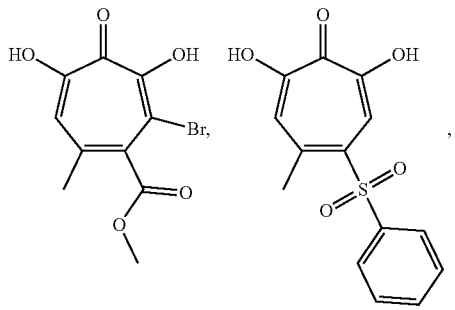
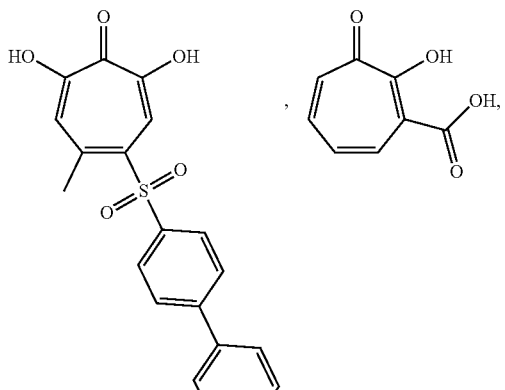
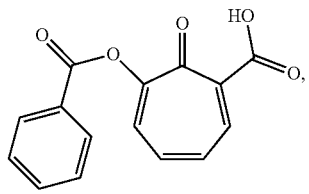
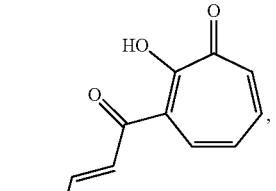
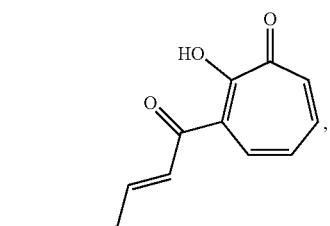
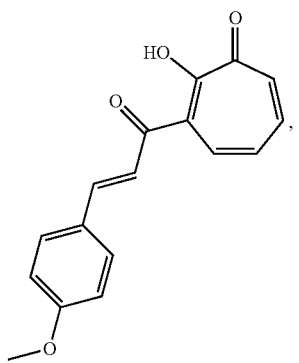

115
-continued

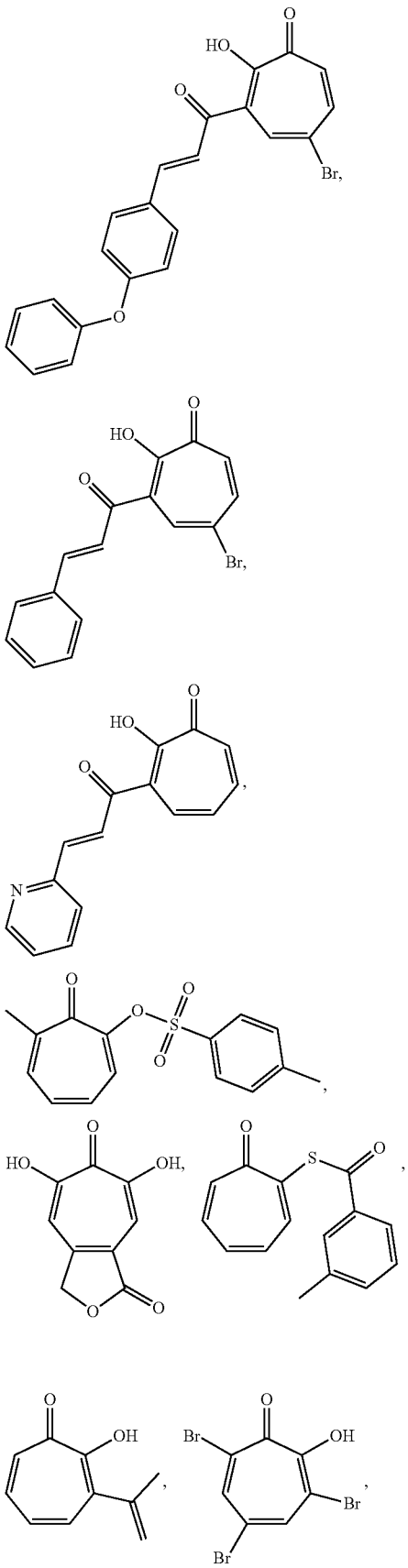

116
-continued

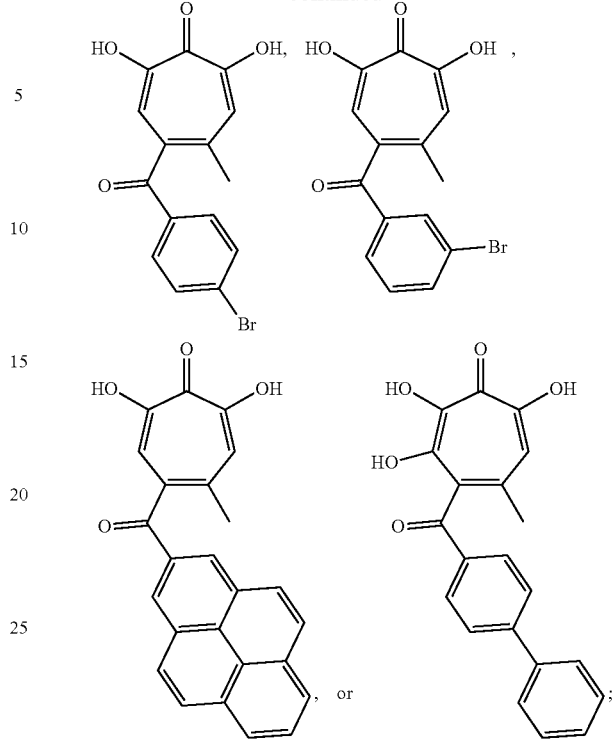

or a pharmaceutically acceptable salt or tautomer thereof.

12. The method of claim 1, wherein the patient has a weakened immune system.

13. The method of claim 1, wherein the method further comprises administering a second anti-fungal therapy.

14. The method of claim 1, wherein the fungal infection is in the central nervous system or in the lungs.

15. The method of claim 1, wherein the fungal infection results in cryptococcosis.

16. A method of treating a condition associated with a *Cryptococcus neoformans* infection in a patient in need thereof comprising administering to the patient a therapeutically effective amount of a compound of the formula:

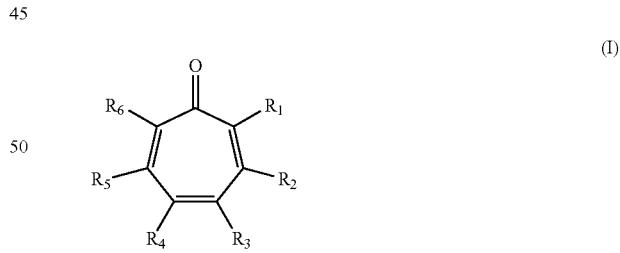

wherein:
  $R_1$ and $R_6$ are each independently hydrogen, halo, or a group of the formula: —X—$Y_1$, wherein:
    X is C(O), O, S, or $NR_1'$, wherein:
      $R_1'$ is hydrogen, alkyl$_{(C \leq 8)}$, substituted alkyl$_{(C \leq 8)}$, aryl$_{(C \leq 8)}$, or substituted aryl$_{(C \leq 8)}$; and
      $Y_1$ is hydrogen, hydroxy, or alkyl$_{(C \leq 12)}$, aryl$_{(C \leq 12)}$, acyl$_{(C \leq 12)}$, alkoxy$_{(C \leq 12)}$, alkylsulfonyl$_{(C \leq 12)}$, arylsulfonyl$_{(C \leq 12)}$, or a substituted version of any of these groups;
  $R_2$ and $R_5$ are each independently hydrogen, hydroxy, halo, alkyl$_{(C \leq 12)}$, substituted alkyl$_{(C \leq 12)}$, cycloalkyl$_{(C≤12)}$, substituted cycloalkyl$_{(C≤12)}$, alkenyl$_{(C≤12)}$, substituted alkenyl$_{(C≤12)}$, aryl$_{(C≤12)}$, substituted aryl$_{(C≤12)}$, aralkyl$_{(C≤12)}$, substituted aralkyl$_{(C≤12)}$, heteroaryl$_{(C≤12)}$, substituted heteroaryl$_{(C≤12)}$, alkoxy$_{(C≤12)}$, substituted alkoxy$_{(C≤12)}$, acyl$_{(C≤12)}$, substituted acyl$_{(C≤12)}$, or a group of the formula: —C(O)Y$_2$R$_2$', wherein:
  Y$_2$ is alkenediyl$_{(C≤8)}$ or substituted alkenediyl$_{(C≤8)}$; and
  R$_2$' is aryl$_{(C≤12)}$, heteroaryl$_{(C≤12)}$, arenediyl$_{(C≤12)}$-O-aryl$_{(C≤12)}$, or a substituted version of any of these groups; and
R$_3$ and R$_4$ are each independently hydrogen, hydroxy, halo, nitroso, alkyl$_{(C≤12)}$, substituted alkyl$_{(C≤12)}$, cycloalkyl$_{(C≤12)}$, substituted cycloalkyl$_{(C≤12)}$, alkenyl$_{(C≤12)}$, substituted alkenyl$_{(C≤12)}$, aryl$_{(C≤18)}$, substituted aryl$_{(C≤18)}$, heteroaryl$_{(C≤18)}$, substituted heteroaryl$_{(C≤18)}$, acyl$_{(C≤18)}$, substituted acyl$_{(C≤18)}$, amido$_{(C≤18)}$, substituted amido$_{(C≤18)}$, or —C(O)R$_a$ or —S(O)$_2$R$_a$ wherein:
  R$_a$ is alkyl$_{(C≤18)}$, cycloalkyl$_{(C≤18)}$, aryl$_{(C≤18)}$, heteroaryl$_{(C≤18)}$, alkoxy$_{(C≤18)}$, aryloxy$_{(C≤18)}$, -alkanediyl$_{(C≤6)}$-cycloalkyl$_{(C≤12)}$; or a substituted version of any of these groups; or
R$_2$ and R$_3$ are taken together and are a compound of the formula:

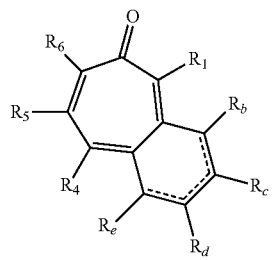

(IA)

wherein:
  R$_b$, R$_c$, R$_d$, and R$_e$ are each independently hydrogen, hydroxy, or alkyl$_{(C≤8)}$, cycloalkyl$_{(C≤8)}$, alkenyl$_{(C≤8)}$, or a substituted version of any of these groups; or -alkanediyl$_{(C≤6)}$-alkylamino$_{(C≤8)}$, -alkane-diyl$_{(C≤6)}$-dialkylamino$_{(C≤8)}$, or a substituted version of either of these groups; or
R$_1$ and R$_2$ are taken together and are a compound of the formula:

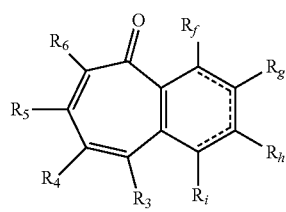

(IB)

wherein:
  R$_f$, R$_g$, R$_h$, and R$_i$ are each independently hydrogen, hydroxy, or alkyl$_{(C≤8)}$, cycloalkyl$_{(C≤8)}$, alkenyl$_{(C≤8)}$, or a substituted version of any of these groups; or -alkanediyl$_{(C≤6)}$-alkylamino$_{(C≤8)}$, -alkane-diyl$_{(C≤6)}$-dialkylamino$_{(C≤8)}$, or a substituted version of either of these groups; or
R$_3$ and R$_4$ are taken together and are a compound of the formula:

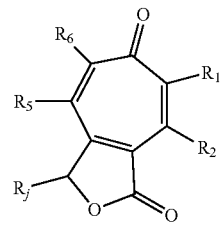

(IC)

wherein:
  R$_j$ is hydrogen, hydroxy, halo, or alkyl$_{(C≤8)}$, cycloalkyl$_{(C≤8)}$, alkenyl$_{(C≤8)}$, or a substituted version of any of these groups; or -alkanediyl$_{(C≤6)}$-alkylamino$_{(C≤8)}$, -alkane-diyl$_{(C≤6)}$-dialkylamino$_{(C≤8)}$, or a substituted version of either of these groups; or
a compound of the formula:

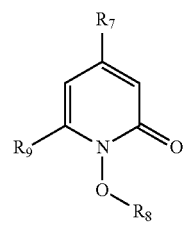

(II)

wherein:
  R$_7$ is alkyl$_{(C≤12)}$, aryl$_{(C≤12)}$, aralkyl$_{(C≤12)}$, heteroaryl$_{(C≤12)}$, or a substituted version of any of these groups;
  R$_8$ is hydrogen, alkyl$_{(C≤8)}$, or substituted alkyl$_{(C≤8)}$; and
  R$_9$ is hydrogen, alkyl$_{(C≤12)}$, or substituted alkyl$_{(C≤12)}$;
a compound of the formula:

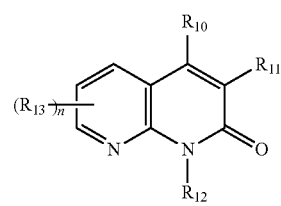

(III)

wherein:
  R$_{10}$ is amino, hydroxy, or aryl$_{(C≤18)}$, aralkyl$_{(C≤18)}$, aryloxy$_{(C≤18)}$, cycloalkylamino$_{(C≤18)}$, aralkoxy$_{(C≤18)}$, arylamino$_{(C≤18)}$, aralkamino$_{(C≤18)}$, diarylamino$_{(C≤18)}$, diaralkamino$_{(C≤18)}$, or a substituted version of any of these groups;
  R$_{11}$ is hydrogen, acyl$_{(C≤12)}$, or substituted acyl$_{(C≤12)}$, or —C(O)R$_a$; wherein:
    R$_a$ is amino, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤8)}$, or substituted dialkylamino$_{(C≤8)}$;

R$_{12}$ is hydrogen, alkoxy$_{(C\leq8)}$, or substituted alkoxy$_{(C\leq8)}$;

R$_{13}$ is amino, cyano, halo, hydroxy, nitro, alkyl$_{(C\leq8)}$, substituted alkyl$_{(C\leq8)}$, acyl$_{(C\leq8)}$, substituted acyl$_{(C\leq8)}$, alkoxy$_{(C\leq8)}$, substituted alkoxy$_{(C\leq8)}$, acyloxy$_{(C\leq8)}$, substituted acyloxy$_{(C\leq8)}$, alkylamino$_{(C\leq8)}$, substituted alkylamino$_{(C\leq8)}$, dialkylamino$_{(C\leq8)}$, substituted dialkylamino$_{(C\leq8)}$, amido$_{(C\leq8)}$, or substituted amido$_{(C\leq8)}$; and n is 1, 2, or 3;

wherein the compound is formulated as a pharmaceutical composition comprising the compound and an excipient, further wherein the pharmaceutical composition is formulated for oral administration, intraarterial administration, intravenous administration, parenteral administration, or for administration to the lungs;

or a pharmaceutically acceptable salt or tautomer thereof.

17. The method of claim 16, wherein the compound is further defined as:

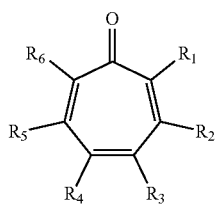

(I)

wherein:

R$_1$ and R$_6$ are each independently hydrogen, halo, or a group of the formula: —X—Y$_1$, wherein:

X is O, S, or NR$_1{}^1$, wherein:

R$_1$' is hydrogen, alkyl$_{(C\leq8)}$, substituted alkyl$_{(C\leq8)}$, aryl$_{(C\leq8)}$, or substituted aryl$_{(C\leq8)}$; and Y$_1$ is hydrogen or alkyl$_{(C\leq12)}$, aryl$_{(C\leq12)}$, acyl$_{(C\leq12)}$, alkylsulfonyl$_{(C\leq12)}$, arylsulfonyl$_{(C\leq12)}$, or a substituted version of any of these groups;

R$_2$ and R$_5$ are each independently hydrogen, hydroxy, halo, alkyl$_{(C\leq12)}$, substituted alkyl$_{(C\leq12)}$, cycloalkyl$_{(C\leq12)}$, substituted cycloalkyl$_{(C\leq12)}$, aryl$_{(C\leq12)}$, substituted aryl$_{(C\leq12)}$, aralkyl$_{(C\leq12)}$, substituted aralkyl$_{(C\leq12)}$, heteroaryl$_{(C\leq12)}$, substituted heteroaryl$_{(C\leq12)}$, alkoxy$_{(C\leq12)}$, substituted alkoxy$_{(C\leq12)}$, acyl$_{(C\leq12)}$, or substituted acyl$_{(C\leq12)}$; and R$_3$ and R$_4$ are each independently hydrogen, hydroxy, halo, nitroso, alkyl$_{(C\leq12)}$, substituted alkyl$_{(C\leq12)}$, cycloalkyl$_{(C\leq12)}$, substituted cycloalkyl$_{(C\leq12)}$, alkenyl$_{(C\leq12)}$, substituted alkenyl$_{(C\leq12)}$, aryl$_{(C\leq18)}$, substituted aryl$_{(C\leq18)}$, heteroaryl$_{(C\leq18)}$, substituted heteroaryl$_{(C\leq18)}$, acyl$_{(C\leq18)}$, substituted acyl$_{(C\leq18)}$, amido$_{(C\leq18)}$, substituted amido$_{(C\leq18)}$, or —C(O)R$_a$, wherein:

R$_a$ is alkyl$_{(C\leq18)}$, cycloalkyl$_{(C\leq18)}$, aryl$_{(C\leq18)}$, heteroaryl$_{(C\leq18)}$, alkoxy$_{(C\leq18)}$, aryloxy$_{(C\leq18)}$, -alkanediyl$_{(C\leq6)}$-cycloalkyl$_{(C\leq12)}$; or a substituted version of any of these groups; or R$_2$ and R$_3$ are taken together and are a compound of the formula:

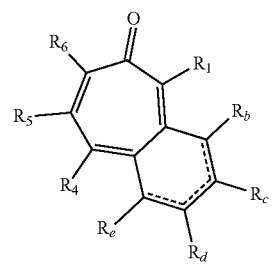

(IA)

wherein:

R$_b$, R$_c$, R$_d$, and R$_e$ are each independently hydrogen, hydroxy, or alkyl$_{(C\leq8)}$, cycloalkyl$_{(C\leq8)}$, alkenyl$_{(C\leq8)}$, or a substituted version of any of these groups; or -alkanediyl$_{(C\leq6)}$-alkylamino$_{(C\leq8)}$, -alkane-diyl$_{(C\leq6)}$-dialkylamino$_{(C\leq8)}$, or a substituted version of either of these groups; or R$_1$ and R$_2$ are taken together and are a compound of the formula:

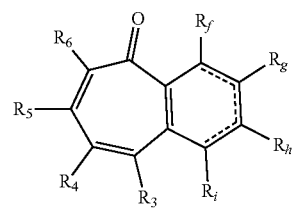

(IB)

wherein:

R$_f$, R$_g$, R$_h$, and R$_i$ are each independently hydrogen, hydroxy, or alkyl$_{(C\leq8)}$, cycloalkyl$_{(C\leq8)}$, alkenyl$_{(C\leq8)}$, or a substituted version of any of these groups; or -alkanediyl$_{(C\leq6)}$-alkylamino$_{(C\leq8)}$, -alkane-diyl$_{(C\leq6)}$-dialkylamino$_{(C\leq8)}$, or a substituted version of either of these groups; or R$_3$ and R$_4$ are taken together and are a compound of the formula:

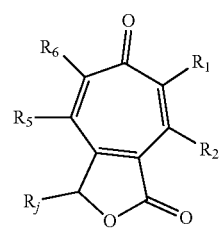

(IC)

wherein:

R$_3$ is hydrogen, hydroxy, halo, or alkyl$_{(C\leq8)}$, cycloalkyl$_{(C\leq8)}$, alkenyl$_{(C\leq8)}$, or a substituted version of any of these groups; or -alkanediyl$_{(C\leq6)}$-alkylamino$_{(C\leq8)}$, -alkanediyl$_{(C\leq6)}$-dialkylamino$_{(C\leq8)}$, or a substituted version of either of these groups; or a compound of the formula:

(II)

wherein:
   $R_7$ is alkyl$_{(C≤12)}$, aryl$_{(C≤12)}$, aralkyl$_{(C≤12)}$, heteroaryl$_{(C≤12)}$, or a substituted version of any of these groups;
   $R_8$ is hydrogen, alkyl$_{(C≤8)}$, or substituted alkyl$_{(C≤8)}$; and $R_9$ is hydrogen, alkyl$_{(C≤12)}$, or substituted alkyl$_{(C≤12)}$;
a compound of the formula:

(III)

wherein:
   $R_{10}$ is amino, hydroxy, or aryl$_{(C≤18)}$, aralkyl$_{(C≤18)}$, aryloxy$_{(C≤18)}$, cycloalkylamino$_{(C≤18)}$, aralkoxy$_{(C≤18)}$, arylamino$_{(C≤18)}$, aralkamino$_{(C≤18)}$, diarylamino$_{(C≤18)}$, diaralkamino$_{(C≤18)}$, or a substituted version of any of these groups;
   $R_{11}$ is hydrogen, acyl$_{(C≤12)}$, or substituted acyl$_{(C≤12)}$, or —C(O)R$_a$; wherein:
      $R_a$ is amino, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤8)}$, or substituted dialkylamino$_{(C≤8)}$;
   $R_{12}$ is hydrogen, alkoxy$_{(C≤8)}$, or substituted alkoxy$_{(C≤8)}$;
   $R_{13}$ is amino, cyano, halo, hydroxy, nitro, alkyl$_{(C≤8)}$, substituted alkyl$_{(C≤8)}$, acyl$_{(C≤8)}$, substituted acyl$_{(C≤8)}$, alkoxy$_{(C≤8)}$, substituted alkoxy$_{(C≤8)}$, acyloxy$_{(C≤8)}$, substituted acyloxy$_{(C≤8)}$, alkylamino$_{(C≤8)}$, substituted alkylamino$_{(C≤8)}$, dialkylamino$_{(C≤8)}$, substituted dialkylamino$_{(C≤8)}$, amido$_{(C≤8)}$, or substituted amido$_{(C≤8)}$; and
   n is 1, 2, or 3;
or a pharmaceutically acceptable salt or tautomer thereof.

18. A pharmaceutical composition comprising:
(A) a compound of the formula:

(I)

wherein:
   $R_1$ and $R_6$ are each independently hydrogen, halo, or a group of the formula: —X—Y$_1$, wherein:
      X is C(O), O, S, or NR$_1'$, wherein:
         $R_1'$ is hydrogen, alkyl$_{(C≤8)}$, substituted alkyl$_{(C≤8)}$, aryl$_{(C≤8)}$, or substituted aryl$_{(C≤8)}$; and
      $Y_1$ is hydrogen, hydroxy, or alkyl$_{(C≤12)}$, aryl$_{(C≤12)}$, acyl$_{(C≤12)}$, alkoxy$_{(C≤12)}$, alkylsulfonyl$_{(C≤12)}$, arylsulfonyl$_{(C≤12)}$, or a substituted version of any of these groups;
   $R_2$ and $R_5$ are each independently hydrogen, hydroxy, halo, alkyl$_{(C≤12)}$, substituted alkyl$_{(C≤12)}$, cycloalkyl$_{(C≤12)}$, substituted cycloalkyl$_{(C≤12)}$, alkenyl$_{(C≤12)}$, substituted alkenyl$_{(C≤12)}$, aryl$_{(C≤12)}$, substituted aryl$_{(C≤12)}$, aralkyl$_{(C≤12)}$, substituted aralkyl$_{(C≤12)}$, heteroaryl$_{(C≤12)}$, substituted heteroaryl$_{(C≤12)}$, alkoxy$_{(C≤12)}$, substituted alkoxy$_{(C≤12)}$, acyl$_{(C≤12)}$, substituted acyl$_{(C≤12)}$, or a group of the formula: —C(O)Y$_2$R$_2'$, wherein:
      $Y_2$ is alkenediyl$_{(C≤8)}$ or substituted alkenediyl$_{(C≤8)}$; and
      $R_2'$ is aryl$_{(C≤12)}$, heteroaryl$_{(C≤12)}$, arenediyl$_{(C≤12)}$-O-aryl$_{(C≤12)}$, or a substituted version of any of these groups; and
   $R_3$ and $R_4$ are each independently hydrogen, hydroxy, halo, nitroso, alkyl$_{(C≤12)}$, substituted alkyl$_{(C≤12)}$, cycloalkyl$_{(C≤12)}$, substituted cycloalkyl$_{(C≤12)}$, alkenyl$_{(C≤12)}$, substituted alkenyl$_{(C≤12)}$, aryl$_{(C≤18)}$, substituted aryl$_{(C≤18)}$, heteroaryl$_{(C≤18)}$, substituted heteroaryl$_{(C≤18)}$, acyl$_{(C≤18)}$, substituted acyl$_{(C≤18)}$, amido$_{(C≤18)}$, substituted amido$_{(C≤18)}$, or —C(O)R$_a$ or —S(O)$_2$R$_a$ wherein:
      $R_a$ is alkyl$_{(C≤18)}$, cycloalkyl$_{(C≤18)}$, aryl$_{(C≤18)}$, heteroaryl$_{(C≤18)}$, alkoxy$_{(C≤18)}$, aryloxy$_{(C≤18)}$, -alkanediyl$_{(C≤6)}$-cycloalkyl$_{(C≤12)}$; or a substituted version of any of these groups; or
   $R_2$ and $R_3$ are taken together and are a compound of the formula:

(IA)

wherein:
   $R_b$, $R_c$, $R_d$, and $R_e$ are each independently hydrogen, hydroxy, or alkyl$_{(C≤8)}$, cycloalkyl$_{(C≤8)}$, alkenyl$_{(C≤8)}$, or a substituted version of any of these groups; or -alkanediyl$_{(C≤6)}$-alkylamino$_{(C≤8)}$, -alkanediyl$_{(C≤6)}$-dialkylamino$_{(C≤8)}$, or a substituted version of either of these groups; or
   $R_1$ and $R_2$ are taken together and are a compound of the formula:

a compound of the formula:

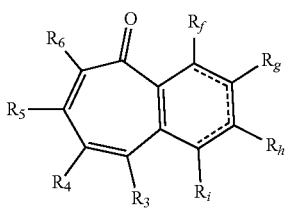

(IB)

wherein:
$R_f$, $R_g$, $R_h$, and $R_i$ are each independently hydrogen, hydroxy, or alkyl$_{(C \leq 8)}$, cycloalkyl$_{(C \leq 8)}$, alkenyl$_{(C \leq 8)}$, or a substituted version of any of these groups; or -alkanediyl$_{(C \leq 6)}$-alkylamino$_{(C \leq 8)}$, -alkane-diyl$_{(C \leq 6)}$-dialkylamino$_{(C \leq 8)}$, or a substituted version of either of these groups; or $R_3$ and $R_4$ are taken together and are a compound of the formula:

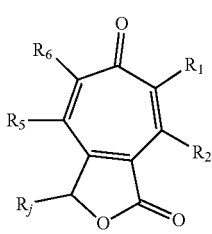

(IC)

wherein:
$R_3$ is hydrogen, hydroxy, halo, or alkyl$_{(C \leq 8)}$, cycloalkyl$_{(C \leq 8)}$, alkenyl$_{(C \leq 8)}$, or a substituted version of any of these groups; or -alkanediyl$_{(C \leq 6)}$-alkylamino$_{(C \leq 8)}$, alkanediyl$_{(C \leq 6)}$-dialkylamino$_{(C \leq 8)}$, or a substituted version of either of these groups; or a compound of the formula:

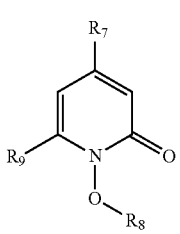

(II)

wherein:
$R_7$ is alkyl$_{(C \leq 12)}$, aryl$_{(C \leq 12)}$, aralkyl$_{(C \leq 12)}$, heteroaryl$_{(C \leq 12)}$, or a substituted version of any of these groups;
$R_8$ is hydrogen, alkyl$_{(C \leq 8)}$, or substituted alkyl$_{(C \leq 8)}$; and
$R_9$ is hydrogen, alkyl$_{(C \leq 12)}$, or substituted alkyl$_{(C \leq 12)}$;

a compound of the formula:

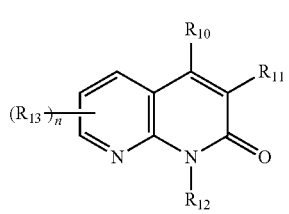

(III)

wherein:
$R_{10}$ is amino, hydroxy, or aryl$_{(C \leq 18)}$, aralkyl$_{(C \leq 18)}$, aryloxy$_{(C \leq 18)}$, cycloalkylamino$_{(C \leq 18)}$, aralkoxy$_{(C \leq 18)}$, arylamino$_{(C \leq 18)}$, aralkamino$_{(C \leq 18)}$, diarylamino$_{(C \leq 18)}$, diaralkamino$_{(C \leq 18)}$, or a substituted version of any of these groups;
$R_{11}$ is hydrogen, acyl$_{(C \leq 12)}$, or substituted acyl$_{(C \leq 12)}$, or —C(O)R$_a$; wherein:
  $R_a$ is amino, hydroxy, alkoxy$_{(C \leq 8)}$, substituted alkoxy$_{(C \leq 8)}$, alkylamino$_{(C \leq 8)}$, substituted alkylamino$_{(C \leq 8)}$, dialkylamino$_{(C \leq 8)}$, or substituted dialkylamino$_{(C \leq 8)}$;
$R_{12}$ is hydrogen, alkoxy$_{(C \leq 8)}$, or substituted alkoxy$_{(C \leq 8)}$;
$R_{13}$ is amino, cyano, halo, hydroxy, nitro, alkyl$_{(C \leq 8)}$, substituted alkyl$_{(C \leq 8)}$, acyl$_{(C \leq 8)}$, substituted acyl$_{(C \leq 8)}$, alkoxy$_{(C \leq 8)}$, substituted alkoxy$_{(C \leq 8)}$, acyloxy$_{(C \leq 8)}$, substituted acyloxy$_{(C \leq 8)}$, alkylamino$_{(C \leq 8)}$, substituted alkylamino$_{(C \leq 8)}$, dialkylamino$_{(C \leq 8)}$, substituted dialkylamino$_{(C \leq 8)}$, amido$_{(C \leq 8)}$, or substituted amido$_{(C \leq 8)}$; and
n is 1, 2, or 3;
or a pharmaceutically acceptable salt or tautomer thereof; and
(B) a second anti-fungal compound;
wherein the pharmaceutical composition is formulated for oral administration, intraarterial administration, intravenous administration, parenteral administration, or for administration to the lungs.

19. The pharmaceutical composition of claim 18, wherein the compound is further defined as:

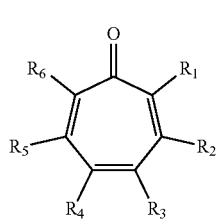

(I)

wherein:
$R_1$ and $R_6$ are each independently hydrogen, halo, or a group of the formula: —X—Y$_1$, wherein:
  X is O, S, or NR$_1$', wherein:
    $R_1$' is hydrogen, alkyl$_{(C \leq 8)}$, substituted alkyl$_{(C \leq 8)}$, aryl$_{(C \leq 8)}$, or substituted aryl$_{(C \leq 8)}$; and
  $Y_1$ is hydrogen or alkyl$_{(C \leq 12)}$, aryl$_{(C \leq 12)}$, acyl$_{(C \leq 12)}$, alkylsulfonyl$_{(C \leq 12)}$, arylsulfonyl$_{(C \leq 12)}$, or a substituted version of any of these groups;
$R_2$ and $R_5$ are each independently hydrogen, hydroxy, halo, alkyl$_{(C \leq 12)}$, substituted alkyl$_{(C \leq 12)}$, cycloalkyl$_{(C≤12)}$, substituted cycloalkyl$_{(C≤12)}$, aryl$_{(C≤12)}$, substituted aryl$_{(C≤12)}$, aralkyl$_{(C≤12)}$, substituted aralkyl$_{(C≤12)}$, heteroaryl$_{(C≤12)}$, substituted heteroaryl$_{(C≤12)}$, alkoxy$_{(C≤12)}$, substituted alkoxy$_{(C≤12)}$, acyl$_{(C≤12)}$, or substituted acyl$_{(C≤12)}$; and $R_3$ and $R_4$ are each independently hydrogen, hydroxy, halo, nitroso, alkyl$_{(C≤12)}$, substituted alkyl$_{(C≤12)}$, cycloalkyl$_{(C≤12)}$, substituted cycloalkyl$_{(C≤12)}$, alkenyl$_{(C≤12)}$, substituted alkenyl$_{(C≤12)}$, aryl$_{(C≤18)}$, substituted aryl$_{(C≤18)}$, heteroaryl$_{(C≤18)}$, substituted heteroaryl$_{(C≤18)}$, acyl$_{(C≤18)}$, substituted acyl$_{(C≤18)}$, amido$_{(C≤18)}$, substituted amido$_{(C≤18)}$, or —C(O)$R_a$, wherein:

$R_a$ is alkyl$_{(C≤18)}$, cycloalkyl$_{(C≤18)}$, aryl$_{(C≤18)}$, heteroaryl$_{(C≤18)}$, alkoxy$_{(C≤18)}$, aryloxy$_{(C≤18)}$, -alkanediyl$_{(C≤6)}$-cycloalkyl$_{(C≤12)}$; or a substituted version of any of these groups; or $R_2$ and $R_3$ are taken together and are a compound of the formula:

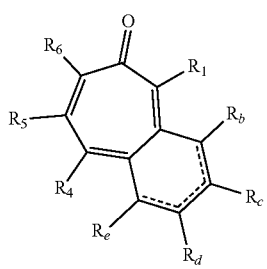

(IA)

wherein:

$R_b$, $R_c$, $R_d$, and $R_e$ are each independently hydrogen, hydroxy, or alkyl$_{(C≤8)}$, cycloalkyl$_{(C≤8)}$, alkenyl$_{(C≤8)}$, or a substituted version of any of these groups; or -alkanediyl$_{(C≤6)}$-alkylamino$_{(C≤8)}$, -alkane-diyl$_{(C≤6)}$-dialkylamino$_{(C≤8)}$, or a substituted version of either of these groups; or $R_1$ and $R_2$ are taken together and are a compound of the formula:

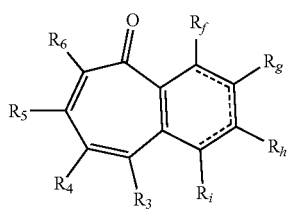

(IB)

wherein:

$R_f$, $R_g$, $R_h$, and $R_i$ are each independently hydrogen, hydroxy, or alkyl$_{(C≤8)}$, cycloalkyl$_{(C≤8)}$, alkenyl$_{(C≤8)}$, or a substituted version of any of these groups; or -alkanediyl$_{(C≤6)}$-alkylamino$_{(C≤8)}$, -alkane-diyl$_{(C≤6)}$-dialkylamino$_{(C≤8)}$, or a substituted version of either of these groups; or $R_3$ and $R_4$ are taken together and are a compound of the formula:

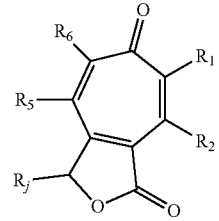

(IC)

wherein:

$R_3$ is hydrogen, hydroxy, halo, or alkyl$_{(C≤8)}$, cycloalkyl$_{(C≤8)}$, alkenyl$_{(C≤8)}$, or a substituted version of any of these groups; or -alkanediyl$_{(C≤6)}$-alkylamino$_{(C≤8)}$, -alkane-diyl$_{(C≤6)}$-dialkylamino$_{(C≤8)}$, or a substituted version of either of these groups; or a compound of the formula:

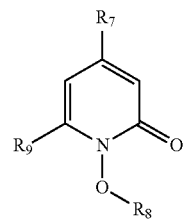

(II)

wherein:

$R_7$ is alkyl$_{(C≤12)}$, aryl$_{(C≤12)}$, aralkyl$_{(C≤12)}$, heteroaryl$_{(C≤12)}$, or a substituted version of any of these groups;

$R_8$ is hydrogen, alkyl$_{(C≤8)}$, or substituted alkyl$_{(C≤8)}$; and $R_9$ is hydrogen, alkyl$_{(C≤12)}$, or substituted alkyl$_{(C≤12)}$;

a compound of the formula:

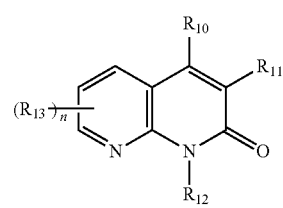

(III)

wherein:

$R_{10}$ is amino, hydroxy, or aryl$_{(C≤18)}$, aralkyl$_{(C≤18)}$, aryloxy$_{(C≤18)}$, cycloalkylamino$_{(C≤18)}$, aralkoxy$_{(C≤18)}$, arylamino$_{(C≤18)}$, aralkamino$_{(C≤18)}$, diarylamino$_{(C≤18)}$, diaralkamino$_{(C≤18)}$, or a substituted version of any of these groups;

$R_{11}$ is hydrogen, acyl$_{(C≤12)}$, or substituted acyl$_{(C≤12)}$, or —C(O)$R_a$; wherein:

$R_a$ is amino, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤8)}$, or substituted dialkylamino$_{(C≤8)}$;

$R_{12}$ is hydrogen, alkoxy$_{(C≤8)}$, or substituted alkoxy$_{(C≤8)}$;

$R_{13}$ is amino, cyano, halo, hydroxy, nitro, alkyl$_{(C≤8)}$, substituted alkyl$_{(C≤8)}$, acyl$_{(C≤8)}$, substituted acyl$_{(C\leq 8)}$, alkoxy$_{(C\leq 8)}$, substituted alkoxy$_{(C\leq 8)}$, acyloxy$_{(C\leq 8)}$, substituted acyloxy$_{(C\leq 8)}$, alkylamino$_{(C\leq 8)}$, substituted alkylamino$_{(C\leq 8)}$, dialkylamino$_{(C\leq 8)}$, substituted dialkylamino$_{(C\leq 8)}$, amido$_{(C\leq 8)}$, or substituted amido$_{(C\leq 8)}$; and n is 1, 2, or 3;

or a pharmaceutically acceptable salt or tautomer thereof.

\* \* \* \* \*

UNITED STATES PATENT AND TRADEMARK OFFICE
CERTIFICATE OF CORRECTION

PATENT NO. : 10,980,754 B2
APPLICATION NO. : 16/094682
DATED : April 20, 2021
INVENTOR(S) : Maureen J. Donlin et al.

It is certified that error appears in the above-identified patent and that said Letters Patent is hereby corrected as shown below:

In the Claims

In Claim 2, Column 99, Line 40, delete "$R_3$" and insert --$R_j$-- therefor.

In Claim 17, Column 120, Line 62, delete "$R_3$" and insert --$R_j$-- therefor.

In Claim 18, Column 123, Line 38, delete "$R_3$" and insert --$R_j$-- therefor.

In Claim 19, Column 126, Line 14, delete "$R_3$" and insert --$R_j$-- therefor.

Signed and Sealed this
Twelfth Day of October, 2021

Drew Hirshfeld
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

| | |
|---|---|
| PATENT NO. | : 10,980,754 B2 |
| APPLICATION NO. | : 16/094682 |
| DATED | : April 20, 2021 |
| INVENTOR(S) | : Donlin et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 170 days.

Signed and Sealed this
Thirty-first Day of January, 2023

*Katherine Kelly Vidal*

Katherine Kelly Vidal
*Director of the United States Patent and Trademark Office*